(12) United States Patent
Blaschuk et al.

(10) Patent No.: US 6,610,821 B1
(45) Date of Patent: *Aug. 26, 2003

(54) COMPOUNDS AND METHODS FOR MODULATING ENDOTHELIAL CELL ADHESION

(75) Inventors: Orest W. Blaschuk, Westmount (CA); Barbara J. Gour, Kemptville (CA); Riaz Farookhi, Montreal (CA); Anmar Ali, Ottawa (CA)

(73) Assignee: McGill University, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/544,782

(22) Filed: Apr. 7, 2000

Related U.S. Application Data

(63) Continuation-in-part of application No. 09/458,870, filed on Dec. 10, 1999, now Pat. No. 6,465,427, which is a continuation-in-part of application No. 09/357,717, filed on Jul. 20, 1999, now Pat. No. 6,417,325, which is a continuation-in-part of application No. 09/248,074, filed on Feb. 10, 1999, now Pat. No. 6,346,512, which is a continuation-in-part of application No. 08/996,679, filed on Dec. 23, 1997, now Pat. No. 6,169,071, which is a continuation-in-part of application No. 08/893,534, filed on Jul. 11, 1997, now Pat. No. 6,031,072.

(60) Provisional application No. 60/021,612, filed on Jul. 12, 1996.

(51) Int. Cl.$^7$ .......................... A61K 38/00; A61K 38/12
(52) U.S. Cl. ...................... 530/317; 530/326; 530/327; 530/328; 530/329; 530/330; 530/331; 514/9; 514/4; 514/14; 514/15; 514/16; 514/17; 514/18; 435/7.21; 435/7.23
(58) Field of Search ............................ 514/9, 4, 15, 16, 514/17, 18, 14; 530/317, 326, 327, 328, 329, 330, 331; 435/7.21, 7.23

(56) References Cited

U.S. PATENT DOCUMENTS

| | | | | |
|---|---|---|---|---|
| 5,231,082 A | | 7/1993 | Schasteen ..................... | 514/11 |
| 5,245,551 A | * | 9/1993 | Herron et al. ................ | 364/497 |
| 5,352,667 A | | 10/1994 | Lider et al. .................... | 514/19 |
| 5,510,628 A | | 4/1996 | Georger, Jr. et al. .......... | 257/32 |
| 5,585,351 A | | 12/1996 | Ranscht ......................... | 514/12 |
| 5,591,432 A | | 1/1997 | Bronson et al. .......... | 424/130.1 |
| 5,646,250 A | | 7/1997 | Suzuki ........................ | 530/350 |
| 5,665,590 A | | 9/1997 | Yang .............................. | 435/6 |
| 6,031,072 A | * | 2/2000 | Blaschuk et al. ............ | 530/317 |
| 6,169,071 B1 | * | 1/2001 | Blaschuk et al. ............... | 514/4 |
| 6,326,352 B1 | * | 12/2001 | Blaschuk et al. ............... | 514/9 |

FOREIGN PATENT DOCUMENTS

| | | |
|---|---|---|
| EP | 406 428 B1 | 1/1991 |
| WO | WO 91/04745 | 4/1991 |
| WO | WO 92/08731 | 5/1992 |
| WO | WO 94/11401 | 5/1994 |
| WO | WO 96/40781 | 12/1996 |
| WO | WO 97/07209 | 2/1997 |
| WO | WO 98/02452 | 1/1998 |
| WO | WO 98/45319 | 10/1998 |
| WO | WO 99/33875 | 7/1999 |

OTHER PUBLICATIONS

Blaschuk et al., "A Novel Cadherin Antagonist (Exherin) Blocks Human Ovarian Tumor Growth in Nude Mice," *Molecular Biology of the Cell* 10: 72A, Nov. 1999.

Starzinski–Powitz et al., "The putative role of cell adhesion molecules in endometriosis: can we learn from tumour metastasis?," *Molecular Medicine Today* 5: 304–309, Jul. 1999.

Williams et al., "A Novel Family of Cyclic Peptide Antagonists Suggests That N–cadherin Specificity Is Determined by Amino Acids That Flank the HAV Motif," *The Journal of Biological Chemistry* 275(6): 4007–4012, Feb. 11, 2000.

Alexander et al., "An N–Cadherin–Like Protein Contributes to Solute Barrier Maintenance in Cultured Endothelium," *Journal of Cellular Physiology* 156: 610–618, 1993.

Ali et al., "Conformationally Constrained Peptides and Semipeptides Derived from RGD as Potent Inhibitors of the Platelet Fibrinogen Receptor and Platelet Aggregation," *J. Med. Chem.* 37(6): 769–780, 1994.

Beesley et al., "The post–synaptic density: putative involvement in synapse stabilization via cahderins and covalent modification by ubiquitination," *Biochemical Society Transactions* 23: 59–64, 1995.

Blakemore, "Remyelination of CNS axons by Schwann cells transplanted from the sciatic nerve," *Nature* 266: 68–69, 1977.

Blaschuk and Farookhi, "Estradiol Stimulates Cadherin Expression in Rat Granulosa Cells," *Developmental Biology* 136: 564–567, 1989.

Blaschuk et al., "E–Cadherin, estrogens and cancer: is there a connection?" *The Canadian Journal of Oncology* 4(4): 291–301, 1994.

Blaschuk et al., "Identification of a Cadherin Cell Adhesion Recognition Sequence," *Developmental Biology* 139: 227–229, 1990.

Blaschuk et al., "Identification of a Conserved Region Common to Cadherins and Influenza Strain A Hemagglutinins," *J. Mol. Biol.* 211: 679–682, 1990.

Bottenstein and Sato, "Growth of a rat neuroblastoma cell line in serum–free supplemented medium," *Proc.Natl. Acad. Sci. USA* 76(1): 514–517, 1979.

Brecknell et al., "Bridge grafts of Fibroblast Growth Factor–4–Secreting Schwannoma Cells Promote Functional Axonal Regeneration in the Nigrostriatal Pathway of the Adult Rat," *Neuroscience* 74(3): 775–784, 1996.

(List continued on next page.)

Primary Examiner—Christopher S. F. Low
Assistant Examiner—Chih-Min Kam
(74) Attorney, Agent, or Firm—Seed Intellectual Property Law Group PLLC

(57) ABSTRACT

Cyclic peptides comprising a cadherin cell adhesion recognition sequence HAV, and compositions comprising such cyclic peptides, are provided. Methods for using such peptides for modulating cadherin-mediated endothelial cell adhesion in a variety of contexts are also provided.

19 Claims, 24 Drawing Sheets

OTHER PUBLICATIONS

Brockes et al., "Studies on Cultured Rat Schwann Cells. I. Establishment of Purified Populations from Cultures of Peripheral Nerve," *Brain Research 165:* 105–118, 1979.

Brook et al., "Morphology and Migration of Cultured Schwann Cells Transplanted Into the Fimbria and Hippocampus in Adult Rats," *GLIA 9:* 292–304, 1993.

Byers et al., "Fibroblast Growth Factor Receptors Contain a Conserved HAV Region Common to Cadherins and Influenza Strain A Hemagglutinins: A Role in Protein–Protein Interactions?," *Developmental Biology 152:* 411–414, 1992.

Cardarelli et al., "The Collagen Receptor $\alpha 2\beta 1$, from MG–63 and HT1080 Cells, Interacts with a Cyclic RGD Peptide," *The Journal of Biological Chemistry 267*(32): 23159–23164, 1992.

Carlstedt et al., "Nerve Fibre Regeneration Across the PNS–CNS Interface at the Root–Spinal Cord Junction," *Brain Research Bulletin 22:* 93–102, 1989.

Cepek et al., "Expression of a candidate cadherin in T lymphocytes," *Proc. Natl. Acad. Sci. USA 93:* 6567–6571, 1996.

Chuah et al., "Differentiation and survival of rat olfactory epithelial neurons in dissociated cell culture," *Developmental Brain Research 60:* 123–132, 1991.

Craig et al., "Concept and Progress in the Development of RGD–Containing Peptide Pharmaceuticals," *Biopolymers (Peptide Science) 37:* 157–175, 1995.

Doherty and Walsh, "CAM–FGF Receptor Interactions: A Model for Axonal Growth," *Molecular and Cellular Neuroscience 8*(Article No. 0049): 99–111, 1996.

Doherty and Walsh, "Signal transduction events underlying neurite outgrowth stimulated by cell adhesion molecules," *Current Opinion in Neurobiology 4:* 49–55, 1994.

Doherty et al., "Neurite Outgrowth in Response to Transfected N–CAM and N–Cadherin Reveals Fundamental Differences in Neuronal Responsiveness to CAMS," *Neuron 6:* 247–258, 1991.

Duncan et al., "Transplantation of oligodendrocytes and Schwann cells into the spinal cord of the myelin–deficient rat," *Journal of Neurocytology 17:* 351–360, 1988.

Fok–Seang et al., "An analysis of astrocytic cell lines with different abilities to promote axon growth," *Brain Research 689:* 207–223, 1995.

Fok–Seang et al., "Migration of Oligodendrocyte Precursors on Astrocytes and Meningeal Cells," *Development Biology 171:* 1–15, 1995.

Franz, "Percutaneous Absorption. On The Relevance Of In Vitro Data," *The Journal of Investigative Dermatology 64*(3): 190–195, 1975.

Franz, "The Finite Dose Techniques as a Valid in Vitro Model for the Study of Percutaneous Absorption in Man," *Curr. Probl. Dermatol. 7:* 58–68, 1978.

Ghirnikar and Eng, "Astrocyte–Schwann Cell Interactions in Culture," *GLIA 11:* 367–377, 1994.

Gumbiner et al., "The Role of the Cell Adhesion Molecule Uvomorulin in the Formation and Maintenance of the Epithelial Junctional Complex," *The Journal of Cell Biology 107:* 1575–1587, 1988.

Iruela–Arispe et al., "Expression of SPARC during Development of the Chicken Chorioallantoic Membrane: Evidence for Regulated Proteolysis in Vivo," *Molecular Biology of the Cell 6:* 327–343, 1995.

Laird et al., "Gap Junction Turnover, Intracellular Trafficking, and Phosphorylation of Connexin43 in Brefeldin A–treated Rat Mammary Tumor Cells," *The Journal of Cell Biology 131*(5): 1193–1203, 1995.

Lee et al., "Expression of the Homotypic Adhesion Molecule E–Cadherin by Immature Murine Thymocytes and Thymic Epithelial Cells," *Journal of Immunology 152:* 5653–5659, 1994.

Letourneau et al., "Interactions of Schwann Cells with Neurites and with Other Schwann Cells Involve the Calcium–dependent Adhesion Molecule, N–cadherin," *Journal of Neurobiology 22*(7): 707–720, 1991.

Liuzzi and Lasek, "Astrocytes Block Axonal Regeneration in Mammals by Activating the Physiological Stop Pathway," *Science 237:* 642–645, 1987.

Lutz et al., "Secondary Structure of the HAV Peptide Which Regulates Cadherin–Cadherin Interaction," *Journal of Biomolecular Structure & Dynamics 13*(3): 447–455, 1995.

Matsuzaki et al., "cDNAs of Cell Adhesion Molecules of Different Specificity Induce Changes in Cell Shape Border Formation in Cultured S180 Cells," *The Journal of Cell Biology 110:* 1239–1252, 1990.

McCarthy and Vellis, "Preparation of Separate Astroglial and Oligodendroglial Cell Cultures from Rat Cerebral Tissue," *J. Cell Biology 85:* 890–902, 1980.

Mege et al., "Construction of epithelioid sheets by transfection of mouse sarcoma cells with cDNAs for chicken cell adhesion molecules," *Proc. Natl. Acad. Sci. USA 85:* 7274–7278, 1988.

Moran, "The Protein Delivery Serivce. Advances in technologies for delivering proteins and peptides in therapeutically useful forms," *Pharmaceutical Forum Issue 6:* 4–7, 1996.

Munro and Blaschuk, *Cell Adhesion and Invasion in Cancer Metastasis,* R.G. Landes Company, Austin, TX, 1996, Chapter 3, "The Structure, Function and Regulation of Cadherins," pp. 17–34.

Munro et al., "Characterization of Cadherins Expressed by Murine Thymocytes," *Cellular Immunology 169*(Article No. 0123): 309–312, 1996.

Newton et al., "N–Cadherin Mediates Sertoli Cell–Spermatogenic Cell Adhesion," *Developmental Dynamics 197:* 1–13, 1993.

Nose et al., "Localization of Specificity Determining Sites in Cadherin Cell Adhesion Molecules," *Cell 61:* 147–155, 1990.

Orr, "Angiogenesis Research Offers New Approaches to Treatment of Disease," *Genetic Engineering News,* pp. 15–16, 42, May 1, 1996.

Overduin et al., "Solution Structure of the Epithelial Cadherin Domain Responsible for Selective Cell Adhesion," *Science 267:* 386–389, 1995.

Redies and Takeichi, "Cadherins in the Developing Central Nervous System: An Adhesive Code for Segmental and Functional Subdivisions," *Developmental Biology 180:* 413–423, 1996.

Saffell et al., "Expression of a Dominant Negative FGF Receptor Inhibits Axonal Growth and FGF Receptor Phosphorylation Stimulated by CAMs," *Neuron,* pp. 231–242, Feb. 1997.

Samanen et al., "Development of a Small RGD Peptide Fibrinogen Receptor Antagonist with Potent Antiaggregatory Acivity in Vitro," *J. Med. Chem.* 34(10): 3114–3125, 1991.

Shapiro et al., "Structural basis of cell–cell adhesion by cadherins," *Nature* 374: 327–337, 1995.

Tsutsui et al., "Expression of Cadherin–Catenin Complexes in Human Leukemia Cell Lines," *J. Biochem.* 120: 1034–1039, 1996.

Wickelgren, "Breaking the Skin Barrier," *PS 12:* 86–88, 1996.

Willems et al., "Cadherin–dependent cell aggregation is affected by decapeptide derived from rat extracellular super–oxide dismutase," *FEBS Letters* 363: 289–292, 1995.

Williams et al., "Activation of the FGF Receptor Underlies Neurite Outgrowth Stimulated by L1, N–CAM, and N–Cadherin," *Neuron* 13: 583–594, 1994.

Williams et al., "The Primary Stucture of Hen Ovotransferrin," *Eur. J. Biochem.* 122: 297–303, 1982.

* cited by examiner

```
human N-cad  DWVIPPINLPENSRGPFPQELVRIRSDRDKNLSLRYSVTGPGADQPPTGIFILNPISGQLSVTKPLDREQ
mouse N-cad  DWVIPPINLPENSRGPFPQELVRIRSDRDKNLSLRYSVTGPGADQPPTGIFILNPISGQLSVTKPLDREL
cow   N-cad  DWVIPPINLPENSRGPFPQELVRIRSDRDKNLSLRYSVTGPGADQPPTGIFIINPISGQLSVTKPLDREL
human P-cad  DWVVAPISVPENGKGPFPQRLNQLKSNKDRDTKIFYSITGPGADSPPEGVFAVEKETGWLLLNKPLDREE
mouse P-cad  EWVMPPIFVPENGKGPFPQRLNQLKSNKDRGTKIFYSITGPGADSPPEGVFTIEKESGWLLLHMPLDREK
human E-cad  DWVIPPISCPENEKGPFPKNLVQIKSNKDKEGKVFYSITGQGADTPPVGVFIIERETGWLKVTEPLDRER
mouse E-cad  DWVIPPISCPENEKGEFPKNLVQIKSNRDKETKVFYSITGQGADKPPVGVFIIERETGWLKVTQPLDREA human N-cad  IARFHLRAHAVDINGNQVENPIDIVINVIDMNDNRPEF
mouse N-cad  IARFHLRAHAVDINGNQVENPIDIVINVIDMNDNRPEF
cow   N-cad  IARFHLRAHAVDINGNQVENPIDIVINVIDMNDNRPEF
human P-cad  IAKYELFGHAVSENGASVEDPMNISIIVTDQNDHKPKF
mouse P-cad  IVKYELYGHAVSENGASVEEPMNISIIVTDQNDNKPKF
human E-cad  IATYTLFSHAVSSNGNAVEDPMEILITVTDQNDNKPEF
mouse E-cad  IAKYILYSHAVSSNGLAVEDPMEIVITVTDQNDNRPEF
```

*Fig. 2*

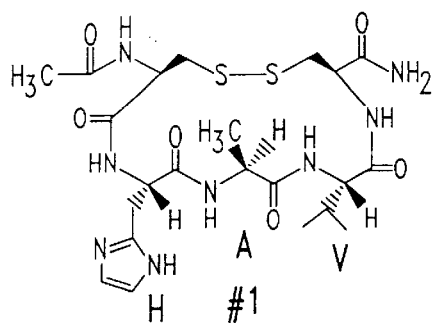
N-Ac-CHAVC-NH₂
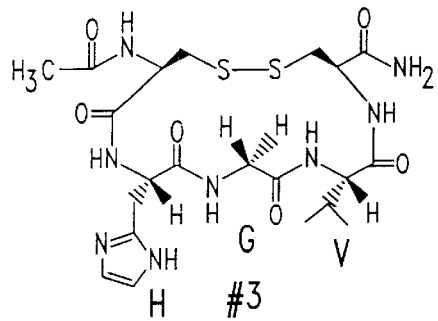
N-Ac-CHGVC-NH₂
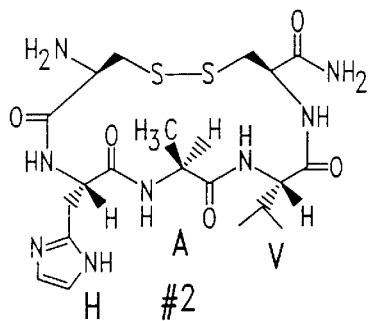
H-CHAVC-NH₂
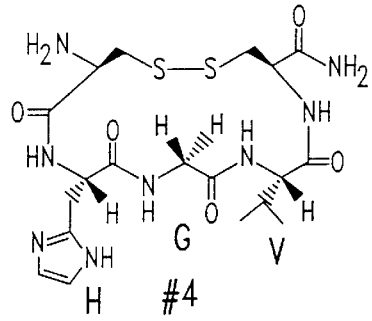
H-CHGVC-NH₂
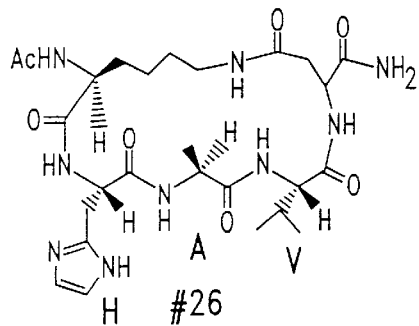
N-Ac-KHAVD-NH₂
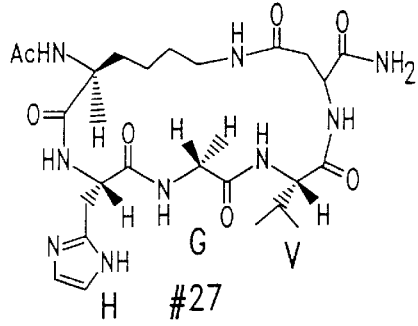
N-Ac-KHGVD-NH₂
Fig. 3A

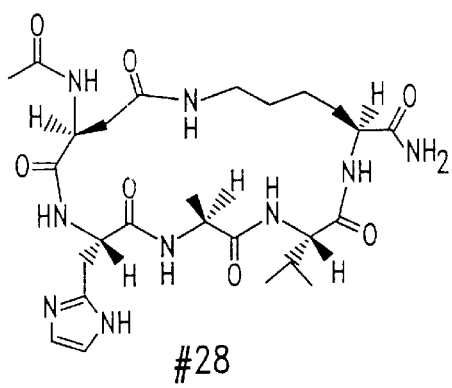
28
N-Ac-DHAVK-NH$_2$
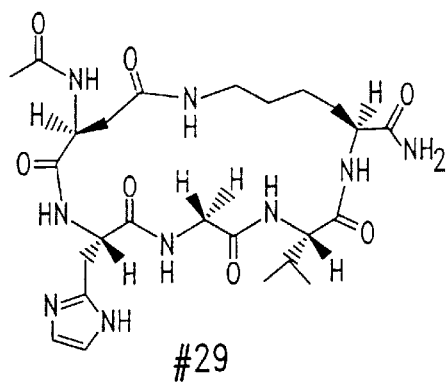
29
N-Ac-DHGVK-NH$_2$
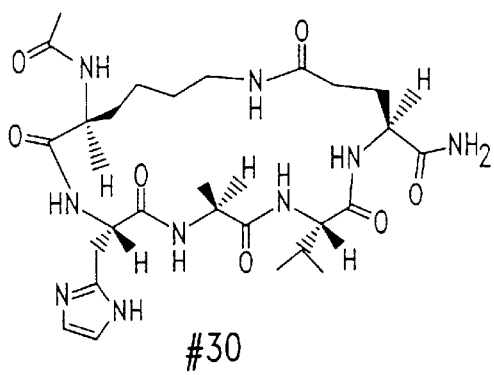
30
N-Ac-KHAVE-NH$_2$
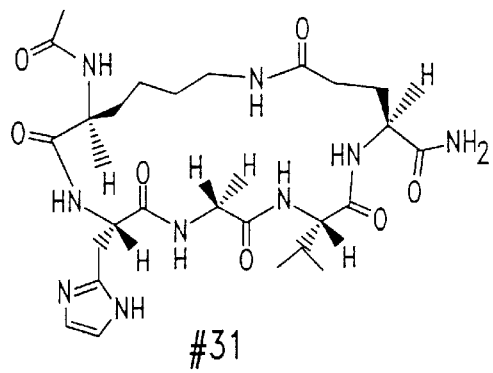
31
N-Ac-KHGVE-NH$_2$
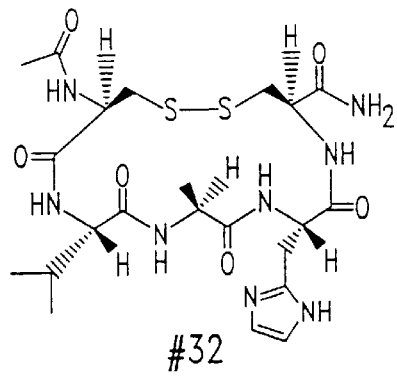
32
N-Ac-CVAHC-NH$_2$
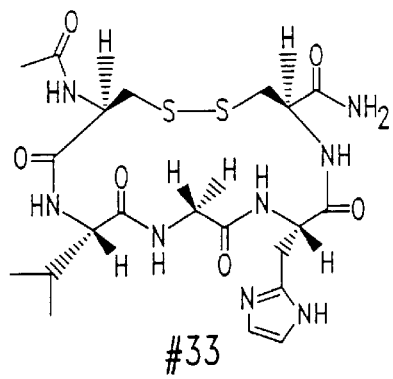
33
N-Ac-CVGHC-NH$_2$
Fig. 3B

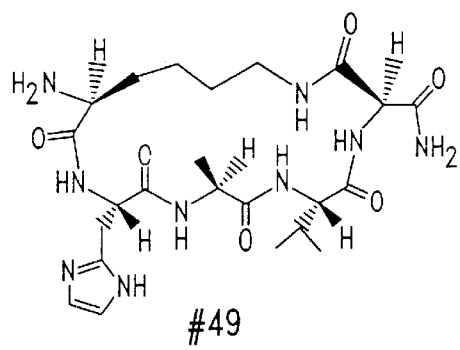
49
H-KHAVD-NH$_2$
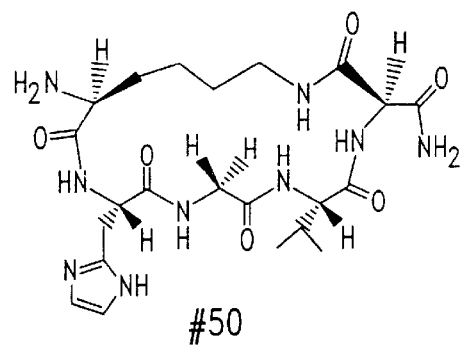
50
H-KHGVD-NH$_2$
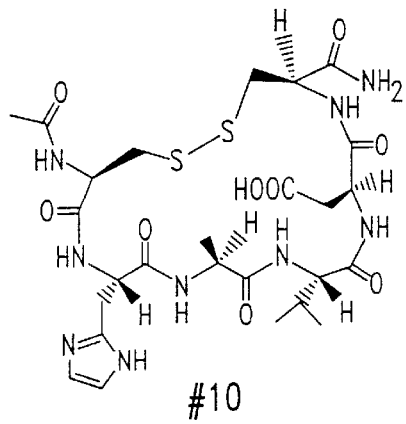
10
N-Ac-CHAVDC-NH$_2$
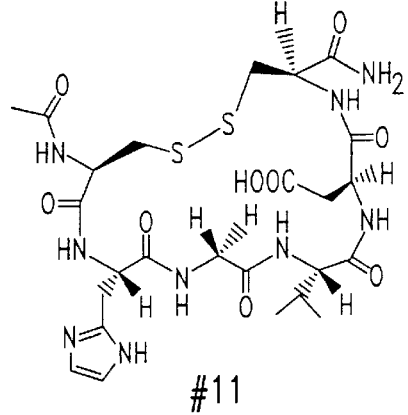
11
N-Ac-CHGVDC-NH$_2$
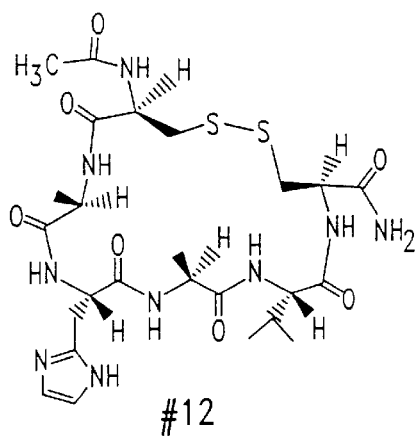
12
N-Ac-CAHAVC-NH$_2$
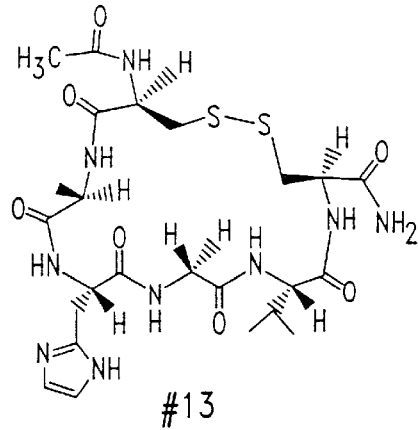
13
N-Ac-CAHGVC-NH$_2$
Fig. 3C

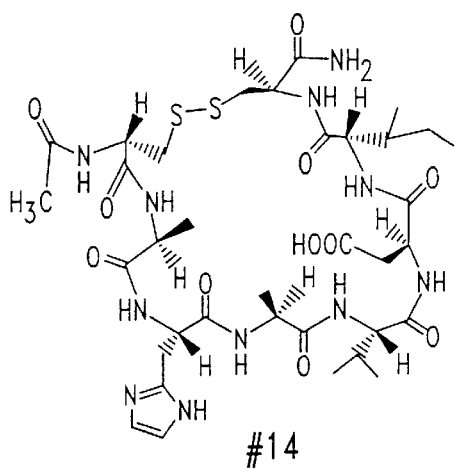
14
N-Ac-CAHAVDIC-NH₂
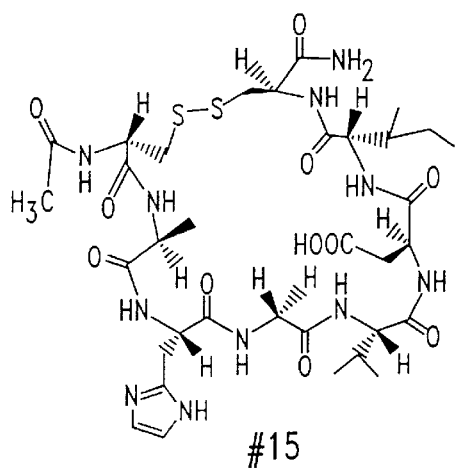
15
N-Ac-CAHGVDIC-NH₂
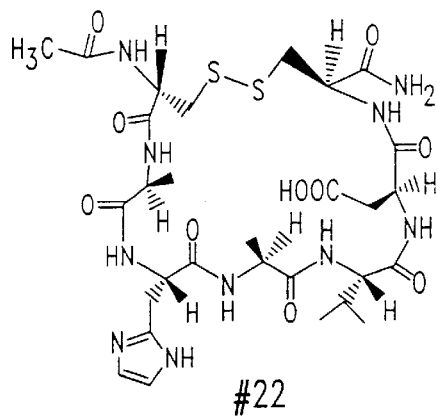
22
N-Ac-CAHAVDC-NH₂
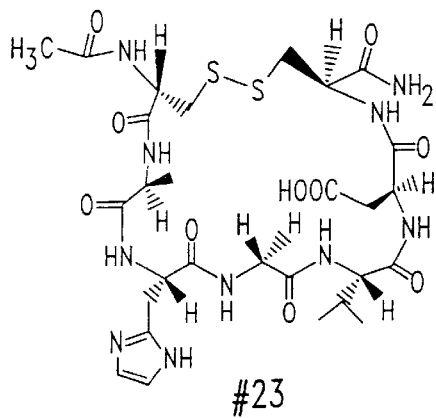
23
N-Ac-CAHGVDC-NH₂
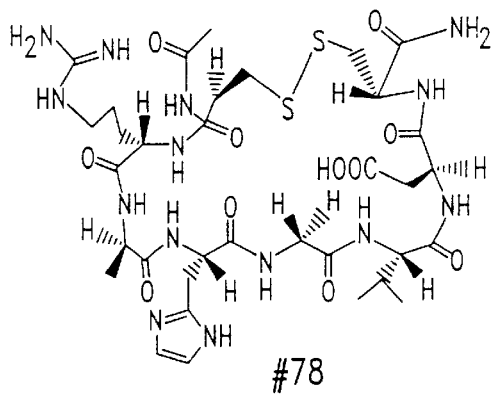
78
N-Ac-CRAHAVDC-NH₂
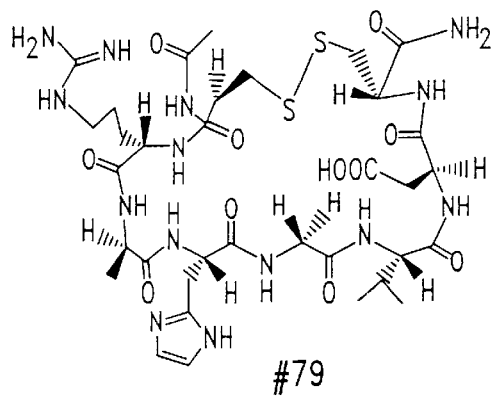
79
N-Ac-CRAHGVDC-NH₂
Fig. 3D

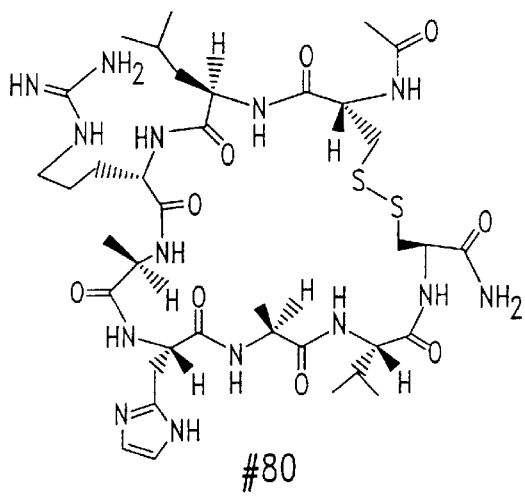
80
N-Ac-CLRAHAVC-NH₂
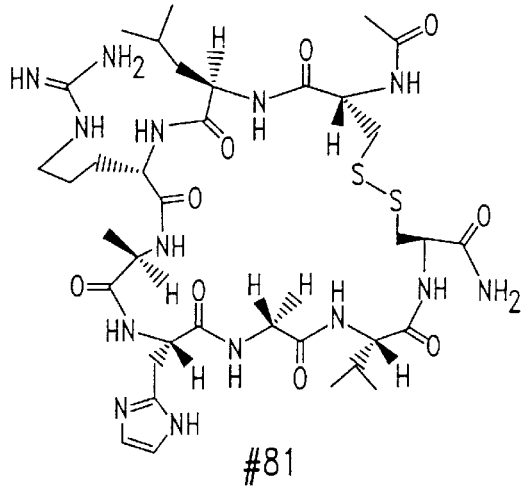
81
N-Ac-CLRAHGVC-NH₂
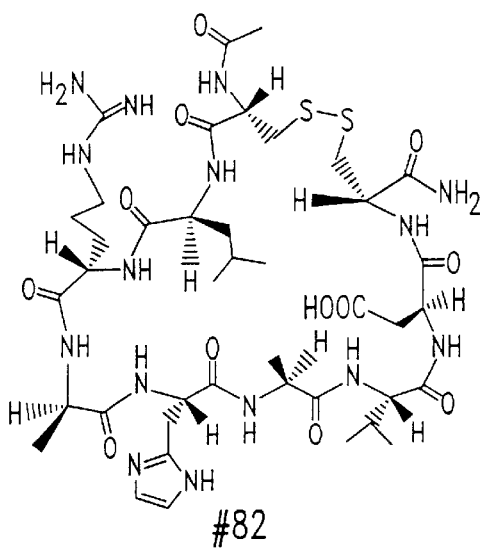
82
N-Ac-CLRAHAVDC-NH₂
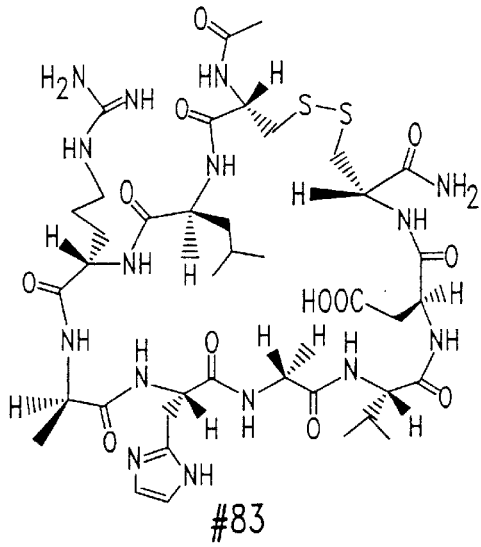
83
N-Ac-CLRAHGVDC-NH₂
*Fig. 3E*

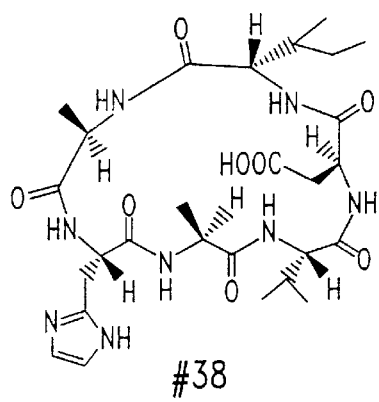
38
AHAVDI
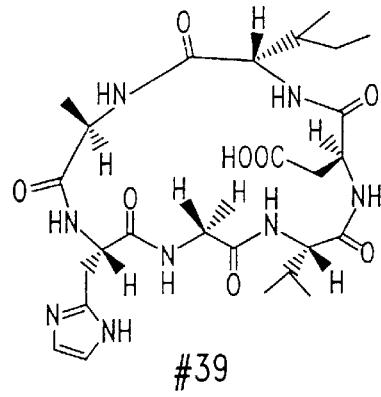
39
AHGVDI
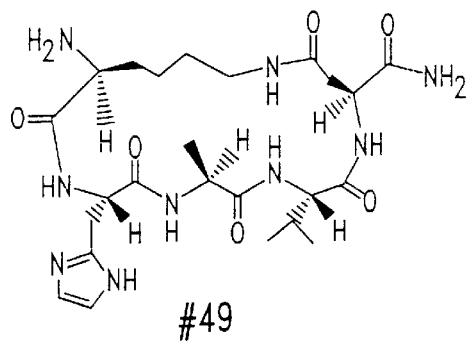
49
H-KHAVD-NH$_2$
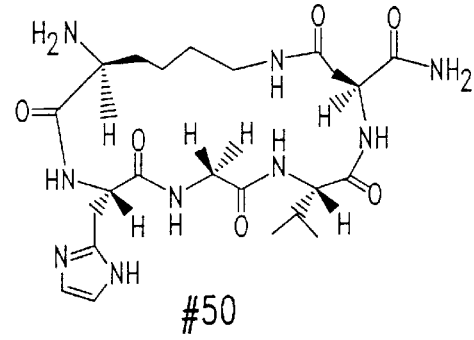
50
H-KHGVD-NH$_2$
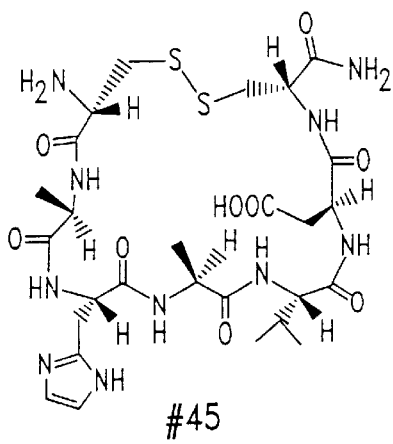
45
H-CAHAVDC-NH$_2$
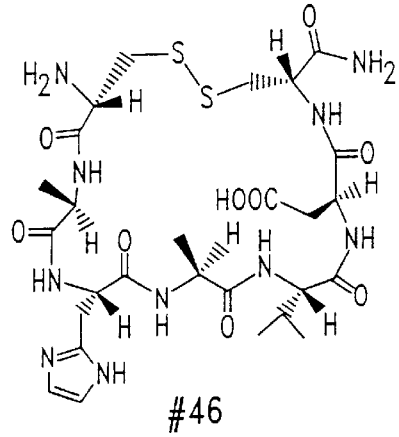
46
H-CAHGVDC-NH$_2$
Fig. 3F

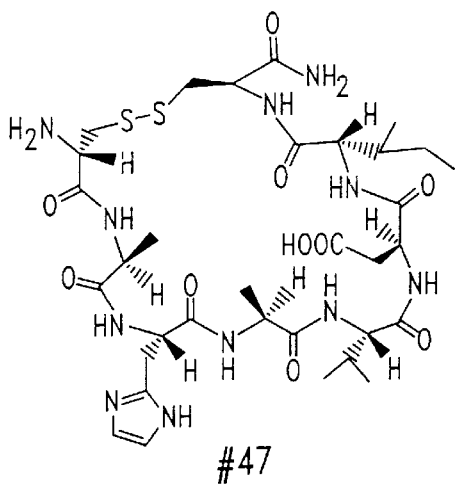
47
H-CAHAVDIC-NH2
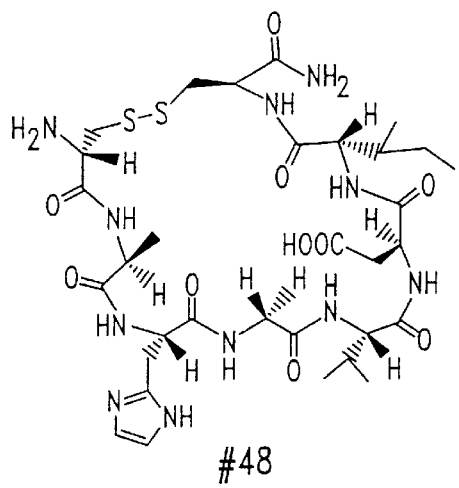
48
H-CAHGVDIC-NH2
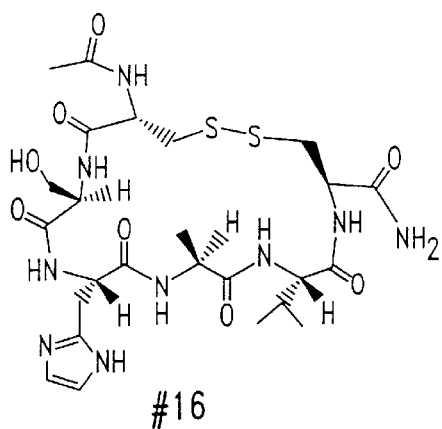
16
N-Ac-CSHAVC-NH2
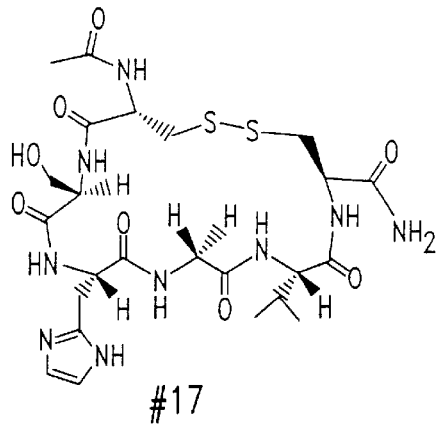
17
N-Ac-CSHGVC-NH2
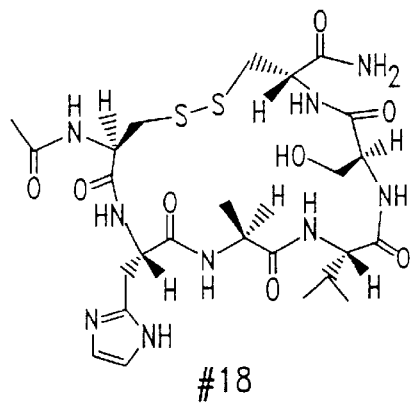
18
N-Ac-CHAVSC-NH2
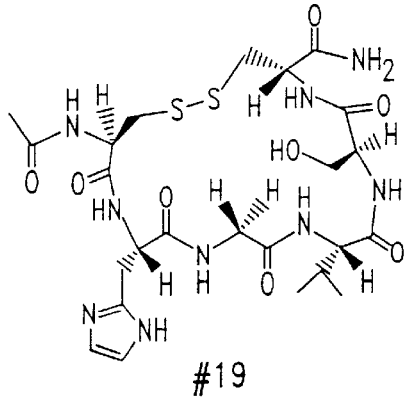
19
N-Ac-CHGVSC-NH2
Fig. 3G

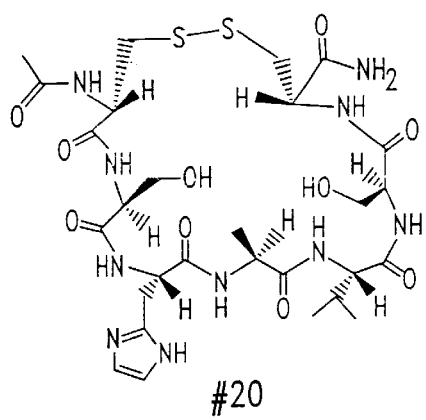
20
N-Ac-CSHAVSC-NH$_2$
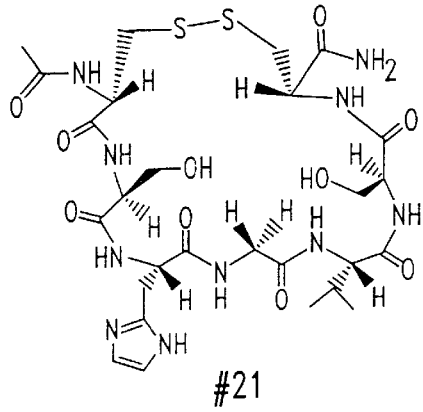
21
N-Ac-CSHGVSC-NH$_2$
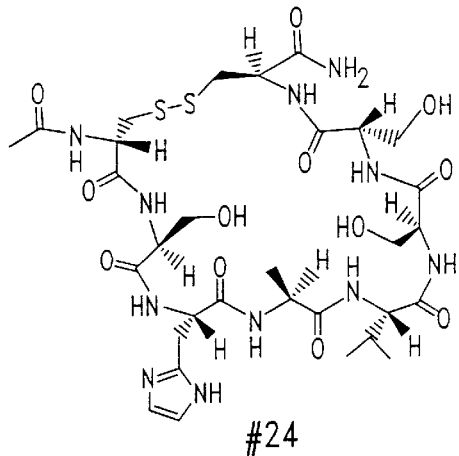
24
N-Ac-CSHAVSSC-NH$_2$
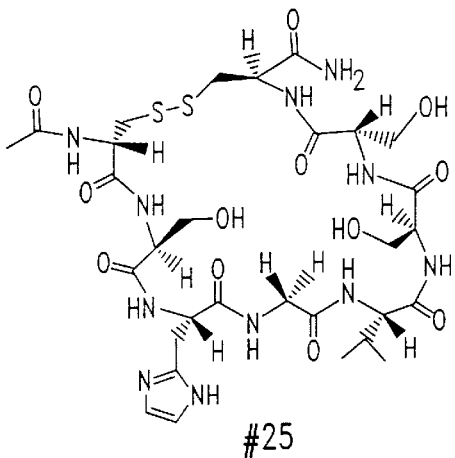
25
N-Ac-CSHGVSSC-NH$_2$
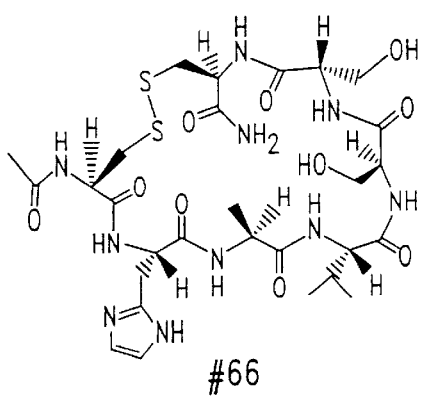
66
N-Ac-CHAVSSC-NH$_2$
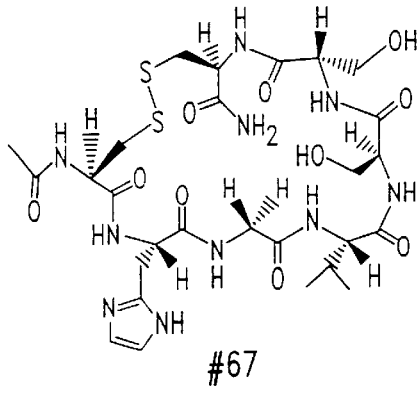
67
N-Ac-CHGVSSC-NH$_2$
Fig. 3H

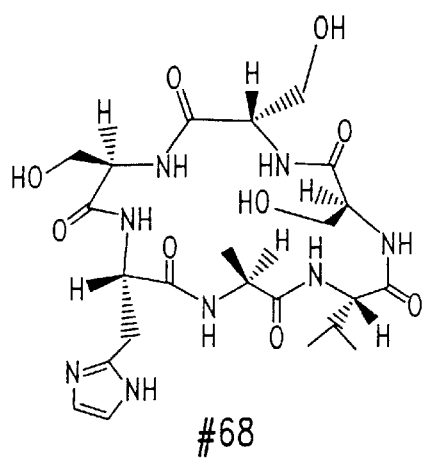
68
SHAVSS
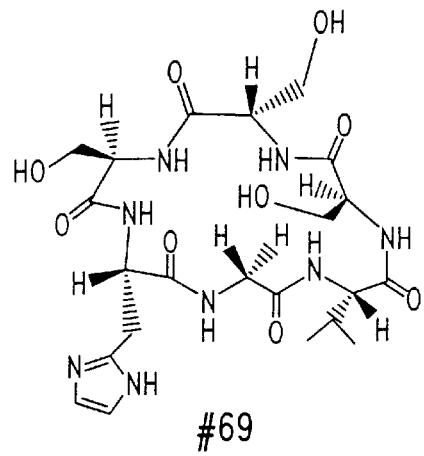
69
SHGVSS
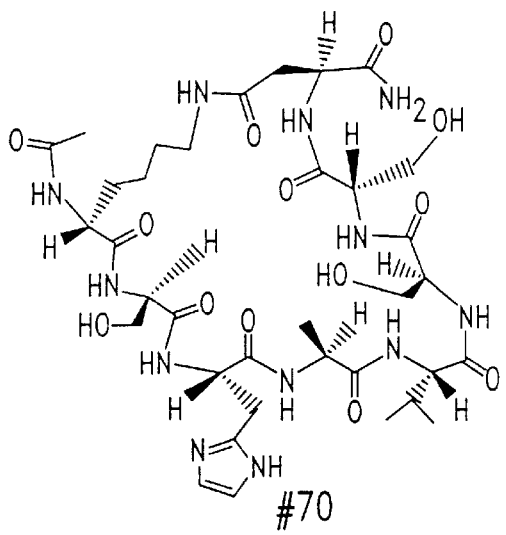
70
N-Ac-KSHAVSSD-NH$_2$
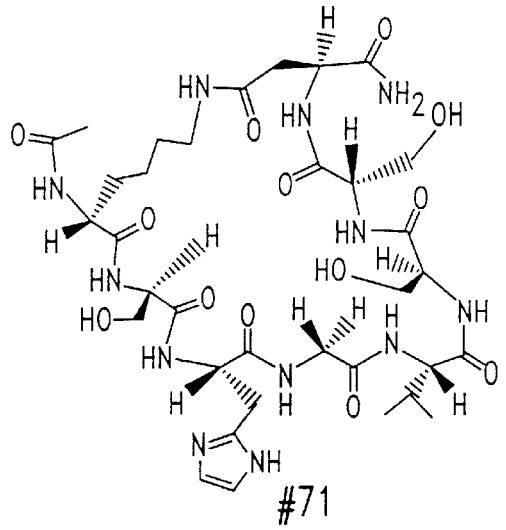
71
N-Ac-KSHGVSSD-NH$_2$
Fig. 31

SEQUENCE LISTING

<160> NUMBER OF SEQ ID NOS: 96

<210> SEQ ID NO 1
<211> LENGTH: 108
<212> TYPE: PRT
<213> ORGANISM: Homo sapiens

<400> SEQUENCE: 1

```
Asp Trp Val Ile Pro Pro Ile Asn Leu Pro Glu Asn Ser Arg Gly Pro
 1               5                  10                  15

Phe Pro Gln Glu Leu Val Arg Ile Arg Ser Asp Arg Asp Lys Asn Leu
            20                  25                  30

Ser Leu Arg Tyr Ser Val Thr Gly Pro Gly Ala Asp Gln Pro Pro Thr
        35                  40                  45

Gly Ile Phe Ile Leu Asn Pro Ile Ser Gly Gln Leu Ser Val Thr Lys
    50                  55                  60

Pro Leu Asp Arg Glu Gln Ile Ala Arg Phe His Leu Arg Ala His Ala
65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe
            100                 105
```

<210> SEQ ID NO 2

```
<211> LENGTH: 108
<212> TYPE: PRT
<213> ORGANISM: Mus musculus

<400> SEQUENCE: 2

Asp Trp Val Ile Pro Pro Ile Asn Leu Pro Glu Asn Ser Arg Gly Pro
  1               5                  10                  15

Phe Pro Gln Glu Leu Val Arg Ile Arg Ser Asp Arg Asp Lys Asn Leu
                 20                  25                  30

Ser Leu Arg Tyr Ser Val Thr Gly Pro Gly Ala Asp Gln Pro Pro Thr
             35                  40                  45

Gly Ile Phe Ile Ile Asn Pro Ile Ser Gly Gln Leu Ser Val Thr Lys
         50                  55                  60

Pro Leu Asp Arg Glu Leu Ile Ala Arg Phe His Leu Arg Ala His Ala
 65                  70                  75                  80

Val Asp Ile Asn Gly Asn Gln Val Glu Asn Pro Ile Asp Ile Val Ile
                 85                  90                  95

Asn Val Ile Asp Met Asn Asp Asn Arg Pro Glu Phe
                100                 105

<210> SEQ ID NO 3
<211> LENGTH: 108
<212> TYPE: PRT
<213> ORGANISM: Bos taurus

<400> SEQUENCE: 3

Asp Trp Val Ile Pro Pro Ile Asn Leu Pro Glu Asn Ser Arg Gly Pro
  1               5                  10                  15

Phe Pro Gln Glu Leu Val Arg Ile Arg Ser Asp Arg Asp Lys Asn Leu
                 20                  25                  30

Ser Leu Arg Tyr Ser Val Thr Gly Pro Gly Ala Asp Gln Pro Pro Thr
             35                  40                  45

Gly Ile Phe Ile Ile Asn Pro Ile Ser Gly Gln Leu Ser Val Thr Lys
         50                  55                  60

Pro Leu Asp Arg Glu Leu Ile Ala Arg Phe His Leu Arg Ala His Ala
 65                  70                  75                  80

Val Asp Ile Asn Gly Asn Gln Val Glu Asn Pro Ile Asp Ile Val Ile
                 85                  90                  95

Asn Val Ile Asp Met Asn Asp Asn Arg Pro Glu Phe
                100                 105

<210> SEQ ID NO 4
<211> LENGTH: 108
<212> TYPE: PRT
<213> ORGANISM: Homo sapiens

<400> SEQUENCE: 4

Asp Trp Val Val Ala Pro Ile Ser Val Pro Glu Asn Gly Lys Gly Pro
  1               5                  10                  15

Phe Pro Gln Arg Leu Asn Gln Leu Lys Ser Asn Lys Asp Arg Asp Thr
                 20                  25                  30

Lys Ile Phe Tyr Ser Ile Thr Gly Pro Gly Ala Asp Ser Pro Pro Glu
             35                  40                  45

Gly Val Phe Ala Val Glu Lys Glu Thr Gly Trp Leu Leu Leu Asn Lys
         50                  55                  60

Pro Leu Asp Arg Glu Glu Ile Ala Lys Tyr Glu Leu Phe Gly His Ala
 65                  70                  75                  80
```

-continued

Val Ser Glu Asn Gly Ala Ser Val Glu Pro Met Asn Ile Ser Ile
                85                  90                  95

Ile Val Thr Asp Gln Asn Asp His Lys Pro Lys Phe
            100                 105

<210> SEQ ID NO 5
<211> LENGTH: 108
<212> TYPE: PRT
<213> ORGANISM: Mus musculus

<400> SEQUENCE: 5

Glu Trp Val Met Pro Ile Phe Val Pro Glu Asn Gly Lys Gly Pro
  1               5                  10                  15

Phe Pro Gln Arg Leu Asn Gln Leu Lys Ser Asn Lys Asp Arg Gly Thr
                20                  25                  30

Lys Ile Phe Tyr Ser Ile Thr Gly Pro Gly Ala Asp Ser Pro Pro Glu
            35                  40                  45

Gly Val Phe Thr Ile Glu Lys Glu Ser Gly Trp Leu Leu Leu His Met
    50                  55                  60

Pro Leu Asp Arg Glu Lys Ile Val Lys Tyr Glu Leu Tyr Gly His Ala
 65                 70                  75                  80

Val Ser Glu Asn Gly Ala Ser Val Glu Glu Pro Met Asn Ile Ser Ile
                85                  90                  95

Ile Val Thr Asp Gln Asn Asp Asn Lys Pro Lys Phe
            100                 105

<210> SEQ ID NO 6
<211> LENGTH: 108
<212> TYPE: PRT
<213> ORGANISM: Homo sapiens

<400> SEQUENCE: 6

Asp Trp Val Ile Pro Pro Ile Ser Cys Pro Glu Asn Glu Lys Gly Pro
  1               5                  10                  15

Phe Pro Lys Asn Leu Val Gln Ile Lys Ser Asn Lys Asp Lys Glu Gly
                20                  25                  30

Lys Val Phe Tyr Ser Ile Thr Gly Gln Gly Ala Asp Thr Pro Pro Val
            35                  40                  45

Gly Val Phe Ile Ile Glu Arg Glu Thr Gly Trp Leu Lys Val Thr Glu
    50                  55                  60

Pro Leu Asp Arg Glu Arg Ile Ala Thr Tyr Thr Leu Phe Ser His Ala
 65                 70                  75                  80

Val Ser Ser Asn Gly Asn Ala Val Glu Asp Pro Met Glu Ile Leu Ile
                85                  90                  95

Thr Val Thr Asp Gln Asn Asp Asn Lys Pro Glu Phe
            100                 105

<210> SEQ ID NO 7
<211> LENGTH: 108
<212> TYPE: PRT
<213> ORGANISM: Mus musculus

<400> SEQUENCE: 7

Asp Trp Val Ile Pro Pro Ile Ser Cys Pro Glu Asn Glu Lys Gly Glu
  1               5                  10                  15

Phe Pro Lys Asn Leu Val Gln Ile Lys Ser Asn Arg Asp Lys Glu Thr
                20                  25                  30

Lys Val Phe Tyr Ser Ile Thr Gly Gln Gly Ala Asp Lys Pro Pro Val

```
                    35                  40                  45
Gly Val Phe Ile Ile Glu Arg Glu Thr Gly Trp Leu Lys Val Thr Gln
        50                  55                  60

Pro Leu Asp Arg Glu Ala Ile Ala Lys Tyr Ile Leu Tyr Ser His Ala
65                  70                  75                  80

Val Ser Ser Asn Gly Glu Ala Val Glu Asp Pro Met Glu Ile Val Ile
                85                  90                  95

Thr Val Thr Asp Gln Asn Asp Asn Arg Pro Glu Phe
                100                 105

<210> SEQ ID NO 8
<211> LENGTH: 5
<212> TYPE: PRT
<213> ORGANISM: Unknown
<220> FEATURE:
<221> NAME/KEY: MOD_RES
<222> LOCATION: (2)
<223> OTHER INFORMATION: Where Xaa is any amino acid
<223> OTHER INFORMATION: Description of Unknown Organism:  Cadherin
      Calcium Binding Motif

<400> SEQUENCE: 8

Asp Xaa Asn Asp Asn
1               5

<210> SEQ ID NO 9
<211> LENGTH: 4
<212> TYPE: PRT
<213> ORGANISM: Unknown
<220> FEATURE:
<223> OTHER INFORMATION: Description of Unknown Organism:  Cadherin
      Calcium Binding Motif

<400> SEQUENCE: 9

Leu Asp Arg Glu
  1

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 10

Cys His Ala Val Cys
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 11

Cys His Gly Val Cys
1               5
```

```
<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Cyclic
      peptide with cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 12

Lys His Ala Val Asp
 1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 13

Lys His Gly Val Asp
 1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Cyclic
      peptide with cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 14

Asp His Ala Val Lys
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 15

Asp His Gly Val Lys
 1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group
```

```
<400> SEQUENCE: 16

Lys His Ala Val Glu
 1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 17

Lys His Gly Val Glu
 1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 18

Cys Val Ala His Cys
 1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 19

Cys Val Gly His Cys
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 20

Cys His Ala Val Asp Cys
 1               5

<210> SEQ ID NO 21
<211> LENGTH: 6
<212> TYPE: PRT
<213> ORGANISM: Artificial Sequence
```

```
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 21

Cys His Gly Val Asp Cys
 1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 22

Cys Ala His Ala Val Cys
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 23

Cys Ala His Gly Val Cys
 1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 24

Cys Ala His Ala Val Asp Ile Cys
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 25

Cys Ala His Gly Val Asp Ile Cys
 1               5
```

```
<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 26

Cys Ala His Ala Val Asp Cys
 1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 27

Cys Ala His Gly Val Asp Cys
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 28

Cys Arg Ala His Ala Val Asp Cys
 1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 29

Cys Arg Ala His Gly Val Asp Cys
 1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion recognition sequence
<223> OTHER INFORMATION: Cyclic Peptide may comprise N-terminal
      modification such as acetyl or alkoxybenzyl group and/or C-
```

```
        terminal modifications such as amide or ester group

<400> SEQUENCE: 30

Cys Leu Arg Ala His Ala Val Cys
  1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 31

Cys Leu Arg Ala His Gly Val Cys
  1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 32

Cys Leu Arg Ala His Ala Val Asp Cys
  1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 33

Cys Leu Arg Ala His Gly Val Asp Cys
  1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 34

Ala His Ala Val Asp Ile
  1               5

<210> SEQ ID NO 35
<211> LENGTH: 6
<212> TYPE: PRT
```

```
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 35

Ala His Gly Val Asp Ile
 1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 36

Cys Ser His Ala Val Cys
 1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 37

Cys Ser His Gly Val Cys
 1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 38

Cys His Ala Val Ser Cys
 1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 39

Cys His Gly Val Ser Cys
```

```
             1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 40

Cys Ser His Ala Val Ser Cys
  1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 41

Cys Ser His Gly Val Ser Cys
  1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 42

Cys Ser His Ala Val Ser Ser Cys
  1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 43

Cys Ser His Gly Val Ser Ser Cys
  1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
``` modification such as acetyl or alkoxybenzyl group and/or C-
        terminal modifications such as amide or ester group

<400> SEQUENCE: 44

Cys His Ala Val Ser Ser Cys
 1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Cyclic
        control peptide
<223> OTHER INFORMATION: Cyclic Peptide may comprise N-terminal
        modification such as acetyl or alkoxybenzyl group and/or C-
        terminal modifications such as amide or ester group

<400> SEQUENCE: 45

Cys His Gly Val Ser Ser Cys
 1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Cyclic
        peptide with classical cadherin cell adhesion recognition sequence
<223> OTHER INFORMATION: Cyclic Peptide may comprise N-terminal
        modification such as acetyl or alkoxybenzyl group and/or C-
        terminal modifications such as amide or ester group

<400> SEQUENCE: 46

Ser His Ala Val Ser Ser
 1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Cyclic
        control peptide
<223> OTHER INFORMATION: Cyclic Peptide may comprise N-terminal
        modification such as acetyl or alkoxybenzyl group and/or C-
        terminal modifications such as amide or ester group

<400> SEQUENCE: 47

Ser His Gly Val Ser Ser
 1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Cyclic
        peptide with classical cadherin cell adhesion recognition sequence
<223> OTHER INFORMATION: Cyclic Peptide may comprise N-terminal
        modification such as acetyl or alkoxybenzyl group and/or C-
        terminal modifications such as amide or ester group

<400> SEQUENCE: 48

Lys Ser His Ala Val Ser Ser Asp
 1               5

<210> SEQ ID NO 49
<211> LENGTH: 8

```
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group and/or C-
      terminal modifications such as amide or ester group

<400> SEQUENCE: 49

Lys Ser His Gly Val Ser Ser Asp
  1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 50

Cys His Ala Val Asp Ile Cys
  1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 51

Cys His Ala Val Asp Ile Asn Cys
  1               5

<210> SEQ ID NO 52
<211> LENGTH: 5
<212> TYPE: PRT
<213> ORGANISM: Unknown
<220> FEATURE:
<223> OTHER INFORMATION: Description of Unknown Organism:  Cadherin cell
      adhesion recognition sequencebound by alpha-6-beta-1 integrin

<400> SEQUENCE: 52

Tyr Ile Gly Ser Arg
  1               5

<210> SEQ ID NO 53
<211> LENGTH: 10
<212> TYPE: PRT
<213> ORGANISM: Unknown
<220> FEATURE:
<223> OTHER INFORMATION: Description of Unknown Organism:  Cadherin cell
      adhesion recognition sequence bound by N-CAM

<400> SEQUENCE: 53

Lys Tyr Ser Phe Asn Tyr Asp Gly Ser Glu
  1               5                  10

<210> SEQ ID NO 54
<211> LENGTH: 6
```

```
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 54

Tyr Cys His Ala Val Cys
 1               5

<210> SEQ ID NO 55
<211> LENGTH: 4
<212> TYPE: PRT
<213> ORGANISM: Unknown
<220> FEATURE:
<223> OTHER INFORMATION: Description of Unknown Organism:  Occluding
      cell adhesion recognition sequence

<400> SEQUENCE: 55

Leu Tyr His Tyr
 1

<210> SEQ ID NO 56
<211> LENGTH: 8
<212> TYPE: PRT
<213> ORGANISM: Unknown
<220> FEATURE:
<223> OTHER INFORMATION: Description of Unknown Organism:  Claudin cell
      adhesion recognition sequence
<221> NAME/KEY: MOD_RES
<222> LOCATION: (2)
<223> OTHER INFORMATION: Where Xaa is either Lysine or arginine
<221> NAME/KEY: MOD_RES
<222> LOCATION: (3)..(4)
<223> OTHER INFORMATION: Where Xaa is an independently selected amino
      acid residue
<221> NAME/KEY: MOD_RES
<222> LOCATION: (5)
<223> OTHER INFORMATION: Where Xaa is either Serine or Alanine
<221> NAME/KEY: MOD_RES
<222> LOCATION: (6)
<223> OTHER INFORMATION: Where Xaa is either Tyrosine or Phenylalanine
<221> NAME/KEY: MOD_RES
<222> LOCATION: (7)
<223> OTHER INFORMATION: Where Xaa is an independently selected amino
      acid residue

<400> SEQUENCE: 56

Trp Xaa Xaa Xaa Xaa Xaa Xaa Gly
 1               5

<210> SEQ ID NO 57
<211> LENGTH: 9
<212> TYPE: PRT
<213> ORGANISM: Unknown
<220> FEATURE:
<223> OTHER INFORMATION: Description of Unknown Organism:  Nonclassical
      cadherin cell adhesion recognition sequence
<221> NAME/KEY: MOD_RES
<222> LOCATION: (1)
<223> OTHER INFORMATION: Where Xaa is an independently selected amino
      acid residue
<221> NAME/KEY: MOD_RES
<222> LOCATION: (3)
<223> OTHER INFORMATION: Where Xaa is an independently selected amino
      acid residue
<221> NAME/KEY: MOD_RES
<222> LOCATION: (4)
<223> OTHER INFORMATION: Where Xaa is Isoleucine, Leucine or Valine
<221> NAME/KEY: MOD_RES
```

```
<222> LOCATION: (5)
<223> OTHER INFORMATION: Where Xaa is Aspartic Acid, Asparagine or
      Glutamic Acid
<221> NAME/KEY: MOD_RES
<222> LOCATION: (6)..(7)
<223> OTHER INFORMATION: Where Xaa is an independently selected amino
      acid residue
<221> NAME/KEY: MOD_RES
<222> LOCATION: (8)
<223> OTHER INFORMATION: Where Xaa is Serine, Threonine or Asparagine

<400> SEQUENCE: 57

Xaa Phe Xaa Xaa Xaa Xaa Xaa Xaa Gly
 1               5

<210> SEQ ID NO 58
<211> LENGTH: 4
<212> TYPE: PRT
<213> ORGANISM: Unknown
<220> FEATURE:
<223> OTHER INFORMATION: Description of Unknown Organism:
      Representative claudin cell adhesion recognition sequence

<400> SEQUENCE: 58

Ile Tyr Ser Tyr
 1

<210> SEQ ID NO 59
<211> LENGTH: 4
<212> TYPE: PRT
<213> ORGANISM: Unknown
<220> FEATURE:
<223> OTHER INFORMATION: Description of Unknown Organism:
      Representative claudin cell adhesion recognition sequence

<400> SEQUENCE: 59

Thr Ser Ser Tyr
 1

<210> SEQ ID NO 60
<211> LENGTH: 4
<212> TYPE: PRT
<213> ORGANISM: Unknown
<220> FEATURE:
<223> OTHER INFORMATION: Description of Unknown Organism:
      Representative claudin cell adhesion recognition sequence

<400> SEQUENCE: 60

Val Thr Ala Phe
 1

<210> SEQ ID NO 61
<211> LENGTH: 4
<212> TYPE: PRT
<213> ORGANISM: Unknown
<220> FEATURE:
<223> OTHER INFORMATION: Description of Unknown Organism:
      Representative claudin cell adhesion recognition sequence

<400> SEQUENCE: 61

Val Ser Ala Phe
 1

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence:
```

```
        Synthesized Peptide
<221> NAME/KEY: MOD_RES
<222> LOCATION: (1)
<223> OTHER INFORMATION: BLOCKED by 9-fluorenymethyloxycarbonyl
<221> NAME/KEY: MOD_RES
<222> LOCATION: (2)
<223> OTHER INFORMATION: tert-butyl protecting group
<221> NAME/KEY: MOD_RES
<222> LOCATION: (4)
<223> OTHER INFORMATION: tert-butyl protecting group
<221> NAME/KEY: MOD_RES
<222> LOCATION: (6)
<223> OTHER INFORMATION: t-Butoxycarbonyl protecting group
<221> NAME/KEY: MOD_RES
<222> LOCATION: (7)
<223> OTHER INFORMATION: tert-butyl protecting group
<221> NAME/KEY: MOD_RES
<222> LOCATION: (9)
<223> OTHER INFORMATION: tert-butyl protecting group
<221> NAME/KEY: MOD_RES
<222> LOCATION: (10)
<223> OTHER INFORMATION: Methoxy terminal group

<400> SEQUENCE: 62

Cys Asp Gly Tyr Pro Lys Asp Cys Lys Gly
 1               5                  10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence:
      Synthesized Cyclic Peptide
<221> NAME/KEY: MOD_RES
<222> LOCATION: (1)
<223> OTHER INFORMATION: 9-fluorenylmethoxycarbonyl protecting group
<221> NAME/KEY: MOD_RES
<222> LOCATION: (2)
<223> OTHER INFORMATION: tert-butyl protecting group
<221> NAME/KEY: MOD_RES
<222> LOCATION: (4)
<223> OTHER INFORMATION: tert-butyl protecting group
<221> NAME/KEY: MOD_RES
<222> LOCATION: (6)
<223> OTHER INFORMATION: t-butoxycarbonyl protecting group
<221> NAME/KEY: MOD_RES
<222> LOCATION: (7)
<223> OTHER INFORMATION: tert-butyl protecting group
<221> NAME/KEY: MOD_RES
<222> LOCATION: (9)
<223> OTHER INFORMATION: tert-butyl protecting group
<221> NAME/KEY: MOD_RES
<222> LOCATION: (10)
<223> OTHER INFORMATION: Methoxy terminal group

<400> SEQUENCE: 63

Cys Asp Gly Tyr Pro Lys Asp Cys Lys Gly
 1               5                  10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence:
      Synthesized peptide
<221> NAME/KEY: MOD_RES
<222> LOCATION: (1)
<223> OTHER INFORMATION: Residue has t-butoxycarbonyl, and Trityl or
      Acetamidomethyl protecting groups
<221> NAME/KEY: MOD_RES
<222> LOCATION: (5)..(6)
<223> OTHER INFORMATION: tert-butyl protecting group
<221> NAME/KEY: MOD_RES
```

```
<222> LOCATION: (7)
<223> OTHER INFORMATION: Trityl or acetaminomethly protecting group

<400> SEQUENCE: 64

Cys Gly Asn Leu Ser Thr Cys Met Leu Gly
 1               5                  10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence:
      Synthesized cyclic peptide
<221> NAME/KEY: MOD_RES
<222> LOCATION: (1)
<223> OTHER INFORMATION: t-butoxycarbonyl protecting group
<221> NAME/KEY: MOD_RES
<222> LOCATION: (5)..(6)
<223> OTHER INFORMATION: tert-butyl protecting group

<400> SEQUENCE: 65

Cys Gly Asn Leu Ser Thr Cys Met Leu Gly
 1               5                  10

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence:
      Synthesized peptide
<221> NAME/KEY: MOD_RES
<222> LOCATION: (2)
<223> OTHER INFORMATION: Residue has Acetamidomethyl or
      tert-Acetaminomethyl or tert-butyl protecting group
<221> NAME/KEY: MOD_RES
<222> LOCATION: (6)
<223> OTHER INFORMATION: Residue has Acetamidomethyl, tert-
      Acetamidomethyl or tert-butyl protecting group
<221> NAME/KEY: MOD_RES
<222> LOCATION: (9)
<223> OTHER INFORMATION: AMIDATION

<400> SEQUENCE: 66

Cys Tyr Ile Gln Asn Cys Pro Leu Gly
 1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence:
      Synthesized cyclic peptide
<221> NAME/KEY: MOD_RES
<222> LOCATION: (9)
<223> OTHER INFORMATION: AMIDATION

<400> SEQUENCE: 67

Cys Tyr Ile Gln Asn Cys Pro Leu Gly
 1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
```

```
      modification such as acetyl or alkoxybenzyl group and/or C-
      terminal modifications such as amide or ester group
<221> NAME/KEY: MOD_RES
<222> LOCATION: (5)
<223> OTHER INFORMATION: Where Xaa is beta,beta-dimethyl cysteine

<400> SEQUENCE: 68

Cys His Ala Val Xaa
 1               5

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence:  Cyclic
      Peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group
<221> NAME/KEY: MOD_RES
<222> LOCATION: (2)
<223> OTHER INFORMATION: Where Xaa is beta,beta-tetramethylene cysteine

<400> SEQUENCE: 69

Ile Xaa Tyr Ser His Ala Val Ser Cys Glu
 1               5                  10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence:  Cyclic
      Peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group
<221> NAME/KEY: MOD_RES
<222> LOCATION: (2)
<223> OTHER INFORMATION: Where Xaa is beta,beta-pentamethylene cysteine

<400> SEQUENCE: 70

Ile Xaa Tyr Ser His Ala Val Ser Ser Cys
 1               5                  10

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group
<221> NAME/KEY: MOD_RES
<222> LOCATION: (1)
<223> OTHER INFORMATION: Where Xaa is beta-mercaptopropionic acid

<400> SEQUENCE: 71

Xaa Tyr Ser His Ala Val Ser Ser Cys
 1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
```

```
<223> OTHER INFORMATION: Cyclic Peptide may comprise N-terminal
      modification such as acetyl or alkoxybenzyl group and/or C-
      terminal modifications such as amide or ester group
<221> NAME/KEY: MOD_RES
<222> LOCATION: (1)
<223> OTHER INFORMATION: Where Xaa is
      beta,beta-pentamethylene-beta-mercaptopropionic acid

<400> SEQUENCE: 72

Xaa Tyr Ser His Ala Val Ser Ser Cys
 1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<221> NAME/KEY: MOD_RES
<222> LOCATION: (4)
<223> OTHER INFORMATION: Where Serine is D-Serine

<400> SEQUENCE: 73

His Ala Val Ser Ser
 1               5

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence:
      Synthesized cyclic peptide

<400> SEQUENCE: 74

Trp Gly Gly Trp
 1

<210> SEQ ID NO 75
<211> LENGTH: 15
<212> TYPE: PRT
<213> ORGANISM: Homo sapiens
<220> FEATURE:
<223> OTHER INFORMATION: Description of Artificial Sequence:
      Representative immunogen containing the HAV
      classical cadherin cell adhesion recognition sequence
<223> OTHER INFORMATION: N-cadherin with HAV cell adhesion recognition
      sequence and flanking amino acids

<400> SEQUENCE: 75

Phe His Leu Arg Ala His Ala Val Asp Ile Asn Gly Asn Gln Val
 1               5                  10                  15

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 76

Cys His Ala Val Asp Ile Asn Gly Cys
 1               5
```

```
<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion recognition sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 77

Ser His Ala Val Asp Ser Ser
  1               5

<210> SEQ ID NO 78
<211> LENGTH: 9
<212> TYPE: PRT
<213> ORGANISM: Unknown
<220> FEATURE:
<223> OTHER INFORMATION: Description of Unknown Organism:  Junction
      adhesion molecule cell adhesion recognition sequence

<400> SEQUENCE: 78

Ser Phe Thr Ile Asp Pro Lys Ser Gly
  1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amide or ester group
<221> NAME/KEY: MOD_RES
<222> LOCATION: (5)
<223> OTHER INFORMATION: Where Xaa is beta,beta-dimethyl cysteine

<400> SEQUENCE: 79

Cys His Ala Val Xaa
  1               5

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amide or ester group
<221> NAME/KEY: MOD_RES
<222> LOCATION: (1)
<223> OTHER INFORMATION: Where Xaa is beta,beta-dimethyl cysteine

<400> SEQUENCE: 80

Xaa His Ala Val Cys
  1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
```

```
      modification such as acetyl or alkoxybenzyl group and/or C-
      terminal modifications such as amide or ester group

<400> SEQUENCE: 81

Cys His Ala Val Pro Cys
  1               5

<210> SEQ ID NO 82
<211> LENGTH: 4
<212> TYPE: PRT
<213> ORGANISM: Unknown
<220> FEATURE:
<223> OTHER INFORMATION: Description of Unknown Organism:  Cadherin
      Calcium Binding Motif
<221> NAME/KEY: VARIANT
<222> LOCATION: (1)...(4)
<223> OTHER INFORMATION: Xaa is any amino acid

<400> SEQUENCE: 82

Xaa Asp Xaa Glu
  1

<210> SEQ ID NO 83
<211> LENGTH: 4
<212> TYPE: PRT
<213> ORGANISM: Unknown
<220> FEATURE:
<223> OTHER INFORMATION: Description of Unknown Organism:  Cadherin
      Calcium Binding Motif

<400> SEQUENCE: 83

Asp Val Asn Glu
  1

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 84

Cys His Ala Val Cys Tyr
  1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 85

Cys Phe Ser His Ala Val Cys
  1               5

<210> SEQ ID NO 86
<211> LENGTH: 8
<212> TYPE: PRT
<213> ORGANISM: Artificial Sequence
<220> FEATURE:
```

```
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 86

Cys Leu Phe Ser His Ala Val Cys
 1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 87

Cys His Ala Val Cys Ser
 1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 88

Ser Cys His Ala Val Cys
 1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amid or ester group

<400> SEQUENCE: 89

Cys His Ala Val Cys Ser Ser
 1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 90

Ser Cys His Ala Val Cys Ser
 1               5
```

```
<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 91

Cys His Ala Val Cys Thr
 1               5

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 92

Cys His Ala Val Cys Glu
 1               5

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 93

Cys His Ala Val Cys Asp
 1               5

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 94

Cys His Ala Val Tyr Cys
 1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amide or ester group
```

-continued

<400> SEQUENCE: 95

His Asn Cys His Ala Val Cys Tyr
 1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or C-
      terminal modifications such as amide or ester group

<400> SEQUENCE: 96

His Asn Cys His Ala Val Cys
 1               5

COMPOUNDS AND METHODS FOR MODULATING ENDOTHELIAL CELL ADHESION

CROSS-REFERENCE TO RELATED APPLICATIONS

This application is a continuation-in-part of U.S. Ser. No. 09/458,870, filed Dec. 10, 1999, now U.S. Pat. No. 6,465, 427, which is a continuation-in-part of U.S. Ser. No. 09/357, 717, filed Jul. 20, 1999, now U.S. Pat. No. 6,471,325, which is a continuation-in-part of U.S. Ser. No. 09/248,074, filed Feb. 10, 1999, now U.S. Pat. No. 6,346,512, which is a continuation-in-part of U.S. Ser. No. 08/996,679, filed Dec. 23, 1997, now U.S. Pat. No. 6,169,071, which is a continuation in part of U.S. Ser. No. 08/893,534, filed Jul. 11, 1997, now U.S. Pat. No. 6,031,072, which claims the benefit of U.S. Provisional Application No. 60/021,612, filed on Jul. 12, 1996.

TECHNICAL FIELD

The present invention relates generally to methods for modulating endothelial cell adhesion, and more particularly to cyclic peptides comprising a cadherin cell adhesion recognition sequence, and to the use of such cyclic peptides for inhibiting or enhancing cadherin-mediated endothelial cell functions, such as cell adhesion.

BACKGROUND OF THE INVENTION

Cell adhesion is a complex process that is important for maintaining tissue integrity and generating physical and permeability barriers within the body. All tissues are divided into discrete compartments, each of which is composed of a specific cell type that adheres to similar cell types. Such adhesion triggers the formation of intercellular junctions (i.e., readily definable contact sites on the surfaces of adjacent cells that are adhering to one another), also known as tight junctions, gap junctions and belt desmosomes. The formation of such junctions gives rise to physical and permeability barriers that restrict the free passage of cells and other biological substances from one tissue compartment to another. For example, the blood vessels of all tissues are composed of endothelial cells. In order for components in the blood to enter a given tissue compartment, they must first pass from the lumen of a blood vessel through the barrier formed by the endothelial cells of that vessel. Similarly, in order for substances to enter the body via the gut, the substances must first pass through a barrier formed by the epithelial cells of that tissue. To enter the blood via the skin, both epithelial and endothelial cell layers must be crossed.

Cell adhesion is mediated by specific cell surface adhesion molecules (CAMs). There are many different families of CAMs, including the immunoglobulin, integrin, selectin and cadherin superfamilies, and each cell type expresses a unique combination of these molecules. Cadherins are a rapidly expanding family of calcium-dependent CAMs (Munro et al., In: *Cell Adhesion and Invasion in Cancer Metastasis*, P. Brodt, ed., pp. 17–34, RG Landes Co. (Austin Tex., 1996). The classical cadherins (abbreviated CADs) are integral membrane glycoproteins that generally promote cell adhesion through homophilic interactions (a CAD on the surface of one cell binds to an identical CAD on the surface of another cell), although CADs also appear to be capable of forming heterotypic complexes with one another under certain circumstances and with lower affinity. Cadherins have been shown to regulate epithelial, endothelial, neural and cancer cell adhesion, with different CADs expressed on different cell types. N (neural)—cadherin is predominantly expressed by neural cells, endothelial cells and a variety of cancer cell types. E (epithelial)—cadherin is predominantly expressed by epithelial cells. Other CADs are P (placental)—cadherin, which is found in human skin and R (retinal)—cadherin. A detailed discussion of the classical cadherins is provided in Munro S B et al., 1996, In: *Cell Adhesion and Invasion in Cancer Metastasis*, P. Brodt, ed., pp.17–34 (RG Landes Company, Austin Tex.).

The structures of the CADs are generally similar. As illustrated in FIG. 1, CADs are composed of five extracellular domains (EC1–EC5), a single hydrophobic domain (TM) that transverses the plasma membrane (PM), and two cytoplasmic domains (CP1 and CP2). The calcium binding motifs DXNDN (SEQ ID NO:9), DXD and LDRE (SEQ ID NO:9) are interspersed throughout the extracellular domains. The first extracellular domain (EC1) contains the classical cadherin cell adhesion recognition (CAR) sequence, HAV (His-Ala-Val), along with flanking sequences on either side of the CAR sequence that may play a role in conferring specificity. Synthetic peptides containing the CAR sequence and antibodies directed against the CAR sequence have been shown to inhibit CAD-dependent processes (Munro et al., supra; Blaschuk et al., *J. Mol. Biol.* 211:679–82, 1990; Blaschuk et al., *Develop. Biol.* 139:227–29, 1990; Alexander et al., *J. Cell. Physiol.* 156:610–18, 1993). The three-dimensional solution and crystal structures of the EC1 domain have been determined (Overduin et al., *Science* 267:386–389, 1995; Shapiro et al., *Nature* 374:327–337, 1995).

Although cell adhesion is required for certain normal physiological functions, there are situations in which cell adhesion is undesirable. For example, many pathologies (such as autoimmune and inflammatory diseases) involve abnormal cellular adhesion. Cell adhesion may also play a role in graft rejection. In such circumstances, modulation of cell adhesion may be desirable.

In addition, permeability barriers arising from cell adhesion create difficulties for the delivery of drugs to specific tissues and tumors within the body. For example, skin patches are a convenient tool for administering drugs through the skin. However, the use of skin patches has been limited to small, hydrophobic molecules because of the epithelial and endothelial cell barriers. Similarly, endothelial cells render the blood capillaries largely impermeable to drugs, and the blood/brain barrier has hampered the targeting of drugs to the central nervous system. In addition, many solid tumors develop internal barriers that limit the delivery of anti-tumor drugs and antibodies to inner cells.

Attempts to facilitate the passage of drugs across such barriers generally rely on specific receptors or carrier proteins that transport molecules across barriers in vivo. However, such methods are often inefficient, due to low endogenous transport rates or to the poor functioning of a carrier protein with drugs. While improved efficiency has been achieved using a variety of chemical agents that disrupt cell adhesion, such agents are typically associated with undesirable side-effects, may require invasive procedures for administration and may result in irreversible effects. It has been suggested that linear synthetic peptides containing a cadherin CAR sequence may be employed for drug transport (WO 91/04745), but such peptides are often metabolically unstable and are generally considered to be poor therapeutic agents.

Accordingly, there is a need in the art for compounds that modulate cell adhesion and improve drug delivery across permeability barriers without such disadvantages. The present invention fulfills this need and further provides other related advantages.

SUMMARY OF THE INVENTION

The present invention provides modulating agents comprising cyclic peptides, and methods for using such agents to inhibit or enhance cadherin-mediated endothelial cell adhesion. Such cyclic peptides generally comprise the sequence His-Ala-Val. Within certain aspects, such cyclic peptides have the formula:

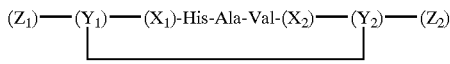

wherein $X_1$, and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; wherein $Y_1$ and $Y_2$ are independently selected from the group consisting of amino acid residues, and wherein a covalent bond is formed between residues $Y_1$ and $Y_2$; and wherein $Z_1$ and $Z_2$ are optional, and if present, are independently selected from the group consisting of amino acid residues and combinations thereof in which the residues are linked by peptide bonds. Such cyclic peptides may comprise modifications such as an N-acetyl or N-alkoxybenzyl group and/or a C-terminal amide or ester group. Cyclic peptides may be cyclized via, for example, a disulfide bond; an amide bond between terminal functional groups, between residue side-chains or between one terminal functional group and one residue side chain; a thioether bond or $\delta_1\delta_1$-ditryptophan, or a derivative thereof.

Within certain embodiments, a cyclic peptide has the formula:

wherein $Y_1$ and $Y_2$ are optional and, if present are independently selected from the group consisting of amino acid residues and combinations thereof in which the residues are linked by peptide bonds, and wherein $Y_1$ and $Y_2$ range in size from 0 to 10 residues; and wherein X and Z are independently selected from the group consisting of amino acid residues, wherein a disulfide bond is formed between residues X and Z; and wherein X has a terminal modification (e.g., an N-acetyl group).

Within further embodiments, a cyclic peptide has the formula:

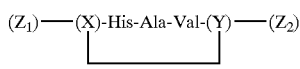

wherein $Z_1$ and $Z_2$ are selected from the group consisting of amino acid residues and combinations thereof in which the residues are linked by peptide bonds, and wherein $Z_1$ and $Z_2$ range in size from 1 to 10 residues; and wherein X and Y are independently selected from the group consisting of amino acid residues, wherein a disulfide bond is formed between residues X and Y; and wherein X has a terminal modification (e.g., an N-acetyl group).

Certain specific cyclic peptides provided by the present invention include N—Ac-CHAVC-NH$_2$ (SEQ ID NO:10), N—Ac-CHAVC-Y—NH$_2$ (SEQ ID NO:10), N—Ac-YCHAVC-NH$_2$ (SEQ ID NO:54), N—Ac-CHAVDC-NH$_2$ (SEQ ID NO:20), N—Ac-CHAVDIC-NH$_2$ (SEQ ID NO:50), N—Ac-CHAVDINC-NH$_2$ (SEQ ID NO:51, N—Ac-CHAVDINGC-NH$_2$ (SEQ ID NO:52), N—Ac-CAHAVC-NH$_2$ (SEQ ID NO:22), N—Ac-CAHAVDC-NH$_2$ (SEQ ID NO:26), N—Ac-CAHAVDIC-NH$_2$ (SEQ ID NO:24), N—Ac-CRAHAVDC-NH$_2$ (SEQ ID NO:28), N—Ac-CLRAHAVC-NH$_2$ (SEQ ID NO:30), N—Ac-CLRAHAVDC-NH$_2$ (SEQ ID NO:32), N—Ac-CSHAVC-NH$_2$ (SEQ ID NO:36), N—Ac-CFSHAVC-NH$_2$ (SEQ ID NO:85), N—Ac-CLFSHAVC-NH$_2$ (SEQ ID NO:86), N—Ac-CHAVSC-NH$_2$ (SEQ ID NO:38), N—Ac-CSHAVSC-NH$_2$ (SEQ ID NO:40), N—Ac-CSHAVSSC-NH$_2$ (SEQ ID NO:42), N—Ac-CHAVSSC-NH$_2$ (SEQ ID NO:44), N—Ac-KHAVD-NH$_2$ (SEQ ID NO:12), N—Ac-DHAVK-NH$_2$ (SEQ ID NO:14), N—Ac-KHAVE-NH$_2$ (SEQ ID NO:16), N—Ac-AHAVDI-NH$_2$ (SEQ ID NO:34), N—Ac-SHAVDSS-NH$_2$ (SEQ ID NO:77), N—Ac-KSHAVSSD-NH$_2$ (SEQ ID NO:48), N—Ac-CHAVC-S-NH$_2$ (SEQ ID NO:87), N—Ac—S-CHAVC-NH$_2$ (SEQ ID NO:88), N—Ac-CHAVC-SS—NH$_2$ (SEQ ID NO:89), N—Ac—S-CHAVC-S—NH$_2$ (SEQ ID NO:90), N—Ac-CHAVC-T—NH$_2$ (SEQ ID NO:91), N—Ac-CHAVC-E—NH$_2$ (SEQ ID NO:92), N—Ac-CHAVC-D—NH$_2$ (SEQ ID NO:93), N—Ac-CHAVYC-NH$_2$ (SEQ ID NO:94), $CH_3$—$SO_2$—HN-CHAVC-Y—NH$_2$ (SEQ ID NO:95), $CH_3$—$SO_2$—HN-CHAVC-NH$_2$ (SEQ ID NO:96), HC(O)—NH-CHAVC-NH$_2$ (SEQ ID NO:96), N—Ac-CHAVPen-NH$_2$ (SEQ ID NO:79), N—Ac-PenHAVC-NH$_2$ (SEQ ID NO:80) and N—Ac-CHAVPC-NH$_2$ (SEQ ID NO:81), as well as derivatives thereof in which the N—Ac group is replaced by a different terminal group. Within further aspects, the present invention provides cell adhesion modulating agents that comprise a cyclic peptide as described above. Within specific embodiments, such modulating agents may be linked to one or more of a targeting agent, a drug, a solid support or support molecule, or a detectable marker. In addition, or alternatively, a cell adhesion modulating agent may further comprising one or more of: (a) a cell adhesion recognition sequence that is bound by an adhesion molecule other than a cadherin, wherein the cell adhesion recognition sequence is separated from any HAV sequence(s) by a linker; and/or (b) an antibody or antigen-binding fragment thereof that specifically binds to a cell adhesion recognition sequence bound by an adhesion molecule other than a cadherin.

The present invention further provides pharmaceutical compositions comprising a cell adhesion modulating agent as described above, in combination with a pharmaceutically acceptable carrier. Such compositions may further comprise a drug. Alternatively, or in addition, such compositions may comprise: (a) a peptide comprising a cell adhesion recognition sequence that is bound by an adhesion molecule other than a cadherin; and/or (b) an antibody or antigen-binding fragment thereof that specifically binds to a cell adhesion recognition sequence bound by an adhesion molecule other than a cadherin.

Within further aspects, methods are provided for modulating endothelial cell adhesion, comprising contacting a cadherin-expressing endothelial cell with a cell adhesion modulating agent as described above. In certain such aspects, the agent inhibits N-cadherin mediated cell adhesion, resulting in the reduction of unwanted endothelial cell adhesion in the mammal.

The present invention also provides, within other aspects, methods for inhibiting angiogenesis in a mammal, comprising administering to a mammal a cell adhesion modulating agent as described above, wherein the modulating agent inhibits endothelial cell adhesion.

Within further aspects, methods are provided for increasing vasopermeability in a mammal, comprising administering to a mammal a cell adhesion modulating agent as described above, wherein the modulating agent inhibits endothelial cell adhesion.

The present invention further provides, within other aspects, methods for increasing blood flow to a tumor, comprising contacting a tumor with a modulating agent as described above, wherein the modulating agent inhibits endothelial cell adhesion.

Methods are also provided, within further aspects, for disrupting neovasculature in a mammal, comprising administering to a mammal a modulating agent as described above, wherein the modulating agent inhibits endothelial cell adhesion.

Within further aspects, methods are provided for inhibiting the development of endometriosis in a mammal, comprising administering to a mammal a modulating agent as described above, wherein the agent inhibits endothelial cell adhesion.

These and other aspects of the invention will become evident upon reference to the following detailed description and attached drawings. All references disclosed herein are hereby incorporated by reference in their entirety as if each were individually noted for incorporation.

BRIEF DESCRIPTION OF THE DRAWINGS

FIG. 2 provides the amino acid sequences of mammalian classical cadherin EC1 domains: human N-cadherin (SEQ ID NO:1), mouse N-cadherin (SEQ ID NO:2), cow N-cadherin (SEQ ID NO:3), human P-cadherin (SEQ ID NO:4), mouse P-cadherin (SEQ ID NO:5), human E-cadherin (SEQ ID NO:6) and mouse E-cadherin (SEQ ID NO:7).

FIGS. 3A–3I provides the structures of representative cyclic peptides of the present invention (structures on the left hand side; SEQ ID NOs:10, 12, 14, 16, 18, 20, 22, 24, 26, 28, 30, 32, 34, 36, 38, 40, 42, 44, 46, 48), along with similar, but iN-Active, structures (on the right; SEQ ID NOs:11, 13, 15, 17, 19, 21, 23, 25, 27, 29, 31, 33, 35, 37, 39, 41, 43, 45, 47, 49).

FIG. 5A shows the cells 30 minutes after exposure to 500 μg/mL N—Ac-CHAVC-NH$_2$ (SEQ ID NO:10). FIG. 5B shows the cells 30 minutes after exposure to the control peptide N—Ac-CHGVC-NH$_2$ (SEQ ID NO:11). FIG. 5C shows the cells in the absence of cyclic peptide. Note that the endothelial cells retracted from one another in the presence of N—Ac-CHAVC-NH$_2$ (SEQ ID NO:10).

FIG. 6A shows the cells 30 minutes after exposure to 500 μg/mL N—Ac-CAHAVDIC-NH$_2$ (SEQ ID NO:24). FIG. 6B shows the cells 30 minutes after exposure to the control peptide N—Ac-CAHGVDIC-NH$_2$ (SEQ ID NO:25). FIG. 6C shows the cells in the absence of cyclic peptide. In this case, neither of the cyclic peptides show activity.

FIG. 7A shows the cells 30 minutes after exposure to 500 μg/mL N—Ac-CAHAVDC-NH$_2$ (SEQ ID NO:26). FIG. 7B shows the cells 30 minutes after exposure to the control peptide N—Ac-CAHGVDC-NH$_2$ (SEQ ID NO:27). FIG. 7C shows the cells in the absence of cyclic peptide. Note that the endothelial cells retracted from one another in the presence of N—Ac-CAHAVDC-NH$_2$ (SEQ ID NO:26).

FIG. 8A shows the cells 30 minutes after exposure to 500 μg/mL N—Ac-CSHAVSSC-NH$_2$ (SEQ ID NO:42). FIG. 8B shows the cells 30 minutes after exposure to the control peptide N—Ac-CSHGVSSC-NH$_2$ (SEQ ID NO:43). FIG. 8C shows the cells in the absence of cyclic peptide. Note that the endothelial cells retracted from one another and round up in the presence of N—Ac-CSHAVSSC-NH$_2$ (SEQ ID NO:42).]

DETAILED DESCRIPTION OF THE INVENTION

Figure 1:
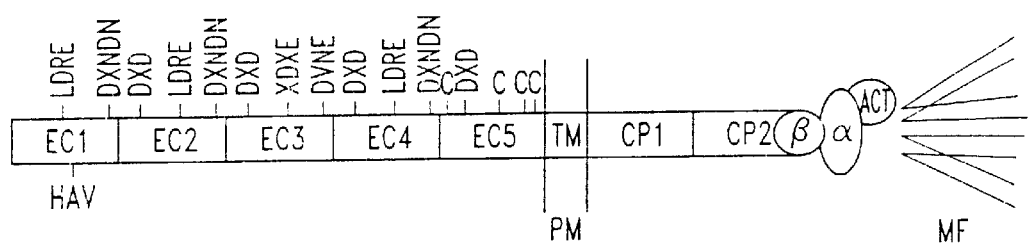
FIG. 1 is a diagram depicting the structure of classical CADs. The five extracellular domains are designated EC1–EC5, the hydrophobic domain that transverses the plasma membrane (PM) is represented by TM, and the two cytoplasmic domains are represented by CP1 and CP2. The calcium binding motifs are shown by DXNDN (SEQ ID NO:9), DXD, LDRE (SEQ ID NO:9), XDXE (SEQ ID NO:82) and DVNE (SEQ ID NO:83). The CAR sequence, HAV, is shown within EC1. Cytoplasmic proteins β-catenin (β), α-catenin (α) and α-actinin (ACT), which mediate the interaction between CADs and microfilaments (MF) are also shown.
Figure 4:
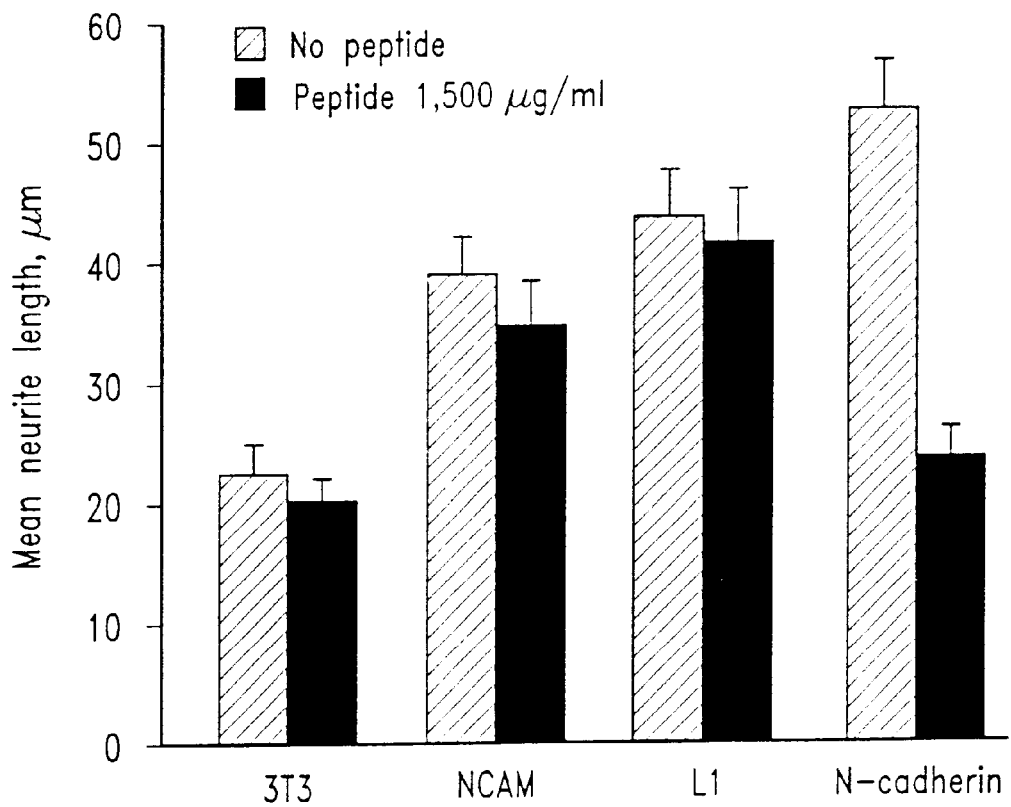
FIG. 4 is a histogram depicting the mean neurite length in microns for neurons grown in the presence (solid bars) or absence (cross-hatched bars) of 500 μg/mL of the representative cyclic peptide N—Ac-CHAVC-NH$_2$ (SEQ ID NO:10). In the first pair of bars, neurons were grown on a monolayer of untransfected 3T3 cells. In the remaining columns, the mean neurite length is shown for neurons cultured on 3T3 cells transfected with cDNA encoding N-CAM (second pair of bars), L1 (third pair of bars) or N-cadherin (fourth pair of bars).

As noted above, the present invention provides cell adhesion modulating agents comprising cyclic peptides that are capable of modulating classical cadherin-mediated processes, such as endothelial cell adhesion. Cyclic peptides provided herein generally comprise the classical cadherin cell adhesion recognition (CAR) sequence HAV (i.e., His-Ala-Val) within the cyclized portion of the peptide (i.e., within the peptide ring). Certain modulating agents described herein inhibit cell adhesion. Such modulating agents may generally be used, for example, to treat diseases or other conditions characterized by undesirable endothelial cell adhesion or to inhibit angiogenesis or increase vasopermeability.

Cyclic Peptides

The term "cyclic peptide," as used herein, refers to a peptide or salt thereof that comprises (1) an intramolecular covalent bond between two non-adjacent residues and (2) at least one classical cadherin cell adhesion recognition (CAR) sequence HAV (His-Ala-Val). The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds. In addition to the classical cadherin CAR sequence HAV, a modulating agent may comprise additional CAR sequences, which may or may not be cadherin CAR sequences, and/or antibodies or fragments thereof that specifically recognize a CAR sequence. Additional CAR sequences may be present within the cyclic peptide containing the HAV sequence, within a separate cyclic peptide component of the modulating agent and/or in a non-cyclic portion of the modulating agent. Antibodies and antigen-binding fragments thereof are typically present in a non-cyclic portion of the modulating agent.

Certain preferred cyclic peptides satisfy the formula:

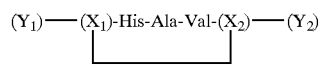

wherein $X_1$, and $X_2$ are independently selected from the group consisting of amino acid residues, with a covalent bond formed between residues $X_1$ and $X_2$; and wherein $Y_1$ and $Y_2$ are optional and, if present, are independently selected from the group consisting of amino acid residues and combinations thereof in which the residues are linked by peptide bonds.

Certain specific cyclic peptides also satisfy the formula:

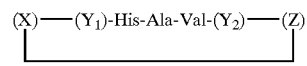

wherein $Y_1$ and $Y_2$ are optional and, if present are independently selected from the group consisting of amino acid residues and combinations thereof in which the residues are linked by peptide bonds, and wherein $Y_1$ and $Y_2$ range in size from 0 to 10 residues; and wherein X and Z are independently selected from the group consisting of amino acid residues, wherein a disulfide bond is formed between residues X and Z; and wherein X has a terminal modification (e.g., an N-acetyl group).

Other cyclic peptides have the formula:

wherein $Z_1$ and $Z_2$ are selected from the group consisting of amino acid residues and combinations thereof in which the residues are linked by peptide bonds, and wherein $Z_1$ and $Z_2$ range in size from 1 to 10 residues; and wherein X and Y are independently selected from the group consisting of amino acid residues, wherein a disulfide bond is formed between residues X and Y; and wherein X has a terminal modification (e.g., an N-acetyl group).

Within certain embodiments, a cyclic peptide preferably comprises an N-acetyl group (i.e., the amino group present on the amino terminal residue of the peptide prior to cyclization is acetylated) or an N-formyl group (i.e., the amino group present on the amino terminal residue of the peptide prior to cyclization is formylated), or the amino group present on the amino terminal residue of the peptide prior to cyclization is mesylated. It has been found, within the context of the present invention, that the presence of such terminal groups may enhance cyclic peptide activity for certain applications. One particularly preferred cyclic peptide is N—Ac-CHAVC-NH$_2$ (SEQ ID NO:10). Another preferred cyclic peptide is N—Ac-CHAVC-Y—NH$_2$ (SEQ ID NO:84). Other cyclic peptides include, but are not limited to: N—Ac-CHAVDC-NH$_2$ (SEQ ID NO:20), N—Ac-CHAVDIC-NH$_2$ (SEQ ID NO:50), N—Ac-CHAVDINC-NH$_2$ (SEQ ID NO:51), N—Ac-CHAVDINGC-NH$_2$ (SEQ ID NO:76), N—Ac-CAHAVC-NH$_2$ (SEQ ID NO:22), N—Ac-CAHAVDC-NH$_2$ (SEQ ID NO:26), N—Ac-CAHAVDIC-NH$_2$ (SEQ ID NO:24), N—Ac-CRAHAVDC-NH$_2$ (SEQ ID NO:28), N—Ac-CLRAHAVC-NH$_2$ (SEQ ID NO:30), N—Ac-CLRAHAVDC-NH$_2$ (SEQ ID NO:32), N—Ac-CSHAVC-NH$_2$ (SEQ ID NO:36), N—Ac-CFSHAVC-NH$_2$ (SEQ ID NO:85), N—Ac-CLFSHAVC-NH$_2$ (SEQ ID NO:86), N—Ac-CHAVSC-NH$_2$ (SEQ ID NO:38), N—Ac- CSHAVSC-NH$_2$ (SEQ ID NO:40), N—Ac-CSHAVSSC-NH$_2$ (SEQ ID NO:42), N—Ac-CHAVSSC-NH$_2$ (SEQ ID NO:44), N—Ac-KHAVD-NH$_2$ (SEQ ID NO: 12), N—Ac-DHAVK-NH$_2$ (SEQ ID NO: 14), N—Ac-KHAVE-NH$_2$ (SEQ ID NO:16), N—Ac-AHAVDI-NH$_2$ (SEQ ID NO:34), N—Ac-SHAVDSS-NH$_2$ (SEQ ID NO:77), N—Ac-KSHAVSSD-NH$_2$ (SEQ ID NO:48), N—Ac-CHAVC-S—NH$_2$ (SEQ ID NO:87), N—Ac—S-CHAVC-NH$_2$ (SEQ ID NO:88), N—Ac-CHAVC-SS—NH$_2$ (SEQ ID NO:89), N—Ac—S-CHAVC-S—NH$_2$ (SEQ ID NO:90), N—Ac-CHAVC-T—NH$_2$ (SEQ ID NO:91), N—Ac-CHAVC-E—NH$_2$ (SEQ ID NO:92), N—Ac-CHAVC-D—NH$_2$ (SEQ ID NO:93), N—Ac-CHAVYC-NH$_2$ (SEQ ID NO:94), CH$_3$—SO$_2$—HN-CHAVC-Y—NH$_2$ (SEQ ID NO:95), N—Ac—Y-CHAVC-NH$_2$, (SEQ ID NO:54), CH$_3$—SO$_2$—HN-CHAVC-NH$_2$ (SEQ ID NO:96), HC(O)—NH-CHAVC-NH$_2$ (SEQ ID NO:96), N—Ac-CHAVPen-NH$_2$ (SEQ ID NO:79), N—Ac-PenHAVC-NH$_2$ (SEQ ID NO:80) and N—Ac-CHAVPC-NH$_2$ (SEQ ID NO:81).

In addition to the CAR sequence(s), cyclic peptides generally comprise at least.one additional residue, such that the size of the cyclic peptide ring ranges from 4 to about 15 residues, preferably from 5 to 10 residues. Such additional residue(s) may be present on the N-terminal and/or C-terminal side of a CAR sequence, and may be derived from sequences that flank the HAV sequence within one or more naturally occurring cadherins (e.g., N-cadherin, E-cadherin, P-cadherin, R-cadherin or other cadherins containing the HAV sequence) with or without amino acid substitutions and/or other modifications. Flanking sequences for endogenous N-, E-, P- and R-caherin are shown in FIG. 2, and in SEQ ID NOs:1 to 7. Database accession numbers for representative naturally occurring cadherins are as follows: human N-cadherin M34064, mouse N-cadherin M31131 and M22556, cow N-cadherin X53615, human P-cadherin X63629, mouse P-cadherin X06340, human E-cadherin Z13009, mouse E-cadherin X06115. Alternatively, additional residues present on one or both sides of the CAR sequence(s) may be unrelated to an endogenous sequence (e.g., residues that facilitate cyclization). Preferred flanking sequences are derived from a native N-cadherin sequence.

Within certain preferred embodiments, as discussed below, relatively small cyclic peptides that do not contain significant sequences flanking the HAV sequence are preferred for modulating N-cadherin mediated cell adhesion. Such peptides may contain an N-acetyl group and a C-amide group (e.g., the 5-residue rings N—Ac-CHAVC-$NH_2$ (SEQ ID NO:10), N—Ac-KHAVD-$NH_2$ (SEQ ID NO:12), H—C(O)-CHAVC-$NH_2$ (SEQ ID NO:10)or $CH_3$—$SO_2$—NH-CHAVC-$NH_2$ (SEQ ID NO:96)). The finding, within the present invention, that such relatively small cyclic peptides may be effective and all-purpose inhibitors of cell adhesion represents a unexpected discovery. Such cyclic peptides can be thought of as "master keys" that fit into peptide binding sites of each of the different classical cadherins, and are capable of disrupting cell adhesion of, for example, endothelial cells. Small cyclic peptides may generally be used to specifically modulate cell adhesion of endothelial and/or other cell types by topical administration or by systemic administration, with or without linking a targeting agent to the peptide, as discussed below.

Within other preferred embodiments, a cyclic peptide may contain sequences that flank the HAV sequence on one or both sides that are designed to confer specificity for cell adhesion mediated by one or more specific cadherins, resulting in tissue and/or cell-type specificity. Suitable flanking sequences for conferring specificity include, but are not limited to, endogenous sequences present in one or more naturally occurring cadherins, and cyclic peptides having specificity may be identified using the representative screens provided herein. For example, it has been found, within the context of the present invention, that cyclic peptides that contain additional residues derived from the native N-cadherin sequence on the N-terminal side of the CAR sequence are specific for cells that express N-cadherin, such as endothelial cells (i.e., such peptides disrupt N-cadherin mediated cell adhesion to a greater extent than they disrupt E-cadherin expression). Further, the addition of one or more amino acid residues on the C-terminal side of the HAV sequence in an endogenous N-cadherin results in cyclic peptides that are potent inhibitors of endothelial cell adhesion.

To facilitate the preparation of cyclic peptides having a desired specificity, nuclear magnetic resonance (NMR) and computational techniques may be used to determine the conformation of a peptide that confers a known specificity. NMR is widely used for structural analysis of molecules. Cross-peak intensities in nuclear Overhauser enhancement (NOE) spectra, coupling constants and chemical shifts depend on the conformation of a compound. NOE data provide the interproton distance between protons through space and across the ring of the cyclic peptide. This information may be used to facilitate calculation of the low energy conformations for the HAV sequence. Conformation may then be correlated with tissue specificity to permit the identification of peptides that are similarly tissue specific or have enhanced tissue specificity.

Cyclic peptides as described herein may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations indicated in Table 1, and the corresponding D-amino acids are designated by a lower case one letter symbol. Modulating agents and cyclic peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a cyclic peptide include, but are not limited to, penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline, ornithine, diaminobutyric acid, α-aminoadipic acid, m-aminomethylbenzoic acid and α,β-diaminopropionic acid.

TABLE 1

Amino acid one-letter and three-letter abbreviations

| | | |
|---|---|---|
| A | Ala | Alanine |
| R | Arg | Arginine |
| D | Asp | Aspartic acid |
| N | Asn | Asparagine |
| C | Cys | Cysteine |
| Q | Gln | Glutamine |
| E | Glu | Glutamic acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |

Cyclic peptides as described herein may be synthesized by methods well known in the art, including recombinant DNA methods and chemical synthesis. Chemical synthesis may generally be performed using standard solution phase or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solid phase and solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., J. Am. Chem. Soc. 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of is acidolytic cleavage. Orthogonal systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminal can be accomplished by reacting the final peptide with acetic anhydride before cleavage from the resin. C-amidation is accomplished using an appropriate resin such as methylbenzhydrylamine resin using the Boc technology.

Following synthesis of a linear peptide, with or without N-acetylation and/or C-amidation, cyclization may be achieved by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. By way of example, strong oxidizing agents can be used to perform the cyclization shown below (SEQ ID NOs:62 and 63), in which the underlined portion is cyclized:

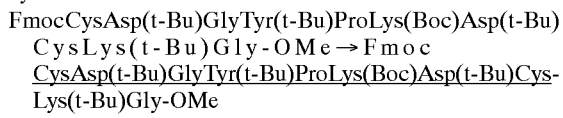

Oxidizing agents also allow concurrent deprotection/oxidation of suitable S-protected linear precursors to avoid premature, nonspecific oxidation of free cysteine, as shown below (SEQ ID NOs:64 and 65), where X and Y=S-Trt or S-Acm:

BocCys(X)GlyAsnLeuSer(t-Bu)Thr(t-Bu)Cys(Y)MetLeuGlyOH→Boc <u>CysGlyAsnLeuSer(t-Bu)Thr(t-Bu)Cys</u>MetLeuGlyOH

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. In the example below (SEQ ID NOs:66 and 67), X is Acm, Tacm or t-Bu:

H-Cys(X)TyrIleGlnAsnCys(X)ProLeuGly-NH$_2$→H-<u>CysTyrIleGlnAsnCys</u>ProLeuGly-NH$_2$

Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β,β-mercaptopropionic acid (Mpr), β,β-pentamethylene-β-mercaptopropionic acid (Pmp), 2-mercaptobenzene, 2-mercaptoaniline and 2-mercaptoproline. Peptides containing such residues are illustrated by the following representative formulas, in which the underlined portion is cyclized, N-acetyl groups are indicated by N—Ac and C-terminal amide groups are represented by —NH$_2$:

i) N—Ac-<u>Cys-His-Ala-Val-Cys</u>-NH$_2$ (SEQ ID NO:10)

ii) N—Ac-<u>Cys-Ala-His-Ala-Val-Asp-Ile-Cys</u>-NH$_2$ (SEQ ID NO:24)

iii) N—Ac-<u>Cys-Ser-His-Ala-Val-Cys</u>-NH$_2$ (SEQ ID NO:36)

iv) N—Ac-<u>Cys-His-Ala-Val-Ser-Cys</u>-NH$_2$ (SEQ ID NO:38)

v) N—Ac-<u>Cys-Ala-His-Ala-Val-Asp-Cys</u>-NH$_2$ (SEQ ID NO:26)

vi) N—Ac-<u>Cys-Ser-His-Ala-Val-Ser-Ser-Cys</u>-NH$_2$ (SEQ ID NO:42)

vii) N—Ac-<u>Cys-His-Ala-Val-Ser-Cys</u>-OH (SEQ ID NO:38)

viii) H-<u>Cys-Ala-His-Ala-Val-Asp-Cys</u>-NH$_2$ (SEQ ID NO:26)

ix) N—Ac-<u>Cys-His-Ala-Val-Pen</u>-NH$_2$ (SEQ ID NO:68)

x) N—Ac-Ile-<u>Tmc-Tyr-Ser-His-Ala-Val-Ser-Cys</u>-Glu-NH$_2$ (SEQ ID NO:69)

xi) N—Ac-Ile-<u>Pmc-Tyr-Ser-His-Ala-Val-Ser-Ser-Cys</u>-NH$_2$ (SEQ ID NO:70)

xii) <u>Mpr-Tyr-Ser-His-Ala-Val-Ser-Ser-Cys</u>-NH$_2$ (SEQ ID NO:71)

xiii) <u>Pmp-Tyr-Ser-His-Ala-Val-Ser-Ser-Cys</u>-NH$_2$ (SEQ ID NO:72)

xii)

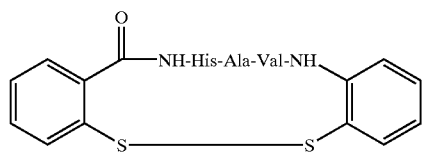

xiii)

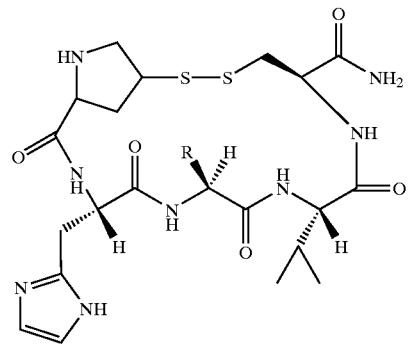

It will be readily apparent to those of ordinary skill in the art that, within each of these representative formulas, any of the above thiol-containing residues may be employed in place of one or both of the thiol-containing residues recited.

Within another embodiment, cyclization may be achieved by amide bond formation. For example, a peptide bond may be formed between terminal functional groups (i.e., the amino and carboxy termini of a linear peptide prior to cyclization). Two such cyclic peptides are <u>AHAVDI</u> (SEQ ID NO:34) and <u>SHAVSS</u> (SEQ ID NO:46), with or without an N-terminal acetyl group and/or a C-terminal amide. Within another such embodiment, the peptide comprises a D-amino acid (e.g., <u>HAVsS</u>; SEQ ID NO:73). Alternatively, cyclization may be accomplished by linking one terminus and a residue side chain or using two side chains, as in <u>KHAVD</u> (SEQ ID NO:12) or <u>KSHAVSSD</u> (SEQ ID NO:48), with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the iN-Active N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris(dimethylamino) phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

i.

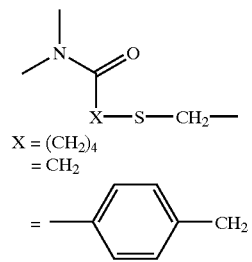

ii.

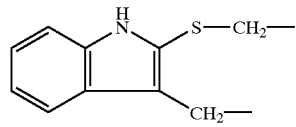

Cyclization may also be achieved using δ₁,δ₁'-Ditryptophan (i.e., Ac-<u>Trp-Gly-Gly-Trp</u>-OMe) (SEQ ID NO:74), as shown below:

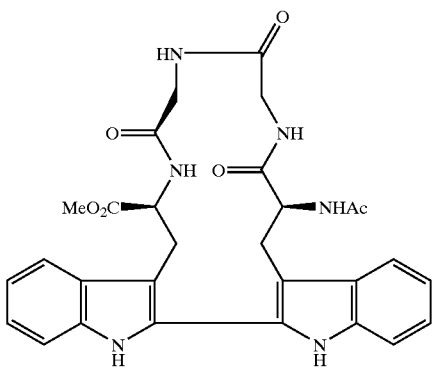

Representative structures of cyclic peptides are provided in FIG. 3. Within FIG. 3, certain cyclic peptides having the ability to modulate cell adhesion (shown on the left) are paired with similar iN-Active structures (on the right). The structures and formulas recited herein are provided solely for the purpose of illustration, and are not intended to limit the scope of the cyclic peptides described herein.

Cell Adhesion Modulating Agents

The term "cell adhesion modulating agent," as used herein, refers to a molecule comprising at least one cyclic peptide that contains the classical cadherin cell adhesion recognition (CAR) sequence HAV (His-Ala-Val), as described above. As noted above, multiple CAR sequences may be present within a modulating agent. Further, additional CAR sequences (i.e., any sequences specifically bound by an adhesion molecule) may be included within a modulating agent. As used herein, an "adhesion molecule" is any molecule that mediates cell adhesion via a receptor on the cell's surface. Adhesion molecules include members of the cadherin gene superfamily that are not classical cadherins (e.g., proteins that do not contain an HAV sequence and/or one or more of the other characteristics recited above for classical cadherins), such as desmogleins (Dsg) and desmocollins (Dsc); integrins; members of the immunoglobulin supergene family, such as N-CAM; and other uncategorized transmembrane proteins, such as occludin, as well as extracellular matrix proteins such as laminin, fibronectin, collagens, vitronectin, entactin and tenascin. Preferred CAR sequences for inclusion within a modulating agent include (a) Arg-Gly-Asp (RGD), which is bound by integrins (see Cardarelli et al., *J. Biol. Chem.* 267:23159–64, 1992); (b) Tyr-Ile-Gly-Ser-Arg (YIGSR; SEQ ID NO:52), which is bound by α6β1 integrin; (c) KYSFNYDGSE (SEQ ID NO:53), which is bound by N-CAM; (d) the junctional adhesion molecule (JAM; see Martin-Padura et al., *J. Cell. Biol.* 142:117–127, 1998) CAR sequence SFTIDPKSG (SEQ ID NO:78) or DPK; (e) the occludin CAR sequence LYHY (SEQ ID NO:55); (f) claudin CAR sequences comprising at least four consecutive amino acids present within a claudin region that has the formula: Trp-Lys/Arg-Aaa-Baa-Ser/Ala-Tyr/Phe-Caa-Gly (SEQ ID NO:56), wherein Aaa, Baa and Caa indicate independently selected amino acid residues; Lys/Arg is an amino acid that is lysine or arginine; Ser/Ala is an amino acid that is serine or alanine; and Tyr/Phe is an amino acid that is tyrosine or phenylalanine; and (g) nonclassical cadherin CAR sequences comprising at least three consecutive amino acids present within a non-classical cadherin region that has the formula: Aaa-Phe-Baa- Ile/Leu/Val-Asp/Asn/Glu-Caa-Daa-Ser/Thr/Asn-Gly (SEQ ID NO:57), wherein Aaa, Baa, Caa and Daa are independently selected amino acid residues; Ile/Leu/Val is an amino acid that is selected from the group consisting of isoleucine, leucine and valine, Asp/Asn/Glu is an amino acid that is selected from the group consisting of aspartate, asparagine and glutamate; and Ser/Thr/Asn is an amino acid that is selected from the group consisting of serine, threonine or asparagine. Representative claudin CAR sequences include IYSY (SEQ ID NO:58), TSSY (SEQ ID NO:59), VTAF (SEQ ID NO:60) and VSAF (SEQ ID NO:61). Representative nonclassical cadherin CAR sequences include the VE-cadherin (cadherin-5) CAR sequence DAE.

Linkers may, but need not, be used to separate CAR sequences and/or antibody sequences within a modulating agent. Linkers may also, or alternatively, be used to attach one or more modulating agents to a support molecule or material, as described below. A linker may be any molecule (including peptide and/or non-peptide sequences as well as single amino acids or other molecules), that does not contain a CAR sequence and that can be covalently linked to at least two peptide sequences. Using a linker, HAV-containing cyclic peptides and other peptide or protein sequences may be joined head-to-tail (i.e., the linker may be covalently attached to the carboxyl or amino group of each peptide sequence), head-to-side chain and/or tail-to-side chain. Modulating agents comprising one or more linkers may form linear or branched structures. Within one embodiment, modulating agents having a branched structure comprise three different CAR sequences, such as RGD, YIGSR (SEQ ID NO:52) and HAV, one or more of which are present within a cyclic peptide. Within another embodiment, modulating agents having a branched structure comprise RGD, YIGSR (SEQ ID NO:52), HAV and KYSFNYDGSE (SEQ ID NO:53). In a third embodiment, modulating agents having a branched structure comprise HAV and LYHY (SEQ ID NO:55), along with one or more of NQK, NRN, NKD, EKD and ERD. Bi-functional modulating agents that comprise an HAV sequence with flanking E-cadherin-specific sequences joined via a linker to an HAV sequence with flanking N-cadherin-specific sequences are also preferred for certain embodiments.

Linkers preferably produce a distance between CAR sequences between 0.1 to 10,000 nm, more preferably about 0.1–400 nm. A separation distance between recognition sites may generally be determined according to the desired function of the modulating agent. For inhibitors of cell adhesion, the linker distance should be small (0.1–400 nm). For enhancers of cell adhesion, the linker distance should be 400–10,000 nm. One linker that can be used for such purposes is $(H_2N(CH_2)_nCO_2H)_m$, or derivatives thereof, where n ranges from 1 to 10 and m ranges from 1 to 4000. For example, if glycine ($H_2NCH_2CO_2H$) or a multimer thereof is used as a linker, each glycine unit corresponds to a linking distance of 2.45 angstroms, or 0.245 nm, as determined by calculation of its lowest energy conformation when linked to other amino acids using molecular modeling techniques. Similarly, aminopropanoic acid corresponds to a linking distance of 3.73 angstroms, aminobutanoic acid to 4.96 angstroms, aminopentanoic acid to 6.30 angstroms and amino hexanoic acid to 6.12 angstroms. Other linkers that may be used will be apparent to those of ordinary skill in the art and include, for example, linkers based on repeat units of 2,3-diaminopropanoic acid, lysine and/or ornithine. 2,3-Diaminopropanoic acid can provide a linking distance of either 2.51 or 3.11 angstroms depending on whether the side-chain amino or terminal amino is used in the linkage. Similarly, lysine can provide linking distances of either 2.44 or 6.95 angstroms and ornithine 2.44 or 5.61 angstroms. Peptide and non-peptide linkers may generally be incorporated into a modulating agent using any appropriate method known in the art.

Modulating agents that inhibit cell adhesion may contain one or more HAV sequences, provided that such sequences are adjacent to one another (i.e., without intervening sequences) or in close proximity (i.e., separated by peptide and/or non-peptide linkers to give a distance between the CAR sequences that ranges from about 0.1 to 400 nm). It will be apparent that other CAR sequences, as discussed above, may also be included. Such modulating agents may generally be used within methods in which it is desirable to simultaneously disrupt cell adhesion mediated by multiple adhesion molecules. Within certain preferred embodiments, an additional CAR sequence is derived from fibronectin and is recognized by an integrin (i.e., RGD; see Cardarelli et al., *J. Biol. Chem.* 267:23159–23164, 1992), or is an occludin CAR sequence (e.g., LYHY; SEQ ID NO:55). One or more antibodies, or fragments thereof, may similarly be used within such embodiments.

Modulating agents that enhance cell adhesion may contain multiple HAV sequences and/or antibodies that specifically bind to an HAV sequence, joined by linkers as described above. Enhancement of cell adhesion may also be achieved by attachment of multiple modulating agents to a support molecule or material, as discussed further below. Such modulating agents may additionally comprise one or more CAR sequence for one or more different adhesion molecules (including, but not limited to, other CAMs) and/or one or more antibodies or fragments thereof that bind to such sequences, to enhance cell adhesion mediated by multiple adhesion molecules.

As noted above, a modulating agent may consist entirely of one or more cyclic peptides, or may contain additional peptide and/or non-peptide sequences. Peptide portions may be synthesized as described above or may be prepared using recombinant methods. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous cadherin or other adhesion molecule. Such sequences may be prepared based on known cDNA or genomic sequences (see Blaschuk et al., *J. Mol. Biol.* 211:679–682, 1990), or from sequences isolated by screening an appropriate library with probes designed based on the sequences of known cadherins. Such screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a peptide portion of a modulating agent, an endogenous sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well known techniques, and then ligated together to form a sequence encoding a portion of the modulating agent.

As noted above, portions of a modulating agent may comprise an antibody, or antigen-binding fragment thereof, that specifically binds to a CAR sequence. As used herein, an antibody, or antigen-binding fragment thereof, is said to "specifically bind" to a CAR sequence (with or without flanking amino acids) if it reacts at a detectable level (within, for example, an ELISA, as described by Newton et al., *Develop. Dynamics* 197:1–13, 1993) with a peptide containing that sequence, and does not react detectably with peptides containing a different CAR sequence or a sequence in which the order of amino acid residues in the cadherin CAR sequence and/or flanking sequence is altered.

Antibodies and fragments thereof may be prepared using standard techniques. See, e.g., Harlow and Lane, *Antibodies: A Laboratory Manual*, Cold Spring Harbor Laboratory, 1988. In one such technique, an immunogen comprising a CAR sequence is initially injected into any of a wide variety of mammals (e.g., mice, rats, rabbits, sheep or goats). Small immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the modulating agent or antigenic portion thereof coupled to a suitable solid support.

Monoclonal antibodies specific for a CAR sequence may be prepared, for example, using the technique of Kohler and Milstein, *Eur. J. Immunol.* 6:51 1–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction. Antibodies having the desired activity may generally be identified using immunofluorescence analyses of tissue sections, cell or other samples where the target cadherin is localized.

Within certain embodiments, monoclonal antibodies may be specific for particular cadherins (e.g., the antibodies bind to N-cadherin, but do not bind significantly to E-cadherin, or vise versa). Such antibodies may be prepared as described above, using an immunogen that comprises (in addition to the HAV sequence) sufficient flanking sequence to generate the desired specificity (e.g., 5 amino acids on each side is generally sufficient). One representative immunogen is the 1 5-mer FHLRAHAVDINGNQV-NH$_2$ (SEQ ID NO:75), linked to KLH (see Newton et al., *Dev. Dynamics* 197:1–13, 1993). To evaluate the specificity of a particular antibody, representative assays as described herein and/or conventional antigen-binding assays may be employed. Such antibodies may generally be used for therapeutic, diagnostic and assay purposes, as described herein. For example, such antibodies may be linked to a drug and administered to a mammal to target the drug to a particular cadherin-expressing cell, such as a leukemic cell in the blood.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628–29).

Evaluation of Modulating Agent Activity

As noted above, cyclic peptides and other modulating agents as described herein are capable of modulating (i.e., enhancing or inhibiting) cadherin-mediated endothelial cell adhesion. The ability of a modulating agent to modulate endothelial cell adhesion may generally be evaluated in vitro using any assay that determines the effect on adhesion between endothelial cells. In general, a modulating agent is an inhibitor of epithelial cell adhesion if, within one or more of such assays, contact of the test cells with the modulating agent results in a discernible disruption of cell adhesion.

Within one representative cell adhesion assay, the addition of a modulating agent to cells that express N-cadherin results in disruption of cell adhesion. An "N-cadherin-expressing cell," as used herein, may be any type of cell that expresses N-cadherin on the cell surface at a detectable level, using standard techniques such as immunocytochemical protocols (Blaschuk and Farookhi, *Dev. Biol.* 136:564–567, 1989). N-cadherin-expressing cells include endothelial cells (e.g., bovine pulmonary artery endothelial cells). For example, such cells may be plated under standard conditions that permit cell adhesion in the presence and absence of modulating agent (e.g., 500 µg/mL). Disruption of cell adhesion may be determined visually within 24 hours, by observing retraction of the cells from one another.

For use within one such assay, bovine pulmonary artery endothelial cells may be harvested by sterile ablation and digestion in 0.1% collagenase (type II; Worthington Enzymes, Freehold, N.J.). Cells may be maintained in Dulbecco's minimum essential medium supplemented with 10% fetal calf serum and 1% antibiotic-antimycotic at 37° C. in 7% $CO_2$ in air. Cultures may be passaged weekly in trypsin-EDTA and seeded onto tissue culture plastic at 20,000 cells/cm$^2$. Endothelial cultures may be used at 1 week in culture, which is approximately 3 days after culture confluency is established. The cells may be seeded onto coverslips and treated (e.g., for 30 minutes) with modulating agent or a control compound at, for example, 500 µg/ml and then fixed with 1% paraformaldehyde. As noted above, disruption of cell adhesion may be determined visually within 24 hours, by observing retraction of the cells from one another. This assay evaluates the effect of a modulating agent on N-cadherin mediated cell adhesion.

A third cell adhesion assay evaluates the ability of a modulating agent to block angiogenesis (the growth of blood vessels from pre-existing blood vessels). This ability may be assayed using the chick chorioallantoic membrane assay described by Iruela-Arispe et al., *Molecular Biology of the Cell* 6:327–343, 1995. Briefly, a modulating agent may be embedded in a mesh composed of vitrogen at one or more concentrations (e.g., ranging from about 1 to 100 µg/mesh).

The mesh(es) may then be applied to chick chorioallantoic membranes. After 24 hours, the effect of the peptide may be determined using computer assisted morphometric analysis. A modulating agent should inhibit angiogenesis by at least 25% at a concentration of 33 μg/mesh.

Alternatively, an agent may be evaluated in vivo by assessing the effect on vascular permeability utilizing the Miles assay (McClure et al., *J. Pharmacological & Toxicological Methods* 32:49–52, 1994). Briefly, a candidate modulating agent may be dissolved in phosphate buffered saline (PBS) at a concentration of 100 μg/ml. Adult rats may be given 100 μl subdermal injections of each peptide solution into their shaved backs, followed 15 minutes later by a single 250 μl injection of 1% Evans blue dissolved in PBS into their tail veins. The subdermal injection sites may be visually monitored for the appearance of blue dye. Once the dye appears (about 15 minutes after injection), each subdermal injection site may be excised, weighed, and placed in 1 ml dimethylformamide for 24 hours to extract the dye. The optical density of the dye extracts may then be determined at 620 nm. In general, the injection of 0.1 ml of modulating agent (at a concentration of 0.1 mg/ml) into the backs of rats causes an increase of dye accumulation at the injection sites of at least 50%, as compared to dye accumulation at sites into which PBS has been injected.

Modulating Agent Modification and Formulations

A modulating agent as described herein may, but need not, be linked to one or more additional molecules. In particular, as discussed below, it may be beneficial for certain applications to link multiple modulating agents (which may, but need not, be identical) to a support molecule (e.g., keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012). Within certain embodiments, modulating agents and molecules comprising other CAR sequence(s) (e.g., an RGD and/or LYHY (SEQ ID NO:55) sequence) may be attached to a support such as a polymeric matrix, preferably in an alternating pattern.

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent or linker). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl, thiol, carboxyl, ketone or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials. Multiple modulating agents and/or molecules comprising other CAR sequences may be attached, for example, by random coupling, in which equimolar amounts of such molecules are mixed with a matrix support and allowed to couple at random.

Although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, -Fab', Fab and F[v] fragments, which may be produced by conventional methods or by genetic or protein engineering. Linkage is generally covalent and may be achieved by, for example, direct condensation or other reactions, or by way of bi- or multi-functional linkers. Within other embodiments, it may also be possible to target a polynucleotide encoding a modulating agent to a target tissue, thereby increasing the local concentration of modulating agent. Such targeting may be achieved using well known techniques, including retroviral and adenoviral infection.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Within certain aspects of the present invention, one or more modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. A modulating agent (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration. For certain topical applications, formulation as a cream or lotion, using well known components, is preferred.

For certain embodiments, as discussed below, a pharmaceutical composition may further comprise a modulator of cell adhesion that is mediated by one or more molecules other than cadherins. Such modulators may generally be prepared as described above, incorporating one or more non-cadherin CAR sequences and/or antibodies thereto in place of the cadherin CAR sequences and antibodies. Such compositions are particularly useful for situations in which it is desirable to inhibit cell adhesion mediated by multiple cell-adhesion molecules, such as other members of the cadherin gene superfamily that are not classical cadherins (e.g., VE-cadherin, Dsg and Dsc); claudins; integrins; JAM and occludin. Preferred CAR sequences for use are as described above.

A pharmaceutical composition may also contain one or more drugs, which may be linked to a modulating agent or may be free within the composition. Virtually any drug may be administered in combination with a cyclic peptide as described herein, for a variety of purposes as described below. Examples of types of drugs that may be administered with a cyclic peptide include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

For imaging purposes, any of a variety of diagnostic agents may be incorporated into a pharmaceutical composition, either linked to a modulating agent or free within the composition. Diagnostic agents include any substance administered to illuminate a physiological function within a patient, while leaving other physiological functions generally unaffected. Diagnostic agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a colorimetric or fluorometric reaction. In general, such agents may be attached using a variety of techniques as described above, and may be present in any orientation.

The compositions described herein may be administered as part of a sustained release formulation (i.e., a formulation such as a capsule or sponge that effects a slow release of cyclic peptide following administration). Such formulations may generally be prepared using well known technology and administered by, for example, oral, rectal or subcutaneous implantation, or by implantation at the desired target site. Sustained-release formulations may contain a cyclic peptide dispersed in a carrier matrix and/or contained within a reservoir surrounded by a rate controlling membrane (see, e.g., European Patent Application 710,491A). Carriers for use within such formulations are biocompatible, and may also be biodegradable; preferably the formulation provides a relatively constant level of cyclic peptide release. The amount of cyclic peptide contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and the duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.2%, and more preferably from 0.0001% to 0.002%. Fluid compositions typically contain about 10 ng/ml to 5 mg/ml, preferably from about 10 $\mu$g to 2 mg/mL cyclic peptide. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agent Methods of Use

In general, the modulating agents and compositions described herein may be used for modulating a cadherin-mediated function (e.g., adhesion) of endothelial cells in vitro and/or in vivo. To modulate endothelial cell adhesion, an endothelial cell is contacted with a modulating agent either in vivo or in vitro. As noted above, modulating agents for purposes that involve the disruption of cadherin-mediated cell adhesion may comprise a cyclic peptide containing a single HAV sequence or multiple HAV sequences in close proximity, and/or an antibody (or an antigen-binding fragment thereof) that recognizes a cadherin CAR sequence. When it is desirable to also disrupt cell adhesion mediated by other adhesion molecules, a modulating agent may additionally comprise one or more CAR sequences bound by such adhesion molecules (and/or antibodies or fragments thereof that bind such sequences), preferably separated by linkers. As noted above, such linkers may or may not comprise one or more amino acids. For enhancing cell adhesion, a modulating agent may contain multiple HAV sequences or antibodies (or fragments), preferably separated by linkers, and/or may be linked to a single molecule or to a support material as described above.

Certain methods involving the disruption of cell adhesion as described herein have an advantage over prior techniques in that they permit the passage of molecules that are large and/or charged across barriers of endothelial cells. As discussed in greater detail below, modulating agents as described herein may also be used to disrupt or enhance endothelial cell adhesion and other functions in a variety of other contexts. Within the methods described herein, one or more modulating agents may generally be administered alone, or within a pharmaceutical composition. In each specific method described herein, as noted above, a targeting agent may be employed to increase the local concentration of modulating agent at the target site.

In one such aspect, the present invention provides methods for reducing unwanted endothelial adhesion by administering a modulating agent as described herein. Unwanted endothelial adhesion can occur, for example, between tumor cells, between tumor cells and normal cells or between normal cells as a result of surgery, injury, chemotherapy, disease, inflammation or other condition jeopardizing cell viability or function. Preferred modulating agents for use within such methods comprise one or more cyclic peptides such as N—Ac-CHAVC-NH$_2$ (SEQ ID NO:10), CHAVC-Y—NH$_2$ (SEQ ID NO:84), N—Ac-CHAVDC-NH$_2$ (SEQ ID NO:20), N—Ac-CHAVDIC-NH$_2$ (SEQ ID NO:50), N—Ac-CHAVDINC-NH$_2$ (SEQ ID NO:51), N—Ac-CHAVDINGC-NH$_2$ (SEQ ID NO:76), N—Ac-CAHAVC-NH$_2$ (SEQ ID NO:22), N—Ac-CAHAVDC-NH$_2$ (SEQ ID NO:26), N—Ac-CAHAVDIC-NH$_2$ (SEQ ID NO:24), N—Ac-CRAHAVDC-NH$_2$ (SEQ ID NO:28), N—Ac-CLRAHAVC-NH$_2$ (SEQ ID NO:30), N—Ac-CLRAHAVDC-NH$_2$ (SEQ ID NO:32), N—Ac-CSHAVC-NH$_2$ (SEQ ID NO:36), N—Ac-CFSHAVC-NH$_2$ (SEQ ID NO:85), N—Ac-CLFSHAVC-NH$_2$ (SEQ ID NO:86), N—Ac-CHAVSC-NH$_2$ (SEQ ID NO:38), N—Ac-CSHAVSC-NH$_2$ (SEQ ID NO:40), N—Ac-CSHAVSSC-NH$_2$ (SEQ ID NO:42), N—Ac-CHAVSSC-NH$_2$ (SEQ ID NO:44), N—Ac-KHAVD-NH$_2$ (SEQ ID NO:12), N—Ac-DHAVK-NH$_2$ (SEQ ID NO:14), N—Ac-KHAVE-NH$_2$ (SEQ ID NO:16), N—Ac-AHAVDI-NH$_2$ (SEQ ID NO:34), N—Ac-SHAVDSS-NH$_2$ (SEQ ID NO:77), N—Ac-KSHAVSSD-NH$_2$ (SEQ ID NO:48), N—Ac-CHAVC-S—NH$_2$ (SEQ ID NO:87), N—Ac—S-CHAVC-NH$_2$ (SEQ ID NO:88), N—Ac-CHAVC-SS—NH$_2$ (SEQ ID NO:89), N—Ac—S-CHAVC-S—NH$_2$ (SEQ ID NO:90), N—Ac-CHAVC-T—NH$_2$ (SEQ ID NO:91), N—Ac-CHAVC-E—NH$_2$ (SEQ ID NO:92), N—Ac-CHAVC-D—NH$_2$ (SEQ ID NO:93), N—Ac-CHAVYC-NH$_2$ (SEQ ID NO:94), CH$_3$—SO$_2$—HN-CHAVC-Y—NH$_2$ (SEQ ID NO:95), N—Ac—Y-CHAVC-NH$_2$, (SEQ ID NO:54), CH$_3$—SO$_2$—HN-CHAVC-NH$_2$ (SEQ ID NO:96), HC(O)—NH-CHAVC-NH$_2$ (SEQ ID NO:96), N—Ac-CHAVPen-NH$_2$ (SEQ ID NO:79), N—Ac-PenHAVC-NH$_2$ (SEQ ID NO:80), N—Ac-CHAVPC-NH$_2$ (SEQ ID NO:81) and derivatives thereof (e.g. in which terminal modifications are varied). In addition, a modulating agent may comprise the sequence RGD, which is bound by integrins, and/or the sequence LYHY (SEQ ID NO:55), which is bound by occludin, separated from the HAV sequence via a linker. Other CAR sequences that may be present include claudin, VE-cadherin and JAM CAR sequences as described above. Alternatively, a separate modulator of integrin, occludin-, VE-cadherin-, claudin and/or JAM-mediated cell adhesion may be administered in conjunction with the modulating agent(s), either within the same pharmaceutical composition or separately. Topical administration of the modulating agent(s) is generally preferred, but other means may also be employed. Preferably, a fluid composition for topical administration (comprising, for example, physiological saline) comprises an amount of cyclic peptide as described above, and more preferably an amount ranging from 10 $\mu$g/mL to 1 mg/mL. Creams may generally be formulated as described above. Topical administration in the surgical field may be given once at the end of surgery by irrigation of the wound, as an intermittent or continuous irrigation with use of surgical drains in the post operative period, or by the use of drains specifically inserted in an area of inflammation, injury or disease in cases where surgery does not need to be performed. Alternatively, parenteral or transcutaneous administration may be used to achieve similar results.

Within further aspects, a modulating agent may be used to inhibit angiogenesis (i.e., the growth of blood vessels from pre-existing blood vessels) in a mammal. In general, inhibition of angiogenesis may be beneficial in patients afflicted with diseases such as cancer or arthritis. Preferred modulating agents for inhibition of angiogenesis include those comprising one or more of N—Ac-CHAVC-NH$_2$ (SEQ ID NO:10), CHAVC-Y—NH$_2$ (SEQ ID NO:84), N—Ac-CHAVDC-NH$_2$ (SEQ ID NO:20), N—Ac-CHAVDIC-NH$_2$ (SEQ ID NO:50), N—Ac-CHAVDINC-NH$_2$ (SEQ ID NO:51), N—Ac-CHAVDINGC-NH$_2$ (SEQ ID NO:76), N—Ac-CAHAVC-NH$_2$ (SEQ ID NO:22), N—Ac-CAHAVDC-NH$_2$ (SEQ ID NO:26), N—Ac-CAHAVDIC-NH$_2$ (SEQ ID NO:24), N—Ac-CRAHAVDC-NH$_2$ (SEQ ID NO:28), N—Ac-CLRAHAVC-NH$_2$ (SEQ ID NO:30), N—Ac-CLRAHAVDC-NH$_2$ (SEQ ID NO:33), N—Ac-KHAVD-NH$_2$ (SEQ ID NO: 12), N—Ac-DHAVK-NH$_2$ (SEQ ID NO:14), N—Ac-KHAVE-NH$_2$ (SEQ ID NO:16), N—Ac-AHAVDI-NH$_2$ (SEQ ID NO:34), N—Ac-CHAVC-S—NH$_2$ (SEQ ID NO:87), N—Ac—S-CHAVC-NH$_2$ (SEQ ID NO:88), N—Ac-CHAVC-SS—NH$_2$ (SEQ ID NO:89), N—Ac—S-CHAVC-S—NH$_2$ (SEQ ID NO:90), N—Ac-CHAVC-T—NH$_2$ (SEQ ID NO:91), N—Ac-CHAVC-E—NH$_2$ (SEQ ID NO:92), N—Ac-CHAVC-D—NH$_2$ (SEQ ID NO:93), N—Ac-CHAVYC-NH$_2$ (SEQ ID NO:94), N—Ac—Y-CHAVC-NH$_2$ (SEQ ID NO:54), CH$_3$—SO$_2$—HN-CHAVC-Y—NH$_2$ (SEQ ID NO:95), CH$_3$—SO$_2$—HN-CHAVC-NH$_2$ (SEQ ID NO:96), HC(O)—NH-CHAVC-NH$_2$ (SEQ ID NO:96), N—Ac-CHAVPen-NH$_2$ (SEQ ID NO:79), N—Ac-PenHAVC-NH$_2$ (SEQ ID NO:80), N—Ac-CHAVPC-NH$_2$ (SEQ ID NO:81) and derivatives thereof (e.g, in which terminal modifications are varied). In addition, a modulating agent for use in inhibiting angiogenesis may comprise the sequence RGD, which is recognized by integrins, the occludin CAR sequence LYHY (SEQ ID NO:55), a VE-cadherin CAR sequence, a JAM CAR sequence and/or an claudin CAR sequence, separated from the HAV sequence via a linker. Alternatively, a separate modulator of integrin-, VE-cadherin-, claudin-, JAM- and/or occludin-mediated cell adhesion may be administered in conjunction with the modulating agent(s), either within the same pharmaceutical composition or separately.

The effect of a particular modulating agent on angiogenesis may generally be determined by evaluating the effect of the peptide on blood vessel formation. Such a determination may generally be performed, for example, using a chick chorioallantoic membrane assay, as described above and by Iruela-Arispe et al., *Molecular Biology of the Cell* 6:327–343, 1995. Briefly, a modulating agent may be embedded in a mesh composed of vitrogen at one or more concentrations (e.g., ranging from about 1 to 100 µg/mesh). The mesh(es) may then be applied to chick chorioallantoic membranes. After 24 hours, the effect of the peptide may be determined using computer assisted morphometric analysis. A modulating agent should inhibit angiogenesis by at least 25% at a concentration of 33 µg/mesh.

The addition of a targeting agent may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumor to maintain growth and microscopically by an absence of nerves at the periphery of the tumor.

The present invention also provides methods for increasing vasopermeability in a mammal by administering one or more modulating agents or pharmaceutical compositions. Within blood vessels, endothelial cell adhesion (mediated by N-cadherin) results in decreased vascular permeability. Accordingly, modulating agents as described herein may be used to increase vascular permeability. Within certain embodiments, preferred modulating agents for use within such methods include peptides capable of decreasing both endothelial and tumor cell adhesion. Such modulating agents may be used to facilitate the penetration of anti-tumor therapeutic or diagnostic agents (e.g., monoclonal antibodies) through endothelial cell permeability barriers and tumor barriers. Particularly preferred modulating agents for use within such methods include those that comprise one or more cyclic peptides such as N—Ac-CHAVC-NH$_2$ (SEQ ID NO:10), CHAVC-Y—NH$_2$ (SEQ ID NO:84), N—Ac-CHAVDC-NH$_2$ (SEQ ID NO:20), N—Ac-CHAVDIC-NH$_2$ (SEQ ID NO:50), N—Ac-CHAVDINC-NH$_2$ (SEQ ID NO:51), N—Ac-CHAVDINGC-NH$_2$ (SEQ ID NO:76), N—Ac-CAHAVC-NH$_2$ (SEQ ID NO:22), N—Ac-CAHAVDC-NH$_2$ (SEQ ID NO:26), N—Ac-CAHAVDIC-NH$_2$ (SEQ ID NO:24), N—Ac-CRAHAVDC-NH$_2$ (SEQ ID NO:28), N—Ac-CLRAHAVC-NH$_2$ (SEQ ID NO:30), N—Ac-CLRAHAVDC-NH$_2$ (SEQ ID NO:32), N—Ac-CSHAVC-NH$_2$ (SEQ ID NO:36), N—Ac-CFSHAVC-NH$_2$ (SEQ ID NO:85), N—Ac-CLFSHAVC-NH$_2$ (SEQ ID NO:36), N—Ac-CHAVSC-NH$_2$ (SEQ ID NO:38), N—Ac-CSHAVSC-NH$_2$ (SEQ ID NO:40), N—Ac-CSHAVSSC-NH$_2$ (SEQ ID NO:42), N—Ac-CHAVSSC-NH$_2$ (SEQ ID NO:44), N—Ac-KHAVD-NH$_2$ (SEQ ID NO:12), N—Ac-DHAVK-NH$_2$ (SEQ ID NO:14), N—Ac-KHAVE-NH$_2$ (SEQ ID NO:16), N—Ac-AHAVDI-NH$_2$ (SEQ ID NO:34), N—Ac-SHAVDSS-NH$_2$ (SEQ ID NO:77), N—Ac-KSHAVSSD-NH$_2$ (SEQ ID NO:48), N—Ac-CHAVC-S—NH$_2$ (SEQ ID NO:87), N—Ac—S-CHAVC-NH$_2$ (SEQ ID NO:88), N—Ac-CHAVC-SS—NH$_2$ (SEQ ID NO:89), N—Ac—S-CHAVC-S—NH$_2$ (SEQ ID NO:90), N—Ac-CHAVC-T—NH$_2$ (SEQ ID NO:91), N—Ac-CHAVC-E—NH$_2$ (SEQ ID NO:92), N—Ac-CHAVC-D—NH$_2$ (SEQ ID NO:93), N—Ac-CHAVYC-NH$_2$ (SEQ ID NO:94), CH$_3$—SO$_2$—HN-CHAVC-Y—NH$_2$ (SEQ ID NO:95), N—Ac—Y-CHAVC-NH$_2$ (SEQ ID NO:54), CH$_3$—SO$_2$-HN-CHAVC-NH$_2$ (SEQ ID NO:96), HC(O)—NH-CHAVC-NH$_2$ (SEQ ID NO:96), N—Ac-CHAVPen-NH$_2$ (SEQ ID NO:79), N—Ac-PenHAVC-NH$_2$ (SEQ ID NO:80), N—Ac-CHAVPC-NH$_2$ (SEQ ID NO:81) and derivatives thereof (e.g., in which terminal modifications are varied). In addition, a preferred modulating agent may comprise an occludin CAR sequence LYHY (SEQ ID NO:55) and/or a CAR sequence for VE-cadherin, JAM or claudin. As noted above, such an additional sequence may be separated from the HAV sequence via a linker. Alternatively, a separate modulator of occludin-, VE-cadherin-, claudin- and/or JAM-mediated cell adhesion may be administered in conjunction with one or modulating agents, either within the same pharmaceutical composition or separately.

Within certain embodiments, preferred modulating agents for use within such methods include cyclic peptides capable of decreasing both endothelial and tumor cell adhesion. Such modulating agents may be used to facilitate the penetration of anti-tumor therapeutic or diagnostic agents (e.g., monoclonal antibodies) through endothelial cell permeability barriers and tumor barriers. For example, a modulating agent may comprise an HAV sequence with flanking E-cadherin-specific sequences and an HAV sequence with flanking N-cadherin-specific sequences. Alternatively, separate modulating agents capable of disrupting N- and E-cadherin mediated adhesion may be administered concurrently.

In one particularly preferred embodiment, a modulating agent is further capable of disrupting cell adhesion mediated by multiple adhesion molecules. Such an agent may additionally comprise an RGD sequence, a VE-cadherin CAR sequence, a claudin CAR sequence, a JAM CAR sequence and/or the occludin CAR sequence LYHY (SEQ ID NO:55). Alternatively, a separate modulator of non-classical cadherin-mediated cell adhesion may be administered in conjunction with the modulating agent(s), either within the same pharmaceutical composition or separately. Fab fragments directed against any of the above CAR sequences may also be employed, either incorporated into a modulating agent or within a separate modulator that is administered concurrently.

Treatment with the modulating agents provided herein may serve to increase blood flow to a tumor. Such treatment may be appropriate, for example, prior to administration of an anti-tumor therapeutic or diagnostic agent (e.g., a monoclonal antibody or other macromolecule), an antimicrobial agent or an anti-inflammatory agent, in order to increase the concentration of such agents in the vicinity of the target tumor, organism or inflammation without increasing the overall dose to the patient. Modulating agents for use within such methods may be linked to a targeting agent to further increase the local concentration of modulating agent, although systemic administration of a vasoactive agent even in the absence of a targeting agent increases the perfusion of certain tumors relative to other tissues. Suitable targeting agents include antibodies and other molecules that specifically bind to tumor cells or to components of structurally abnormal blood vessels. For example, a targeting agent may be an antibody that binds to a fibrin degradation product or a cell enzyme such as a peroxidase that is released by granulocytes or other cells in necrotic or inflamed tissues.

Administration via intravenous injection or transdermal administration is generally preferred. Effective dosages are generally sufficient to increase localization of a subsequently administered diagnostic or therapeutic agent to an extent that improves the clinical efficacy of therapy of accuracy of diagnosis to a statistically significant degree. Comparison may be made between treated and untreated tumor host animals to whom equivalent doses of the diagnostic or therapeutic agent are administered. In general, dosages range as described above.

Within further aspects, the present invention provides methods for disrupting neovasculature (i.e., newly formed blood vessels). Such methods may be used to disrupt normal or pathological neovasculature in a variety of contexts.

Disruption of neovasculature is therapeutic for conditions in which the presence of newly formed blood vessels is related to the underlying disorder, its symptoms or its complications. For example, disorders that may be treated include, but are not limited to, benign prostatic hyperplasia, diabetic retinopathy, vascular restenosis, arteriovenous malformations, meningioma, hemangioma, neovascular glaucoma, psoriasis, angiofiboma, arthritis, atherosclerotic plaques, corneal graft neovascularization, hemophilic joints, hypertrophic scars, hemorrhagic telangiectasia, pyogenic granuloma, retrolental fibroplasias, scleroderma trachoma, vascular adhesions, synovitis, dermatitis, endometriosis, macular degeneration and exudative macular degeneration. Particularly preferred modulating agents for use within such methods include those that comprise one or more cyclic peptides such as N—Ac-CHAVC-NH$_2$ (SEQ ID NO: 10), CHAVC-Y—NH$_2$ (SEQ ID NO:84), N—Ac-CHAVDC-NH$_2$ (SEQ ID NO:20), N—Ac-CHAVDIC-NH$_2$ (SEQ ID NO:50), N—Ac-CHAVDINC-NH$_2$ (SEQ ID NO:51), N—Ac-CHAVDINGC-NH$_2$ (SEQ ID NO:76), N—Ac-CAHAVC-NH$_2$ (SEQ ID NO:22), N—Ac-CAHAVDC-NH$_2$ (SEQ ID NO:26), N—Ac-CAHAVDIC-NH$_2$ (SEQ ID NO:24), N—Ac-CRAHAVDC-NH$_2$ (SEQ ID NO:28), N—Ac-CLRAHAVC-NH$_2$ (SEQ ID NO:30), N—Ac-CLRAHAVDC-NH$_2$ (SEQ ID NO:32), N—Ac-CSHAVC-NH$_2$ (SEQ ID NO:36), N—Ac-CFSHAVC-NH$_2$ (SEQ ID NO:85), N—Ac-CLFSHAVC-NH$_2$ (SEQ ID NO:86), N—Ac-CHAVSC-NH$_2$ (SEQ ID NO:38), N—Ac-CSHAVSC-NH$_2$ (SEQ ID NO:40), N—Ac-CSHAVSSC-NH$_2$ (SEQ ID NO:42), N—Ac-CHAVSSC-NH$_2$ (SEQ ID NO:44), N—Ac-KHAVD-NH$_2$ (SEQ ID NO:12), N—Ac-DHAVK-NH$_2$ (SEQ ID NO:14), N—Ac-KHAVE-NH$_2$ (SEQ ID NO:16), N—Ac-AHAVDI-NH$_2$ (SEQ ID NO:34), N—Ac-SHAVDSS-NH$_2$ (SEQ ID NO:77), N—Ac-KSHAVSSD-NH$_2$ (SEQ ID NO:48), N—Ac-CHAVC-S—NH$_2$ (SEQ ID NO:87), N—Ac—S-CHAVC-NH$_2$ (SEQ ID NO:88), N—Ac-CHAVC-SS—NH$_2$ (SEQ ID NO:89), N—Ac—S-CHAVC-S—NH$_2$ (SEQ ID NO:90), N—Ac-CHAVC-T—NH$_2$ (SEQ ID NO:91), N—Ac-CHAVC-E—NH$_2$ (SEQ ID NO:92), N—Ac-CHAVC-D—NH$_2$ (SEQ ID NO:93), N—Ac-CHAVYC-NH$_2$ (SEQ ID NO:94), CH$_3$—SO$_2$—HN-CHAVC-Y—NH$_2$ (SEQ ID NO:95), N—Ac—Y-CHAVC-NH$_2$ (SEQ ID NO:54), CH$_3$—SO$_2$-HN-CHAVC-NH$_2$ (SEQ ID NO:96), HC(O)—NH-CHAVC-NH$_2$ (SEQ ID NO:96), N—Ac-CHAVPen-NH$_2$ (SEQ ID NO:79), N—Ac-PenHAVC-NH$_2$ (SEQ ID NO:80), N—Ac-CHAVPC-NH$_2$ (SEQ ID NO:81) and derivatives thereof (e.g., in which terminal modifications are varied). In addition, a preferred modulating agent may comprise an occludin CAR sequence LYHY (SEQ ID NO:55) and/or a CAR sequence for VE-cadherin, JAM or claudin. As noted above, such an additional sequence may be separated from the HAV sequence via a linker. Alternatively, a separate modulator of occludin-, VE-cadherin-, JAM and/or claudin-mediated cell adhesion may be administered in conjunction with one or modulating agents, either within the same pharmaceutical composition or separately.

Other aspects of the present invention provide methods that employ antibodies raised against the modulating agents. Such polyclonal and monoclonal antibodies may be raised against a cyclic peptide using conventional techniques known to those of ordinary skill in the art. See, e.g., Harlow and Lane, *Antibodies: A Laboratory Manual*, Cold Spring Harbor Laboratory, 1988. In one such technique, an immunogen comprising the cyclic peptide is initially injected into any of a wide variety of mammals (e.g., mice, rats, rabbits, sheep or goats). Because of its small size, the cyclic peptide should be joined to a carrier protein, such as bovine serum albumin or keyhole limpet hemocyanin. Following one or more injections, the animals are bled periodically. Polyclonal antibodies specific for the cyclic peptide may then be purified from such antisera by, for example, affinity chromatography using the polypeptide coupled to a suitable solid support.

Monoclonal antibodies specific for the cyclic peptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the immunogen. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction. Antibodies having the desired activity may generally be identified using immunofluorescence analyses of tissue sections, cell or other samples where the target cadherin is localized.

Cyclic peptides may also be used to generate monoclonal antibodies, as described above, that are specific for particular cadherins (e.g., antibodies that bind to N-cadherin, but do not bind significantly to E-cadherin). Such antibodies may generally be used for therapeutic, diagnostic and assay purposes.

Antibodies as described herein may be used in vitro or in vivo to modulate cell adhesion. Within certain embodiments, antibodies may be used within methods in which enhanced cell adhesion is desired, as described above. Antibodies may also be used as a "biological glue," as described above to bind multiple cadherin-expressing cells within a variety of contexts, such as to enhance wound healing and/or reduce scar tissue, and/or to facilitate cell adhesion in skin grafting or prosthetic implants. In general, the amount of matrix-linked antibody administered to a wound, graft or implant site varies with the severity of the wound and/or the nature of the wound, graft, or implant, but may vary as discussed above. Antibodies may also be linked to any of a variety of support materials, as described above, for use in tissue culture or bioreactors.

Within certain embodiments, antibodies (or, preferably, antigen-binding fragments thereof) may be used in situations where inhibition of cell adhesion is desired. Such antibodies or fragments may be used, for example, for treatment of demyelinating diseases, such as MS, or to inhibit interactions between tumor cells, as described above. The use of Fab fragments is generally preferred.

The following Examples are offered by way of illustration and not by way of limitation.

EXAMPLES

Example 1

Preparation of Representative Cyclic Peptides

This Example illustrates the solid phase synthesis of representative cyclic peptides.

Peptides were generally assembled on methylbenzhydrylamine resin (MBHA resin) for the C-terminal amide peptides. The traditional Merrifield resins were used for any C-terminal acid peptides. Bags of a polypropylene mesh material were filled with the resin and soaked in dichloromethane. The resin packets were washed three times with 5% diisopropylethylamine in dichloromethane and then washed with dichloromethane. The packets are then sorted and placed into a Nalgene bottle containing a solution of the amino acid of interest in dichloromethane. An equal amount of diisopropylcarbodiimide (DIC) in dichloromethane was added to activate the coupling reaction. The bottle was shaken for one hour to ensure completion of the reaction. The reaction mixture was discarded and the packets washed with DMF. The N-α-Boc was removed by acidolysis using a 55% TFA in dichloromethane for 30 minutes leaving the TFA salt of the α-amino group. The bags were washed and the synthesis completed by repeating the same procedure while substituting for the corresponding amino acid at the coupling step. Acetylation of the N-terminal was performed by reacting the peptide resins with a solution of acetic anhydride in dichloromethane in the presence of diisopropylethylamine. The peptide was then side-chain deprotected and cleaved from the resin at 0° C. with liquid HF in the presence of anisole as a carbocation scavenger.

The crude peptides were purified by reversed-phase high-performance liquid chromatography. Purified linear precursors of the cyclic peptides were solubilized in 75% acetic acid at a concentration of 2–10 mg/mL. A 10% solution of iodine in methanol was added dropwise until a persistent coloration was obtained. A 5% ascorbic acid solution in water was then added to the mixture until discoloration. The disulfide bridge containing compounds were then purified by HPLC and characterized by analytical HPLC and by mass spectral analysis.

N—Ac-CHAVC-NH$_2$ (SEQ ID NO:10) was synthesized on a 396–5000 Advanced ChemTech synthesizer using a Rink resin (4-(2',4'-Dimethoxyphenyl-Fmoc-aminomethyl)-phenoxy resin), which provided C-terminal amides using Fmoc chemistries. The Fmoc protecting group on the resin was removed with piperidine and coupling of the amino acids to the resin initiated. Two coupling reactions in NMP (N-methylpyrrolidinone) per amino acid were performed. The first coupling was carried out using DIC (diisopropylcarbodiimide) and the second coupling used HBTU (O-benzotriazole-N,N,N',N',-tetramethyluronium hexafluorophosphate) in the presence of DIPEA (diisopropylethylamine). Both couplings were done in the presence of HOBt (hydroxybenzotriazole) with the exception of histidine and the final cysteine. The trityl protecting group of the imidazole side chain of histidine is not stable in the presence of HOBt. Acetylation of the free amine on the N-terminus was carried out with acetic anhydride in NMP in the presence of DIPEA. The linear peptide was then cleaved from the resin with TFA in dichloromethane. This procedure also removed the trityl protecting group on the imidazole side chain of histidine. The crude linear peptide amide was then cyclized using chlorosilane-sulfoxide oxidation method to give the disulfide peptide. The crude cyclic peptide was purified using reverse-phase liquid chromatography. N—Ac-CHAVC-Y—NH$_2$ (SEQ ID NO:84) was synthesized using the same procedure, except that the cleavage cocktail (TFA, Dichloromethane) will also remove the OtBu protecting group of tyrosine.

Example 2

Disruption of Bovine Endothelial Cell Adhesion

This Example illustrates the use of representative cyclic peptides to disrupt adhesion of endothelial cells, which express N-cadherin.

Bovine pulmonary artery endothelial cells were harvested by sterile ablation and digestion in 0.1% collagenase (type II; Worthington Enzymes, Freehold, N.J.). Cells were maintained in Dulbecco's minimum essential medium (Clonetics; San Diego, Calif.) supplemented with 10% fetal calf serum (Atlantic Biologicals, Nor cross, Ga.) and 1% antibiotic-antimycotic at 37° C. in 7% $CO_2$ in air. Cultures were passaged weekly in trypsin-EDTA (Gibco, Grand Island, N.Y.) and seeded onto tissue culture plastic at 20,000 cells/cm$^2$ for all experiments. Endothelial cultures were used at 1 week in culture, which is approximately 3 days after culture confluency was established. The cells used in all protocols were between 4th passage and 10th passage. The cells were seeded onto coverslips and treated 30 minutes with N—Ac-CHAVC-NH$_2$ (SEQ ID NO:10) or N—Ac-CHGVC-NH$_2$ (SEQ ID NO:11) at 500 μg/ml and then fixed with 1% paraformaldehyde.

Figure 5A:
FIGS. 5A–5C are photographs showing monolayer cultures of bovine endothelial cells in the presence (FIG. 5A) and absence (FIG. 5C) of a representative cyclic peptide or in the presence of an inactive control peptide (FIG. 5B).
Figure 5B:
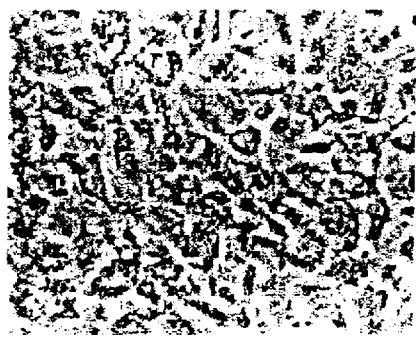
Figure 5C:
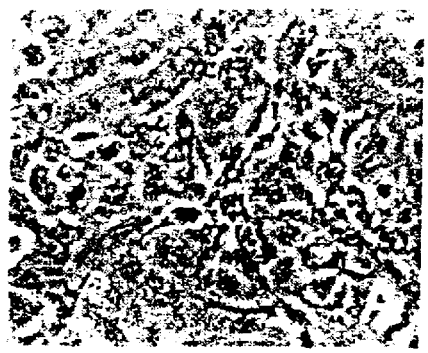

The peptide N—Ac-CHAVC-NH$_2$ (SEQ ID NO:10) disrupted the endothelial cell monolayer within 30 minutes after being added to the culture medium, whereas N—Ac-CHGVC-NH$_2$ (SEQ ID NO:11) had no affect on the cells (FIG. 5). Endothelial cell morphology was dramatically affected by N—Ac-CHAVC-NH$_2$ (SEQ ID NO:10), and the cells retracted from one another and became non-adherent. These data demonstrate that N—Ac-CHAVC-NH$_2$ (SEQ ID NO:10) is capable of inhibiting endothelial cell adhesion.

Figure 6A:
FIGS. 6A–6C are photographs showing monolayer cultures of bovine endothelial cells in the presence (FIG. 6A) and absence (FIG. 6C) of a representative cyclic peptide or in the presence of an iN-Active control peptide (FIG. 6B).
Figure 6B:
Figure 6C:
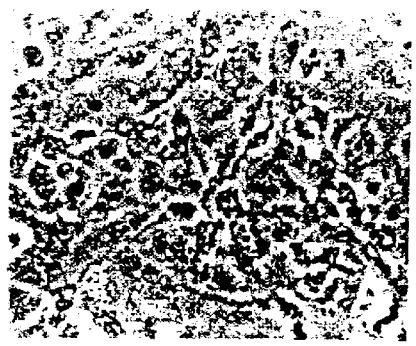
Figure 7A:
FIGS. 7A–7C are photographs showing monolayer cultures of bovine endothelial cells in the presence (FIG. 7A) and absence (FIG. 7C) of a representative cyclic peptide or in the presence of an iN-Active control peptide (FIG. 7B).
Figure 7B:
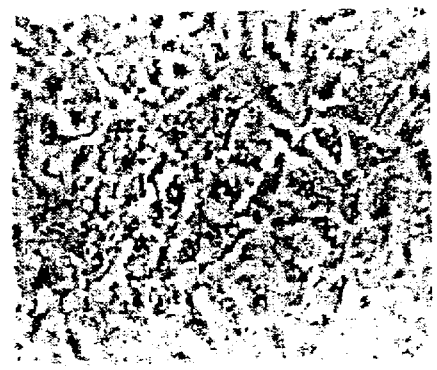
Figure 7C:
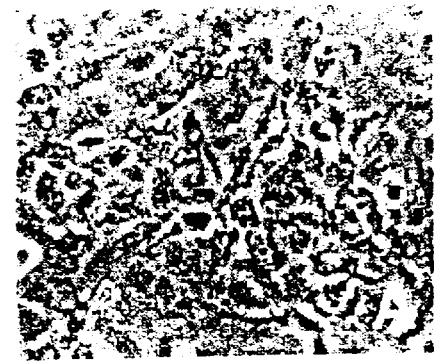
Figure 8A:
FIGS. 8A–8C are photographs showing monolayer cultures of bovine endothelial cells in the presence (FIG. 8A) and absence (FIG. 8C) of a representative cyclic peptide or in the presence of an iN-Active control peptide (FIG. 8B).
Figure 8B:
Figure 8C:
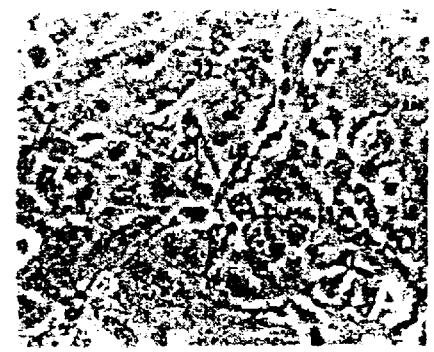

Under the same conditions, the cyclic peptides H-CHAVC-NH$_2$ (SEQ ID NO:11), N—Ac-CAHAVDIC-NH$_2$ (SEQ ID NO:24) (FIG. 6) and N—Ac-CHAVSC-NH$_2$ (SEQ ID NO:38) had no effect on endothelial cell morphology, indicating that not all cyclic HAV-containing peptides are capable of disrupting endothelial cell adhesion at a concentration of 500 μg/mL. It is not unexpected that the potencies of individual cyclic peptides will vary. The cyclic peptide N—Ac-CAHAVDC-NH$_2$ (SEQ ID NO:26; FIG. 7) had a slight effect while N—Ac-CSHAVSSC-NH$_2$ (SEQ ID NO:42; FIG. 8) disrupted the endothelial cell monolayer and caused the cells to retract from one another.

Example 3

Disruption of Angiogenesis

Blood vessels are composed of adherent endothelial cells. This Example illustrates the use of a representative cyclic peptide to block angiogenesis (the growth of blood vessels from pre-existing blood vessels).

The chick chorioallantoic membrane assay was used to assess the effects of cyclic peptides on angiogenesis (Iruela- Arispe et al., *Molecular Biology of the Cell* 6:327–343, 1995). Cyclic peptides were embedded in a mesh composed of vitrogen at concentrations of 3, 17, and 33 μg/mesh. The meshes were then applied to 12-day-old chick embryonic chorioallantoic membranes. After 24 hours, the effects of the peptides on angiogenesis were assessed by computer assisted morphometric analysis.

The ability of representative cyclic peptides to inhibit angiogenesis is illustrated by the results presented in Table 2. For each concentration of cyclic peptide, the percent inhibition of angiogenesis (relative to the level of angiogenesis in the absence of cyclic peptide) is provided. Assays were performed in the presence (+) or absence (−) of 0.01 mM VEGF. For example, the cyclic peptide N—Ac-CHAVC-NH$_2$ (SEQ ID NO:10) inhibited angiogenesis by 46%, 51%, and 51% at concentrations of 3, 17, and 33 μg/mesh, respectively. The N-cadherin selective peptides N—Ac-CAHAVDIC-NH$_2$ (SEQ ID NO:24) and N—Ac-CAHAVDC-NH$_2$ (SEQ ID NO:26) also inhibited angiogenesis significantly. The E-cadherin selective cyclic peptides N—Ac-CHAVSC-NH$_2$ (SEQ ID NO:38) and N—Ac-CSHAVSSC-NH$_2$ (SEQ ID NO:42), as well as the scrambled peptide N—Ac-CVAHC-NH$_2$ (SEQ ID NO:18), were found to be relatively iN-Active in this assay.

TABLE 2

Percent Inhibition of Angiogenesis by Varying Concentrations of Cyclic Peptides

| Compound | Concentration, μg/mesh ± VEGF | | | | | |
|---|---|---|---|---|---|---|
| | 3(−) | 3(+) | 17(−) | 17(+) | 33(−) | 33(+) |
| H—CHAVC—NH$_2$ (SEQ ID NO: 10) | 11% | 27% | 13% | 34% | 17% | 35% |
| N—Ac—CHAVSC—NH$_2$ (SEQ ID NO: 38) | 11% | 17% | 12% | 16% | 17% | 19% |
| N—Ac—CVAHC—NH$_2$ (SEQ ID NO: 18) | −1% | 7% | 13% | 24% | 12% | 25% |
| N—Ac—CHAVC—NH$_2$ (SEQ ID NO: 10) | 12% | 46% | 22% | 51% | 28% | 51% |
| N—Ac—CAHAVDIC—NH$_2$ (SEQ ID NO: 24) | −1% | 21% | 15% | 37% | 33% | 49% |
| N—Ac—CAHAVDC—NH$_2$ (SEQ ID NO: 26) | 21% | 59% | 27% | 72% | 31% | 79% |
| N—Ac—CSHAVSSC—NH$_2$ (SEQ ID NO: 42) | 1% | −3% | −3% | 12% | 17% | 7% |

Example 4

Toxicity and Cell Proliferation Studies

This Example illustrates the initial work to evaluate the cytotoxic effects of representative cyclic peptides.

N—Ac-CHAVC-NH$_2$ (SEQ ID NO:10) and the control peptide N—Ac-CHGVC-NH$_2$ (SEQ ID NO: 11) were evaluated for possible cytotoxic effects on human microvascular endothelial (HMVEC; Clonetics), human umbilical vein endothelial (HUVEC; ATCC #CRL-1730), IAFp2 (human fibroblast cell line; Institute Armand-Frapier, Montreal, Quebec), WI-38 (human fibroblast cell line; ATCC #CCL-75), MDA-MB231 (human breast cancer cell line; ATCC #HTB-26), and PC-3 (human prostate cancer cell line; ATCC #CRL-1435) cells utilizing the MTT assay (Plumb et al., *Cancer Res.* 49:4435–4440, 1989). Neither of the peptides was cytotoxic at concentrations up to and including 100 μM. Similarly, neither of the peptides was capable of inhibiting the proliferation of the above cell lines at concentrations up to 100 μM, as judged by $^3$H-thymidine incorporation assays.

In fact, none of the compounds tested thus far show any cytotoxicity at concentrations up to and including 100 μM (Tables 3 and 4). However, N—Ac-CHAVSC-NH$_2$ (SEQ ID NO:38), N—Ac-CHGVSC-NH$_2$ (SEQ ID NO:39), N—Ac-CVAHC-NH$_2$ (SEQ ID NO:18), N—Ac-CVGHC-NH$_2$ (SEQ ID NO:19) and N—Ac-CSHAVSSC-NH$_2$ (SEQ ID NO: 42) inhibited the proliferation of HUVEC at concentrations (IC$_{50}$ values) of 57 μM, 42 μM, 8 μM, 30 μM and 69 μM respectively, as judged by $^3$H-thymidine incorporation assays. N—Ac-CSHAVSSC-NH$_2$ (SEQ ID NO:42) also inhibited the proliferation of MDA-MB231 cells at a concentration of 76 μM and HMVEC cells at a concentration of 70 μM (Tables 3 and 4). N—Ac-CHAVSC-NH$_2$ (SEQ ID NO:38) inhibited the proliferation of MDA-MB231 cells at a concentration of 52 μM.

TABLE 3

Evaluation of Peptides for Cytotoxicity and Capacity to Inhibit Cell Proliferation of Normal Cells (IC$_5$0 in μM)

| | | Normal Cells | | | | | | | |
|---|---|---|---|---|---|---|---|---|---|
| | | HMVEC | | HUVEC | | IAFp2 | | WI-38 | |
| Peptide | SEQ ID | Cell prol | Cytotox | Cell Prol | Cytotox | Cell Prol | Cytotox | Cell Prol | Cytotox |
| N—Ac—CHGVC—NH$_2$ (control for #1) | 11 | >100 μM | >100 μM | >100 μM | >100 μM | >100 μM | >100 μM | >100 μM | >100 μM |
| N—Ac—CHAVC—NH$_2$ (#1) | 10 | >100 μM | >100 μM | >100 μM | >100 μM | >100 μM | >100 μM | >100 μM | >100 μM |
| H—CHGVC—NH$_2$ (control for #2) | 11 | >100 μM | >100 μM | >100 μM | >100 μM | >100 μM | >100 μM | >100 μM | >100 μM |
| H—CHAVC—NH$_2$ (#2) | 10 | >100 μM | >100 μM | >100 μM | >100 μM | >100 μM | >100 μM | >100 μM | >100 μM |
| N—Ac—CHGVSC—NH$_2$ (control for #18) | 39 | >100 μM | >100 μM | 42 μM | >100 μM | >100 μM | >100 μM | >100 μM | >100 μM |
| N—Ac—CHAVSC—NH$_2$* (#18) | 38 | >100 μM | >100 μM | 57 μM | >100 μM | >100 μM | >100 μM | >100 μM | >100 μM |

TABLE 3-continued

Evaluation of Peptides for Cytotoxicity and Capacity to Inhibit Cell Proliferation of Normal Cells
($IC_{50}$ in μM)

| Peptide | SEQ ID | Normal Cells | | | | | | | |
|---|---|---|---|---|---|---|---|---|---|
| | | HMVEC | | HUVEC | | IAFp2 | | WI-38 | |
| | | Cell prol | Cytotox | Cell Prol | Cytotox | Cell Prol | Cytotox | Cell Prol | Cytotox |
| N—Ac—CSHGVC—NH₂ (control for #16) | 37 | >100 μM | >100 μM | >100 μM | >100 μM | >100 μM | >100 μM | >100 μM | >100 μM |
| N—Ac—CSHAVC—NH₂ (#16) | 36 | >100 μM | >100 μM | >100 μM | >100 μM | >100 μM | >100 μM | >100 μM | >100 μM |
| N—Ac—CAHGVDC—NH₂ (control for #22) | 27 | >100 μM | >100 μM | >100 μM | >100 μM | >100 μM | >100 μM | >100 μM | >100 μM |
| N—Ac—CAHAVDC—NH₂ (#22) | 26 | >100 μM | >100 μM | >100 μM | >100 μM | >100 μM | >100 μM | >100 μM | >100 μM |
| N—Ac—KHGVD—NH₂ (control for #26) | 13 | >100 μM | >100 μM | >100 μM | >100 μM | >100 μM | >100 μM | >100 μM | >100 μM |
| N—Ac—KHAVD—NH₂ (#26) | 12 | >100 μM | >100 μM | >100 μM | >100 μM | >100 μM | >100 μM | >100 μM | >100 μM |
| H—CAHGVDC—NH₂ (control for #45) | 26 | >100 μM | >100 μM | >100 μM | >100 μM | >100 μM | >100 μM | >100 μM | >100 μM |
| H—CAHAVDC—NH₂ (#45) | 27 | >100 μM | >100 μM | >100 μM | >100 μM | >100 μM | >100 μM | >100 μM | >100 μM |
| H—CAHGVDIC—NH₂ (control for #47) | 25 | >100 μM | >100 μM | >100 μM | >100 μM | >100 μM | >100 μM | >100 μM | >100 μM |
| H—CAHAVDIC—NH₂ (#47) | 24 | >100 μM | >100 μM | >100 μM | >100 μM | >100 μM | >100 μM | >100 μM | >100 μM |
| N—Ac—CVGHC—NH₂ (control for #32) | 19 | >100 μM | >100 μM | 30 μM | >100 μM | >100 μM | >100 μM | >100 μM | >100 μM |
| N—Ac—CVAHC—NH₂ (#32) | 18 | >100 μM | >100 μM | 8 μM | >100 μM | >100 μM | >100 μM | >100 μM | >100 μM |
| N—Ac—CAHGVDIC—NH₂ (control for #14) | 25 | >100 μM | >100 μM | >100 μM | >100 μM | >100 μM | >100 μM | >100 μM | >100 μM |
| N—Ac—CAHAVDIC—NH₂ (#14) | 24 | >100 μM | >100 μM | >100 μM | >100 μM | >100 μM | >100 μM | >100 μM | >100 μM |
| N—Ac—CSHGVSSC—NH₂ (control for #24) | 43 | >100 μM | >100 μM | >100 μM | >100 μM | >100 μM | >100 μM | >100 μM | >100 μM |
| N—Ac—CSHAVSSC—NH₂* (#24) | 42 | 70 μM | >100 μM | 69 μM | >100 μM | >100 μM | >100 μM | >100 μM | >100 μM |

*Incompletely soluble in RPMI at 1 mM

TABLE 4

Evaluation of Peptides for Cytotoxicity and Capacity
to Inhibit Cell Proliferation of Tumoral Cells
($IC_{50}$ in μM)

| Peptide | SEQ ID | Tumoral Cells | | | |
|---|---|---|---|---|---|
| | | MDA-MB231 | | PC-3 | |
| | | Cell Prol | Cytotox | Cell Prol | Cytotox |
| N—Ac—CHGVC—NH₂ (control for #1) | 11 | >100 μM | >100 μM | >100 μM | >100 μM |
| N—Ac—CHAVC—NH₂ (#1) | 10 | >100 μM | >100 μM | >100 μM | >100 μM |
| H—CHGVC—NH₂ (control for #2) | 11 | >100 μM | >100 μM | >100 μM | >100 μM |
| H—CHAVC—NH₂ (#2) | 10 | >100 μM | >100 μM | >100 μM | >100 μM |
| N—Ac—CHGVSC—NH₂ (control for #18) | 39 | >100 μM | >100 μM | >100 μM | >100 μM |
| N—Ac—CHAVSC—NH₂* (#18) | 38 | 52 μM | >100 μM | >100 μM | >100 μM |
| N—Ac—CSHGVC—NH₂ (control for #16) | 37 | >100 μM | >100 μM | >100 μM | >100 μM |
| N—Ac—CSHAVC—NH₂ (#16) | 36 | >100 μM | >100 μM | >100 μM | >100 μM |
| N—Ac—CAHGVDC—NH₂ (control for #22) | 27 | >100 μM | >100 μM | >100 μM | >100 μM |
| N—Ac—CAHAVDC—NH₂ (#22) | 26 | >100 μM | >100 μM | >100 μM | >100 μM |
| N—Ac—KHGVD—NH₂ | 13 | >100 μM | >100 μM | >100 μM | >100 μM |

TABLE 4-continued

Evaluation of Peptides for Cytotoxicity and Capacity
to Inhibit Cell Proliferation of Tumoral Cells
($IC_50$ in $\mu M$)

| | | Tumoral Cells | | | |
| --- | --- | --- | --- | --- | --- |
| | SEQ | MDA-MB231 | | PC-3 | |
| Peptide | ID | Cell Prol | Cytotox | Cell Prol | Cytotox |
| (control for #26) N—Ac—KHAVD—$NH_2$ | 12 | >100 $\mu M$ | >100 $\mu M$ | >100 $\mu M$ | >100 $\mu M$ |
| (#26) H—CAHGVDC—$NH_2$ | 27 | >100 $\mu M$ | >100 $\mu M$ | >100 $\mu M$ | >100 $\mu M$ |
| (control for #45) H—CAHAVDC—$NH_2$ | 26 | >100 $\mu M$ | >100 $\mu M$ | >100 $\mu M$ | >100 $\mu M$ |
| (#45) H—CAHGVDIC—$NH_2$ | 25 | >100 $\mu M$ | >100 $\mu M$ | >100 $\mu M$ | >100 $\mu M$ |
| (control for #47) H—CAHAVDIC—$NH_2$ | 24 | >100 $\mu M$ | >100 $\mu M$ | >100 $\mu M$ | >100 $\mu M$ |
| (#47) N—Ac—CVGHC—$NH_2$ | 19 | >100 $\mu M$ | >100 $\mu M$ | >100 $\mu M$ | >100 $\mu M$ |
| (control for #32) N—Ac—CVAHC—$NH_2$ | 18 | >100 $\mu M$ | >100 $\mu M$ | >100 $\mu M$ | >100 $\mu M$ |
| (#32) N—Ac—CAHGVDIC—$NH_2$ | 25 | >100 $\mu M$ | >100 $\mu M$ | >100 $\mu M$ | >100 $\mu M$ |
| (control for #14) N—Ac—CAHAVDIC—$NH_2$ | 24 | >100 $\mu M$ | >100 $\mu M$ | >100 $\mu M$ | >100 $\mu M$ |
| (#14) N—Ac—CSHGVSSC—$NH_2$ | 43 | >100 $\mu M$ | >100 $\mu M$ | >100 $\mu M$ | >100 $\mu M$ |
| (control for #24) N—Ac—CSHAVSSC—$NH_2$* | 42 | 76 $\mu M$ | >100 $\mu M$ | >100 $\mu M$ | >100 $\mu M$ |
| (#24) | | | | | |

*Incompletely soluble in RPMI at 1 mM

Example 5

Chronic Toxicity Study

This Example illustrates a toxicity study performed using a representative cyclic peptide.

Varying amounts of H-CHAVC-$NH_2$ (SEQ ID NO:10; 2 mg/kg, 20 mg/kg and 125 mg/kg) were injected into mice intraperitoneally every day for three days. During the recovery period (days 4–8), animals were observed for clinical symptoms. Body weight was measured and no significant differences occurred. In addition, no clinical symptoms were observed on the treatment or recovery days. Following the four day recovery period, autopsies were performed and no abnormalities were observed.

Example 6

Acute Toxicity Study

This Example illustrates further toxicity studies.

Mice were injected intraperitoneally for seven consecutive days with 20 mg/kg of N—Ac-CHAVC-$NH_2$ (SEQ ID NO:10) and sacrificed 24 hr after treatment. No gross or histopathological findings related to the treatment were found.

Mice were injected intraperitoneally with 125 mg/kg of N—Ac-CHAVC-$NH_2$ (SEQ ID NO: 10) for three consecutive days and sacrificed on the fourth day. No gross or histopathological findings related to the treatment were found.

Rat were injected intravenously with 100 mg/kg of N—Ac-CHAVC-$NH_2$ (SEQ ID NO:10) with no gross or histopathological findings related to the treatment.

Mice were injected intravenously with either a saline control or 200 mg/kg of N—Ac-CHAVC-$NH_2$ (SEQ ID NO:10). Mice were sacrificed after 24 hours, or allowed a 14-day recovery period. In all cases, no animals died during the study, and no gross or histopathological findings related to the treatment were found.

Example 7

Stability of Cyclic Peptide in Blood

This Example illustrates the stability of a representative cyclic peptide in mouse whole blood.

Figure 9:
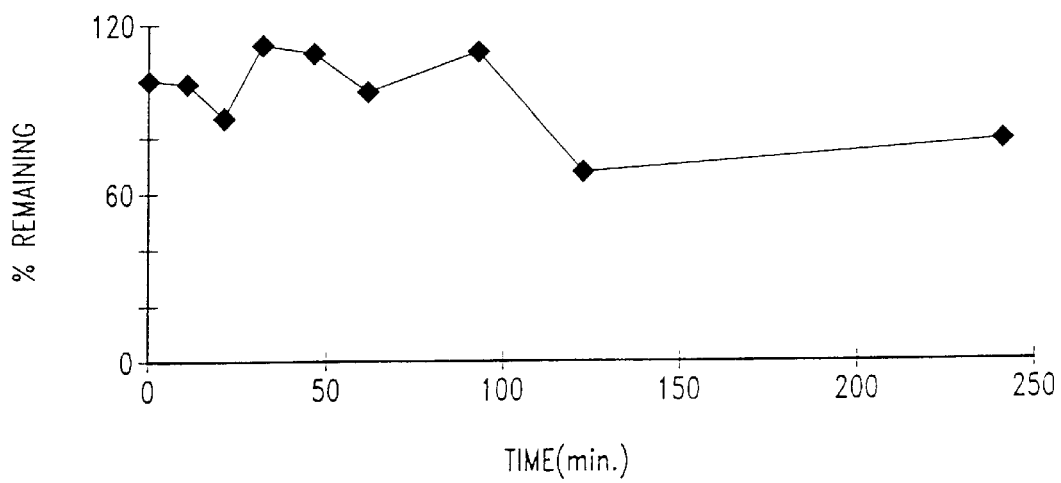
FIG. 9 is a graph illustrating the stability of a representative cyclic peptide in mouse whole blood. The percent of the cyclic peptide remaining in the blood was assayed at various time points, as indicated.

50 $\mu l$ of a stock solution containing 12.5 $\mu g/ml$ H-CHAVC-$NH_2$ (SEQ ID NO:10) was added to mouse whole blood and incubated at 37° C. Aliquots were removed at intervals up to 240 minutes, precipitated with acetonitrile, centrifuged and analyzed by HPLC. The results (Table 5 and FIG. 9) are expressed as % remaining at the various time points, and show generally good stability in blood.

TABLE 5

Stability of Representative Cyclic Peptide in Mouse Whole Blood

| Time (Min.) | Area 1 | Area 2 | Average | % Remaining |
| --- | --- | --- | --- | --- |
| 0 | 341344 | 246905 | 294124.5 | 100.00 |
| 10 | 308924 | 273072 | 290998 | 98.94 |
| 20 | 289861 | 220056 | 254958.5 | 86.68 |
| 30 | 353019 | 310559 | 331789 | 112.81 |
| 45 | 376231 | 270860 | 323545.5 | 110.00 |
| 60 | 373695 | 188255 | 280975 | 95.53 |
| 90 | 435555 | 216709 | 326132 | 110.88 |
| 120 | 231694 | 168880 | 200287 | 68.10 |
| 240 | 221952 | 242148 | 232050 | 78.90 |

Example 8

Modulating Agent-induced Reduction in Tumor Volume

This Example illustrates the use of a modulating agent for in vivo tumor reduction.

SKOV3 cells (ATCC) were grown to 70% confluence in Minimum Essential Medium (Life Technologies, Grand Island, N.Y.) supplemented with 10% Fetal Bovine Serum (Wisent, St. Bruno, Quebec) in a humidified atmosphere containing 5% $CO_2$. Cells were then dissociated with 0.02% PBS/EDTA. Total cell count and viable cell number was determined by trypan blue stain and a hemacytometer.

Approximately $1 \times 10^7$ cells were resuspended in 400 µl saline and injected in 6-week-old CD-1 nude mice (female, Charles River) subcutaneously. After 20 days of continuous tumor growth, tumor size was about 4.0 mm. The tumor-bearing animals were then injected intraperitoneally every day for 4 consecutive days with 20 mg/kg of the representative peptide modulating agent N—Ac-CHAVC-$NH_2$ (SEQ ID NO:10) and saline, for experimental and control respectively. Mice were sacrificed by cervical dislocation 4 days after final injection.

Figure 10A:
FIGS. 10A and 10B are photographs of human ovarian tumors grown in nude mice. Human ovarian cancer cells (SKOV3) were injected subcutaneously into nude mice. Tumors were grown to a size of 4 mm. Animals were then injected intraperitoneally, on four consecutive days, with 20 mg/kg of the representative cyclic peptide N—Ac-CHAVC-NH$_2$ (FIG. 10B; SEQ ID NO:10) or saline (FIG. 10A). Mice were sacrificed, and tumor tissue was sectioned and stained with hematoxylin/eosin.
Figure 10B:
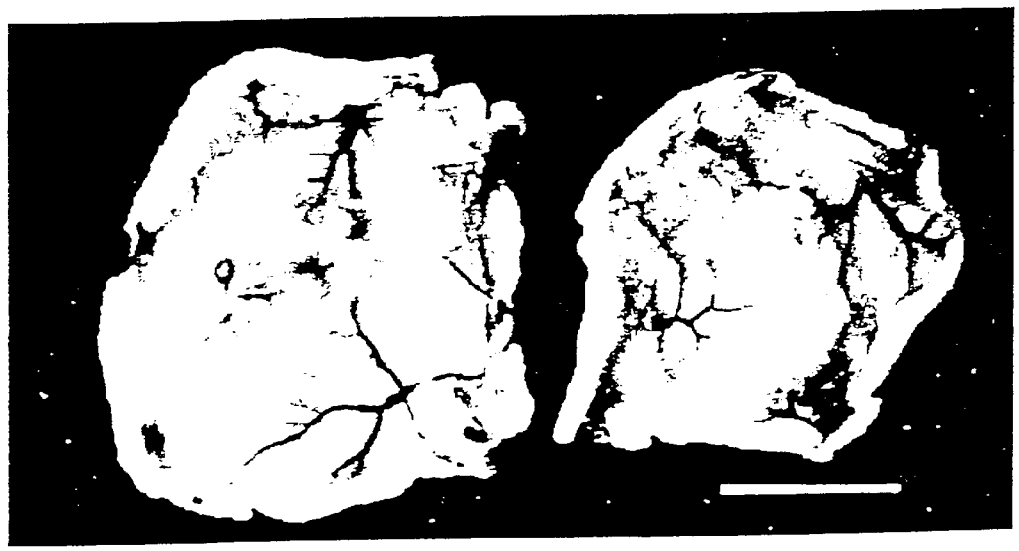

Tumor tissue was dissected and fixed in PBS with 4% paraformaldehyde for 48 hours. Specimens were then dehydrated in a series of alcohol incubations, and embedded in paraffin wax. Tissues were sectioned, rehydrated and stained with hematoxylin/eosin for morphological purposes. Representative sections obtained from treated and untreated mice are shown in FIGS. 10B and 10A, respectively.

Figure 11:
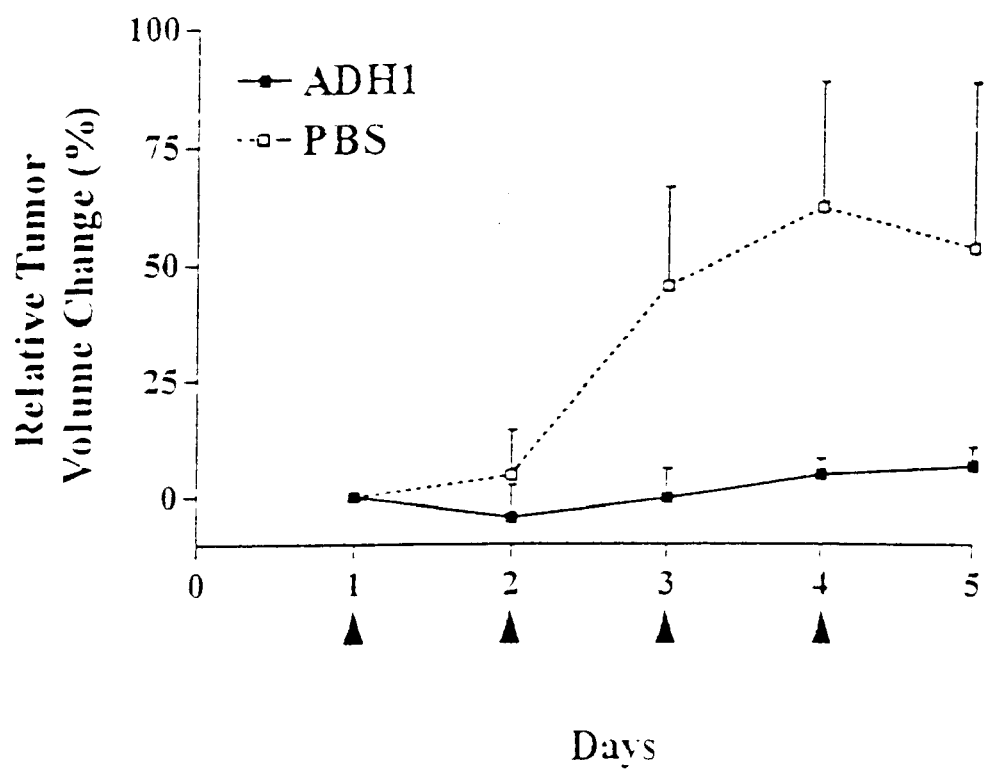
FIG. 11 is a graph showing the relative tumor volume change for human ovarian tumors in nude mice following intraperitoneal injection for four consecutive days as indicated, with 20 mg/kg of the representative cyclic peptide N—Ac-CHAVC-NH$_2$ (solid squares; SEQ ID NO:10) or saline (open squares).

FIG. 11 presents the results in graph form, showing the percent reduction in tumor volume over the four day treatment period. These data indicate that treatment with the cyclic peptide modulating agent prevents detectable tumor growth and results in a substantial decrease in tumor size, in comparison to the control.

Figure 12A:
FIGS. 12A and 12B are photographs of human ovarian tumors grown in nude mice. Animals were injected intraperitoneally, on four consecutive days, with 2 mg/kg of the representative cyclic peptide modulating agent N—Ac-CHAVC-NH$_2$ (FIG. 12A; SEQ ID NO:10) or saline (FIG. 12B). Mice were sacrificed 24 hours after the last injection, and tumor tissue was sectioned and stained with hematoxylin/eosin.
Figure 12B:

Within similar experiments, tumor-bearing nude mice as described above were injected intraperitoneally with 2 mg/kg of the representative peptide modulating agent N—Ac-CHAVC-$NH_2$ (SEQ ID NO:10) and saline, for experimental and control respectively. Injections were performed every day for 4 days. Mice were sacrificed 24 hours after the last injection. Tumor tissue was fixed, sectioned and stained as described above. Representative sections obtained from treated and untreated mice are shown in FIGS. 12A and 12B, respectively.

Figure 13:
FIG. 13 is a photograph of a human ovarian tumor grown in a nude mouse, as described for FIG. 12A, showing leakage of red blood cells into the tumor mass.
Figure 14:
FIG. 14 is a photograph of a human ovarian tumor grown in a nude mouse, as described for FIG. 12A, showing a blood vessel that has been breached.

FIGS. 13 and 14 show close up images of the effect of the modulating agent on tumor blood vessels. In FIG. 13, red blood cells can be seen leaking into the tumor mass. FIG. 14 shows a blood vessel that has been breached and blood cells gathering and escaping at that point.

Figure 15:
FIG. 15 is a photograph of a human ovarian tumor grown in a nude mouse, as described for FIG. 12B (i.e., untreated tumor), where the tumor section is stained for Von Willebrand Factor VIII.
Figure 16:
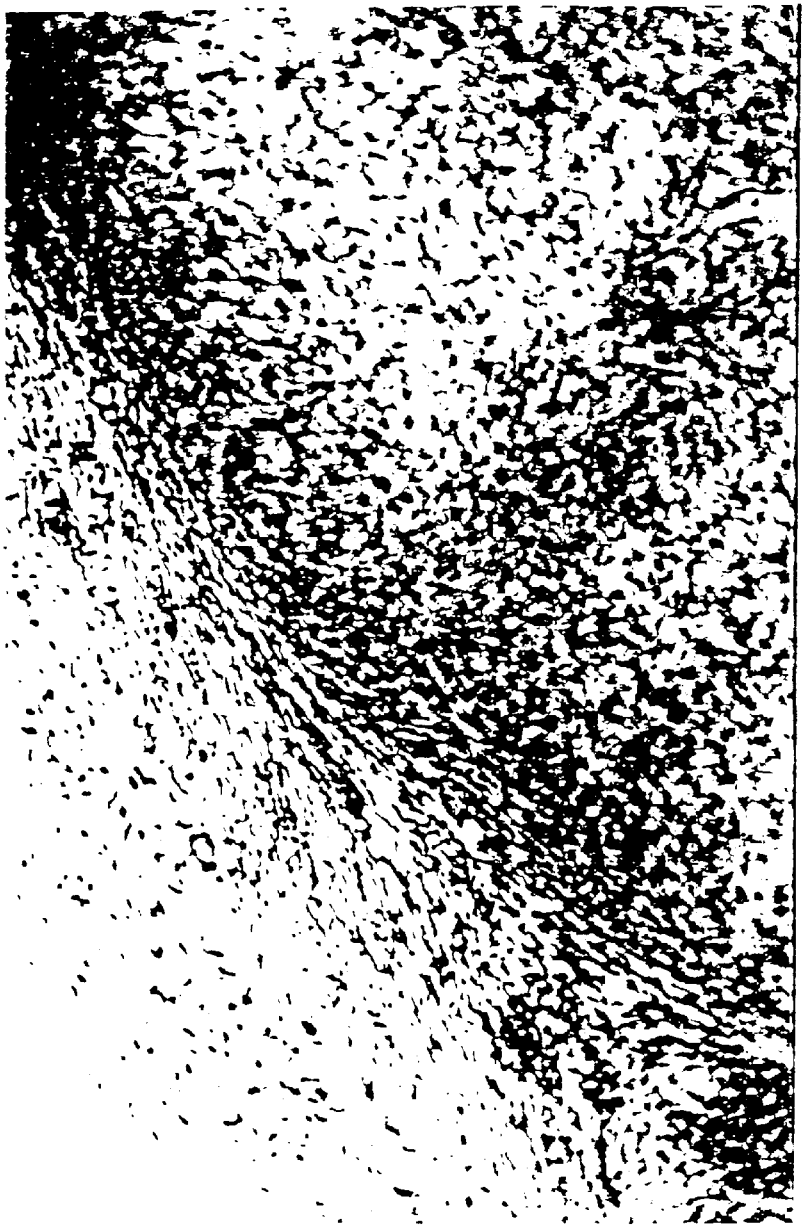
FIG. 16 is a photograph of a human ovarian tumor grown in a nude mouse, as described for FIG. 12A (i.e., tumor treated with the representative cyclic peptide modulating agent N—Ac-CHAVC-NH$_2$ (SEQ ID NO:10)), where the tumor section is stained for Von Willebrand Factor VIII.

To further demonstrate the effect of the representative modulating agent N—Ac-CHAVC-$NH_2$ (SEQ ID NO:10) on tumor blood vessels, sections of the tumors described above were stained for Von Willebrand Factor VIII, a blood vessel-specific marker. An untreated tumor is shown in FIG. 15, and a treated tumor section is shown in FIG. 16. Taken together, these results clearly demonstrate that the representative modulating agent is capable of damaging tumor blood vessels and stopping tumor growth in vivo.

From the foregoing, it will be evident that although specific embodiments of the invention have been described herein for the purpose of illustrating the invention, various modifications may be made without deviating from the spirit and scope of the invention. Accordingly, the present invention is not limited except as by the appended claims.

---

What is claimed is:

1. A method for modulating endothelial cell adhesion, comprising contacting an endothelial cell with an effective amount of a modulating agent comprising the sequence His-Ala-Val within a cyclic peptide ring that contains 4–15 amino acid residues and thereby modulating endothelial cell adhesion.

2. A method according to claim 1, wherein the cyclic peptide has the formula:

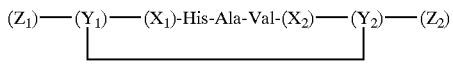

$(Z_1)-(Y_1)-(X_1)\text{-His-Ala-Val-}(X_2)-(Y_2)-(Z_2)$ wherein $X_1$ and $X_2$ are optional, and if present, are independently selected from the group consisting of amino acid residues and combinations thereof in which the residues are linked by peptide bonds, and wherein $X_1$ and $X_2$ independently range in size from 0 to 10 residues; wherein $Y_1$ and $Y_2$ are independently selected from the group consisting of amino acid residues, and wherein a covalent bond is formed between residues $Y_1$ and $Y_2$; and wherein $Z_1$ and $Z_2$ are optional, and if present, are independently selected from the group consisting of amino acid residues and combinations thereof in which the residues are linked by peptide bonds.

3. A method according to claim 1, wherein the peptide has an N-terminal acetyl, formyl or mesyl group.

4. A method according to claim 2, wherein $Y_1$ and $Y_2$ are each independently selected from the group consisting of cysteine, penicillamine, β,β-tetramethylene cysteine, β,β-pentamethylene cysteine, β,β-mercaptopropionic acid, β,β-pentamethylene-β-mercaptopropionic acid, 2-mercaptobenzene, 2-mercaptoaniline and 2-mercaptoproline.

5. A method according to claim 2, wherein $Y_1$ and $Y_2$ are cysteine residues.

6. A method according to claim 1, wherein the cyclic peptide comprises a sequence selected from the group consisting of: Cys-His-Ala-Val-Cys (SEQ ID NO: 10), Cys-His-Ala-Val-Asp-Cys (SEQ ID NO:20), Cys-Ala-His-Ala-Val-Cys (SEQ ID NO:22), Cys-Ala-His-Ala-Val-Asp-Cys (SEQ ID NO:26), Cys-Ala-His-Ala-Val-Asp-Ile-Cys (SEQ ID NO:24), Cys-Arg-Ala-His-Ala-Val-Asp-Cys (SEQ ID NO:28), Cys-Leu-Arg-Ala-His-Ala-Val-Cys (SEQ ID NO:30), Cys-Leu-Arg-Ala-His-Ala-Val-Asp-Cys (SEQ ID NO:32), Lys-His-Ala-Val-Asp (SEQ ID NO:12), Asp-His-Ala-Val-Lys (SEQ ID NO:14), Lys-His-Ala-Val-Glu (SEQ ID NO:16), Ala-His-Ala-Val-Asp-Ile (SEQ ID NO:34), Ser-His-Ala-Val-Asp-Ser-Ser (SEQ ID NO:77), Lys-Ser-His-Ala-Val-Ser-Ser-Asp (SEQ ID NO:48), Cys-His-Ala-Val-Cys-Ser (SEQ ID NO:87), Cys-His-Ala-Val-Cys-Ser-Ser (SEQ ID NO:89), Ser-Cys-His-Ala-Val-Cys-Ser (SEQ ID NO:90), Cys-His-Ala-Val-Cys-Tyr (SEQ ID NO:95), Tyr-Cys-His-Ala-Val-Cys (SEQ ID NO:54), Cys-His-Ala-Val-Cys-Thr (SEQ ID NO:91), Cys-His-Ala-Val-Cys-Asp (SEQ ID NO:93); and Cys-His-Ala-Val-Cys-Glu (SEQ ID NO:92), wherein a disulfide bond is formed between the two cysteines in the sequences of SEQ ID NOs:10, 20, 22, 26, 24, 28, 30, 32, 87, 89, 90, 95, 54, 91, 93 and 92, or, an amide bond is formed between the N- and C-terminal amino acid residues in the sequences of SEQ ID NOs:12, 14, 16, 34, 77 and 48.

7. A method according to claim 6, wherein the cyclic peptide has an N-terminal acetyl or $CH_3$—$SO_2$— group and a C-terminal amide group.

8. A method according to claim 1, wherein the agent is linked to a targeting agent.

9. A method according to claim 1, wherein the agent is linked to a drug.

10. A method according to claim 1, wherein the agent further comprises one or more of:
   (a) a cell adhesion recognition sequence that binds an adhesion molecule, wherein the cell adhesion recognition sequence is separated from any His-Ala-Val sequence(s) by a linker; or
   (b) an antibody or antigen-binding fragment thereof that specifically binds to a cell adhesion recognition sequence bound by an adhesion molecule;
   wherein the adhesion molecule is selected from the group consisting of integrins, occludin, claudins, JAM and VE-cadherin, and wherein the adhesion molecule mediates cell adhesion.

11. A method according to claim 1, wherein the agent is linked to a detectable marker.

12. A method according to claim 1, wherein the agent is present within a pharmaceutical composition comprising a physiologically acceptable carrier.

13. A method according to claim 2, wherein the composition further comprises a drug.

14. A method according to claim 2, wherein the agent is present within a sustained-release formulation.

15. A method according to claim 12, wherein the composition further comprises one or more of:
 (a) a peptide comprising a cell adhesion recognition sequence that binds an adhesion molecule; or
 (b) an antibody or antigen-binding fragment thereof that specifically binds to a cell adhesion recognition sequence bound by an adhesion molecule;
  wherein the adhesion molecule is selected from the group consisting of integrins, occludin, claudins, JAM and VE-cadherin, and wherein the adhesion molecule mediates cell adhesion.

16. A method according to claim 1, wherein the agent inhibits endothelial cell adhesion.

17. A method according to claim 1, wherein the agent enhances endothelial cell adhesion.

18. A method according to claim 1, wherein the agent further comprises one or more of:
 (a) a cell adhesion recognition sequence that binds an adhesion molecule, wherein the cell adhesion recognition sequence is separated from any His-Ala-Val sequence(s) by a linker; and
 (b) an antibody or antigen-binding fragment thereof that specifically binds to a cell adhesion recognition sequence bound by an adhesion molecule;
  wherein the adhesion molecule is selected from the group consisting of integrins, occludin, claudins, JAM and VE-cadherin, and wherein the adhesion molecule mediates cell adhesion.

19. A method according to claim 12, wherein the composition further comprises one or more of:
 (a) a peptide comprising a cell adhesion recognition sequence that binds an adhesion molecule; and
 (b) an antibody or antigen-binding fragment thereof that specifically binds to a cell adhesion recognition sequence bound by an adhesion molecule;
  wherein the adhesion molecule is selected from the group consisting of integrins, occludin, claudins, JAM and VE-cadherin, and wherein the adhesion molecule mediates cell adhesion.

* * * * *

UNITED STATES PATENT AND TRADEMARK OFFICE
CERTIFICATE OF CORRECTION

PATENT NO. : 6,610,821 B1
DATED : August 26, 2003
INVENTOR(S) : Orest W. Blaschuk et al.

It is certified that error appears in the above-identified patent and that said Letters Patent is hereby corrected as shown below:

<u>Column 2,</u>
Line 53, "β,β-mercaptopropionic acid," should read as -- β-mercaptopropionic acid, --.

Signed and Sealed this

Twenty-third Day of March, 2004

JON W. DUDAS
*Acting Director of the United States Patent and Trademark Office*